US012683001B1

(12) United States Patent
Dods et al.

(10) Patent No.: US 12,683,001 B1
(45) **Date of Patent: \*Jul. 14, 2026**

(54) DECENTRALIZED IDENTITY AUTHENTICATION FRAMEWORK FOR DISTRIBUTED DATA

(71) Applicant: LEDGERDOMAIN INC., Las Vegas, NV (US)

(72) Inventors: Victor Bovee Dods, Orinda, CA (US); Leonid Alekseyev, San Francisco, CA (US); William Jack, Cambridge, MA (US); Benjamin James Taylor, Las Vegas, NV (US)

(73) Assignee: LEDGERDOMAIN INC., Las Vegas, NV (US)

( * ) Notice: Subject to any disclaimer, the term of this patent is extended or adjusted under 35 U.S.C. 154(b) by 188 days.

This patent is subject to a terminal disclaimer.

(21) Appl. No.: 18/372,029

(22) Filed: Sep. 22, 2023

Related U.S. Application Data

(63) Continuation of application No. 17/492,488, filed on Oct. 1, 2021, now Pat. No. 11,769,577, which is a
(Continued)

(51) Int. Cl.
*G16H 20/10* (2018.01)
*G06F 17/18* (2006.01)
(Continued)

(52) U.S. Cl.
CPC .............. *G16H 20/10* (2018.01); *G06F 17/18* (2013.01); *G06F 18/22* (2023.01); *G06F 18/23* (2023.01);
(Continued)

(58) Field of Classification Search
CPC ..... G16H 20/10; G06F 17/18; G06F 21/6227; G06K 9/6215; G06K 9/6218; G06N 3/08;
(Continued)

(56) References Cited

U.S. PATENT DOCUMENTS

| | | | |
|---|---|---|---|
| 7,170,391 | B2 | 1/2007 | Lane et al. |
| 9,870,508 | B1 | 1/2018 | Hodgson et al. |

(Continued)

FOREIGN PATENT DOCUMENTS

| | | |
|---|---|---|
| CN | 110597902 A | 12/2019 |
| WO | 2018206408 A1 | 11/2018 |

(Continued)

OTHER PUBLICATIONS

U.S. Appl. No. 18/372,037, filed Sep. 22, 2023, Pending.
(Continued)

*Primary Examiner* — Blake I Narramore
(74) *Attorney, Agent, or Firm* — Haynes Beffel & Wolfeld LLP; Andrew L. Dunlap; Paul A. Durdik

(57) ABSTRACT

Disclosed is a method for authenticating requestors and granting access to a permissioned blockchain network shared among enterprise entities. A decentralized registry of credentialled users, in which credentialled users guard their own access information by keeping a private key of a public-private keypair enables systems to avoid keeping information of a large number of users in large, vulnerable containers. A further method removes authenticated users seeking to be forgotten from the registry of users and deletes any personally identifiable information of the withdrawing users.

24 Claims, 46 Drawing Sheets
(4 of 46 Drawing Sheet(s) Filed in Color)

Related U.S. Application Data continuation-in-part of application No. 17/384,585, filed on Jul. 23, 2021, now Pat. No. 11,829,510, which is a continuation of application No. 17/063, 605, filed on Oct. 5, 2020, now Pat. No. 11,081,219.

(60) Provisional application No. 63/122,875, filed on Dec. 8, 2020, provisional application No. 62/961,594, filed on Jan. 15, 2020.

(51) Int. Cl.

| | |
|---|---|
| *G06F 18/22* | (2023.01) |
| *G06F 18/23* | (2023.01) |
| *G06F 21/62* | (2013.01) |
| *G06N 3/08* | (2023.01) |
| *G06N 20/00* | (2019.01) |
| *H04L 9/00* | (2022.01) |
| *H04L 9/06* | (2006.01) |

(52) U.S. Cl.
CPC ........... *G06F 21/6227* (2013.01); *G06N 3/08* (2013.01); *G06N 20/00* (2019.01); *H04L 9/0643* (2013.01); *H04L 9/50* (2022.05); *H04L 2463/081* (2013.01)

(58) Field of Classification Search
CPC ................. G06N 20/00; H04L 9/0643; H04L 2209/38; H04L 2463/081
See application file for complete search history.

(56) References Cited

U.S. PATENT DOCUMENTS

| | | | |
|---|---|---|---|
| 10,268,974 | B2 | 4/2019 | Wiig et al. |
| 10,356,087 | B1 | 7/2019 | Vetter et al. |
| 10,491,404 | B1 | 11/2019 | Yamamoto |
| 10,491,578 | B1 | 11/2019 | Hebert et al. |
| 10,496,802 | B2 * | 12/2019 | Weis .................... H04W 12/06 |
| 10,509,684 | B2 | 12/2019 | Florissi et al. |
| 10,516,525 | B2 | 12/2019 | Bhattacharya et al. |
| 10,540,704 | B2 | 1/2020 | Mazed et al. |
| 10,542,046 | B2 | 1/2020 | Katragadda et al. |
| 10,990,693 | B1 | 4/2021 | Newman |
| 11,468,046 | B2 | 10/2022 | Conley et al. |
| 11,509,709 | B1 | 11/2022 | Basak et al. |
| 11,736,290 | B1 | 8/2023 | Dods et al. |
| 11,741,215 | B1 | 8/2023 | Dods et al. |
| 11,741,216 | B1 | 8/2023 | Dods et al. |
| 11,769,577 | B1 | 9/2023 | Dods et al. |
| 11,829,510 | B2 | 11/2023 | Dods et al. |
| 11,848,754 | B1 | 12/2023 | Dods et al. |
| 2012/0130905 | A1 | 5/2012 | Tsudik et al. |
| 2014/0006048 | A1 * | 1/2014 | Liberty .............. G06Q 30/0241 705/2 |
| 2014/0025443 | A1 * | 1/2014 | Onischuk ............... G07C 13/00 705/12 |
| 2014/0040153 | A1 | 2/2014 | Singh et al. |
| 2014/0108043 | A1 | 4/2014 | Ach et al. |
| 2015/0039700 | A1 | 2/2015 | West et al. |
| 2015/0262171 | A1 | 9/2015 | Langschaedel et al. |
| 2015/0269379 | A1 | 9/2015 | Ramzan et al. |
| 2016/0125199 | A1 * | 5/2016 | Lee ....................... G06F 21/316 726/28 |
| 2016/0155069 | A1 * | 6/2016 | Hoover .................. G06Q 30/06 706/12 |
| 2016/0212146 | A1 | 7/2016 | Wilson |
| 2017/0103167 | A1 | 4/2017 | Shah |
| 2017/0221032 | A1 | 8/2017 | Mazed |
| 2017/0286880 | A1 | 10/2017 | Wiig et al. |
| 2017/0310653 | A1 | 10/2017 | Zhang |
| 2017/0337588 | A1 | 11/2017 | Chittilappilly et al. |
| 2018/0048461 | A1 | 2/2018 | Jutla et al. |
| 2018/0114169 | A1 | 4/2018 | Wiig et al. |
| 2018/0139186 | A1 | 5/2018 | Castagna |

| | | | |
|---|---|---|---|
| 2018/0341648 | A1 | 11/2018 | Kakavand et al. |
| 2019/0012249 | A1 | 1/2019 | Mercuri et al. |
| 2019/0020661 | A1 | 1/2019 | Zhang |
| 2019/0026450 | A1 | 1/2019 | Egner et al. |
| 2019/0051079 | A1 | 2/2019 | Venkataraman et al. |
| 2019/0052453 | A1 | 2/2019 | de Ligt |
| 2019/0057386 | A1 | 2/2019 | Fazeli et al. |
| 2019/0058599 | A1 | 2/2019 | Takada Chino et al. |
| 2019/0068562 | A1 * | 2/2019 | Iyer ...................... H04L 9/0637 |
| 2019/0075102 | A1 | 3/2019 | Kim et al. |
| 2019/0108898 | A1 | 4/2019 | Gulati |
| 2019/0138905 | A1 | 5/2019 | Akella et al. |
| 2019/0138971 | A1 | 5/2019 | Uggirala et al. |
| 2019/0141119 | A1 | 5/2019 | Bernat et al. |
| 2019/0171438 | A1 | 6/2019 | Franchitti |
| 2019/0180276 | A1 | 6/2019 | Lee et al. |
| 2019/0222570 | A1 | 7/2019 | Krishan |
| 2019/0228174 | A1 | 7/2019 | Withrow et al. |
| 2019/0251295 | A1 | 8/2019 | Vieyra |
| 2019/0281066 | A1 | 9/2019 | Simons |
| 2019/0325507 | A1 | 10/2019 | Rowley et al. |
| 2019/0333116 | A1 | 10/2019 | Bhardwaj et al. |
| 2019/0334716 | A1 | 10/2019 | Kocsis et al. |
| 2019/0392162 | A1 | 12/2019 | Stern et al. |
| 2020/0005133 | A1 | 1/2020 | Zhang et al. |
| 2020/0013229 | A1 | 1/2020 | Lee et al. |
| 2020/0019288 | A1 | 1/2020 | D'Amore et al. |
| 2020/0084483 | A1 | 3/2020 | Brown et al. |
| 2020/0110821 | A1 | 4/2020 | Chan et al. |
| 2020/0118060 | A1 | 4/2020 | Mukherjee et al. |
| 2020/0137557 | A1 | 4/2020 | Touati et al. |
| 2020/0153606 | A1 | 5/2020 | Li et al. |
| 2020/0186358 | A1 | 6/2020 | Capola et al. |
| 2020/0213218 | A1 | 7/2020 | Demeilliez et al. |
| 2020/0219099 | A1 | 7/2020 | Mohassel et al. |
| 2020/0252205 | A1 | 8/2020 | Padmanabhan |
| 2020/0258166 | A1 | 8/2020 | Cross et al. |
| 2020/0265031 | A1 | 8/2020 | Greven |
| 2020/0268260 | A1 | 8/2020 | Tran |
| 2020/0294033 | A1 | 9/2020 | Wilson et al. |
| 2020/0320207 | A1 | 10/2020 | Beno et al. |
| 2020/0322169 | A1 | 10/2020 | Michaud et al. |
| 2020/0374137 | A1 | 11/2020 | Godfrey |
| 2020/0374145 | A1 | 11/2020 | Kau et al. |
| 2020/0389499 | A1 | 12/2020 | Koval et al. |
| 2020/0403809 | A1 | 12/2020 | Chan et al. |
| 2021/0034779 | A1 * | 2/2021 | Signorini .............. H04L 9/3239 |
| 2021/0126797 | A1 | 4/2021 | Peng |
| 2021/0136068 | A1 * | 5/2021 | Smeets ................... H04L 63/10 |
| 2021/0150205 | A1 | 5/2021 | Snyder et al. |
| 2021/0158309 | A1 | 5/2021 | McGinlay et al. |
| 2021/0174914 | A1 | 6/2021 | Cano et al. |
| 2021/0182539 | A1 | 6/2021 | Rassool |
| 2021/0208960 | A1 * | 7/2021 | Dande ................. G06F 21/6254 |
| 2021/0218720 | A1 | 7/2021 | Oberhauser et al. |
| 2021/0234672 | A1 | 7/2021 | Zeng et al. |
| 2021/0264520 | A1 | 8/2021 | Cummings |
| 2022/0051240 | A1 | 2/2022 | Shamai et al. |
| 2022/0051314 | A1 * | 2/2022 | Enkhtaivan ........... H04L 9/3218 |
| 2022/0052988 | A1 | 2/2022 | Gadnis et al. |
| 2022/0083936 | A1 * | 3/2022 | Balinsky ................ H04L 9/088 |
| 2022/0150077 | A1 | 5/2022 | Kim |
| 2022/0179378 | A1 | 6/2022 | Gourisetti et al. |
| 2022/0405750 | A1 | 12/2022 | Fallah et al. |
| 2022/0407856 | A1 | 12/2022 | Jawed |
| 2022/0414237 | A1 | 12/2022 | Lally et al. |
| 2022/0417331 | A1 | 12/2022 | Devine et al. |
| 2023/0006845 | A1 | 1/2023 | Leedom, Jr. |

FOREIGN PATENT DOCUMENTS

| | | | |
|---|---|---|---|
| WO | 2019086553 | A1 | 5/2019 |
| WO | 2019090264 | A1 | 5/2019 |
| WO | 2019090268 | A1 | 5/2019 |
| WO | 2019207297 | A1 | 10/2019 |

(56) References Cited

FOREIGN PATENT DOCUMENTS

WO          2020006121 A1      1/2020
WO          2021127577 A1      6/2021

OTHER PUBLICATIONS

U.S. Appl. No. 18/544,356, filed Dec. 18, 2023, Pending.
U.S. Appl. No. 18/239,061, filed Aug. 28, 2023, Allowed.
U.S. Appl. No. 18/236,361, filed Aug. 21, 2023, Pending.
U.S. Appl. No. 18/239,088, filed Aug. 28, 2023, Allowed.
U.S. Appl. No. 18/234,293, filed Aug. 15, 2023, Allowed.
UCLA Health, "UCLA-LedgerDomain: DSCSA Solution through Blockchain Technology: Drug Tracking, Tracing and Verification at the Last Mile of the Pharmaceutical Supply Cain with BRUINchain", PDG FDA Pilot Program Round Robin, Jul. 2020, in 160 pages.
Object Management Group Issues Request for Information for Disposable Self-Sovereign Identity Standard, Object Management Group (OMG), dated Jan. 21, 2021, 3 pages. Retrieved on Oct. 3, 2021. Retrieved from the internet [URL: https://www.omg.org/news/releases/pr2021/01-21-21.htm ].
Otto et. al., Verifiable Credentials Use Cases, W3C Working Group, dated Sep. 24, 2019, 35 pages. Retrieved on Oct. 3, 2021. Retrieved from the internet [URL: https://www.w3.org/TR/vc-use-cases/ ].
Partnership for DSCSA Governance, PDG, 2021, 3 pages. Retrieved on Oct. 3, 2021. Retrieved from the internet [URL: https://dscsagovernance.org/ ].
PharmaCompass, Top 1000 Global Pharmaceutical Companies, LePro PharmaCompass OPC, dated Sep. 2020, 101 pages. Retrieved on Oct. 6, 2021. Retrieved from the internet [URL: https://www.pharmacompass.com/data-compilation/top-1000-global-pharmaceutical-companies ].
Ponemon, What's New in the 2019 Cost of a Data Breach Report, Security Intelligence, dated Jul. 23, 2019, 10 pages. Retrieved on Oct. 2, 2021. Retrieved from the internet [URL: https://securityintelligence.com/posts/whats-new-in-the-2019-cost-of-a-data-breach-report/ ].
Prabha, P. et al., 2020, December. Securing telecare medical information system with blockchain technology. In 2020 2nd International Conference on Advances in Computing, Communication Control and Networking (ICACCCN) (pp. 846-851). IEEE. (Year: 2020), in 6 pages.
Rahman et al., Blockchain Based Mobile Edge Computing Framework for Secure Therapy Applications, 2018, IEEE Special Section on Mobile Multimedia for Healthcare, vol. 6, pp. 72469-72478 (Year: 2018).
Reed et. al., What are Decentralized Identifiers (DIDs)?, Evernym on Slideshare, dated Sep. 30, 2019, 29 pages. Retrieved on Oct. 3, 2021. Retrieved from the internet [URL: https://www.slideshare.net/Evernym/what-are-decentralized-identifiers-dids ].
Rose et. al., Zero Trust Architecture, NIST Special Publication 800-207, dated Aug. 2020, 59 pages. Retrieved on Oct. 6, 2021. Retrieved from the internet [URL: https://csrc.nist.gov/publications/detail/sp/800-207/final ].
Rossberg, WebAssembly Core Specification, W3C Working Group, W3C, dated Dec. 5, 2019, 164 pages. Retrieved on Oct. 5, 2021. Retrieved from the internet [URL: https://www.w3.org/TR/wasm-core-1/ ].
Searls, New Hope for Digital Identity, Linux Journal, dated Nov. 9, 2017, 7 pages. Retrieved on Oct. 4, 2021. Retrieved from the internet [URL: https://www.linuxjournal.com/content/new-hope-digital-identity ].
Shuaib et. al., Blockchains for Secure Digitized Medicine, Journal of Personalized Medicine, dated Jul. 13, 2019, 9(3): 35, 21 pages. Retrieved on Oct. 2, 2021. Retrieved from the internet [URL: https://www.mdpi.com/2075-4426/9/3/35 ].
Sovrin Governance Framework Working Group, Sovrin Governance Framework V2, Sovrin Foundation, dated Dec. 4, 2019, 20 pages. Retrieved on Oct. 5, 2021. Retrieved from the internet [URL: https://sovrin.org/wp-content/uploads/Sovrin-Governance-Framework-V2-Master-Document-V2.pdf ].
Sporny et. al., Verifiable Credentials Data Model 1.0, W3C Working Group. dated Nov. 19, 2019, 122 pages. Retrieved on Oct. 3, 2021. Retrieved from the internet [URL: https://www.w3.org/TR/vc-data-model/ ].
StClair et. al., Blockchain, Interoperability, and Self-Sovereign Identity: Trust Me, It's My Data, Blockchain in Healthcare Today, dated Jan. 6, 2020, 3 pages. Retrieved on Oct. 3, 2021. Retrieved from the internet [URL: https://blockchainhealthcaretoday.com/index.php/journal/article/view/122/144 ].
Steel, Passwords Are Still a Problem According to the 2019 Verizon Data Breach Investigations Report, LastPass Blog, dated May 21, 2019, 4 pages. Retrieved on Oct. 2, 2021. Retrieved from the internet [URL: https://blog.lastpass.com/2019/05/passwords-still-problem-according-2019-verizon-data-breach-investigations-report/ ].
Temoshok et. al., Developing Trust Frameworks to Support Identity Federations, National Institute of Standards and Technology (NIST), dated Jan. 2018, 34 pages. Retrieved on Oct. 4, 2021. Retrieved from the internet [URL: http://dx.doi.org/10.6028/NIST.IR.8149 ].
Thayer, "Why Does Mozilla Maintain Our Own Root Certificate Store?", Mozilla Security Blog, dated Feb. 14, 2019, 3 pages. Retrieved on Oct. 3, 2021. Retrieved from the internet [URL: https://blog.mozilla.org/security/2019/02/14/why-does-mozilla-maintain-our-own-root-certificate-store/ ].
The Commons project, Unlocking the full potential of technology and data for the common good, 2019-2021, 5 pages. Retrieved on Oct. 3, 2021. Retrieved from the internet [URL: https://thecommonsproject.org/commonpass ].
Tobin et. al., The Inevitable Rise of Self-Sovereign Identity, Sovrin Foundation Whitepaper, updated Mar. 28, 2017, 24 pages. Retrieved on Oct. 3, 2021. Retrieved from the internet [URL: https://sovrin.org/wp-content/uploads/2018/03/The-Inevitable-Rise-of-Self-Sovereign-Identity.pdf ].
U.S. Department of Health and Human Services Food and Drug Administration, Verification Systems Under the Frug Supply Chain Security Act for Certain Prescription Drugs, Guidance for Industry, Draft Guidance, dated Oct. 2018, 14 pages. Retrieved on Oct. 2, 2021. Retrieved from the internet [URL: https://www.fda.gov/media/117950/download ].
U.S. Department of Health and Human Services Food and Drug Administration, Wholesale Distributor Verification Requirement for Saleable Returned Drug Product and Dispenser Verification Requirements When Investigating a Suspect or Illegitimate Product—Compliance Policies, Guidance for Industry, dated Oct. 2020, 10 pages. Retrieved on Oct. 2, 2021. Retrieved from the internet [URL: https://www.fda.gov/media/131005/download ].
U.S. Department of Health and Human Services, Food and Drug Administration, Identifying Trading Partners Under the Drug Supply Chain Security Act, Guidance for Industry, dated Aug. 2017, 18 pages. Retrieved on Oct. 3, 2021. Retrieved from the internet [URL: https://www.fda.gov/files/drugs/published/Identifying-Trading-Partners-Under-the-Drug-Supply-Chain-Security-Act-Guidance-for-Industry.pdf ].
U.S. Food and Drug Administration, Drug Supply Chain Security Act Law and Policies, U.S. Department of Health and Human Services Food and Drug Administration, updated Oct. 23, 2020, 6 pages. Retrieved on Oct. 1, 2021. Retrieved from the internet [URL: https://www.fda.gov/drugs/drug-supply-chain-security-act-dscsa/drug-supply-chain-security-act-law-and-policies].
Untitled code sample, W3C Working Group, W3C, dated 2018, 7 pages. Retrieved on Oct. 6, 2021. Retrieved from the internet [URL: https://www.w3.org/2018/credentials/v1 ].
Web Assembly, Mozilla Developer Network (MDN), dated 2021, 31 pages. Retrieved on Oct. 5, 2021. Retrieved from the internet [URL: https://developer.mozilla.org/en-US/docs/WebAssembly ].
What are SMART Health Cards?, SMART Health Cards Framework, 2021, 4 pages. Retrieved on Oct. 3, 2021. Retrieved from the internet [URL: https://smarthealth.cards/ ].
XATP Working Group, Framework for extended ATP Authentication, Enhanced Verification and Saleable Returns Documentation,

(56)                    References Cited

OTHER PUBLICATIONS

LedgerDomain, dated Dec. 17, 2020, 25 pages. Retrieved on Oct. 1, 2021. Retrieved from the internet [URL: https://www.xatp.org/publications ].

Young, Verifiable Credentials Flavors Explained, COVID-19 Credentials Initiative, dated Feb. 2021, 21 pages. Retrieved on Oct. 3, 2021. Retrieved from the internet [URL: https://www.lfph.io/wp-content/uploads/2021/02/Verifiable-Credentials-Flavors-Explained.pdf ].

Grassi et. al., Digital Identity Guidelines: Federation and Assertions, NIST Special Publication 800-630, dated Jun. 2017, 49 pages. Retrieved on Oct. 6, 2021. Retrieved from the internet [URL: https://doi.org/10.6028/NIST.SP.800-63c ].

Abid et al., Block-Chain Security Advancement in Medical Sector for sharing Medical Records, 2019 International Conference on Innovative Computing (ICIC) (Year: 2019).

Androulaki et. al., Hyperledger Fabric: A distributed operating system for permissioned blockchains, Proceedings for EuroSys 2018 Conference, revised Apr. 17, 2018, 15 pages. Retrieved on Oct. 2, 2021. Retrieved from the internet [URL: https://arxiv.org/abs/1801.10228 ].

Ashkar et. al., Evaluation of Decentralized Verifiable Credentials to Authenticate Authorized Trading Partners and Verify Drug Provenance, Blockchain for Healthcare Today, dated Mar. 11, 2021, 14 pages. Retrieved on Oct. 3, 2021. Retrieved from the internet [URL: https://blockchainhealthcaretoday.com/index.php/journal/article/view/168 ].

Bogdanov, Pseudorandom Functions: Three Decades Later, dated 2017, 72 pages. Retrieved on Oct. 6, 2021. Retrieved from the internet [URL: https://eprint.iacr.org/2017/652.pdf].

Bossert, I Was the Homeland Security Adviser to Trump. We're Being Hacked., The New York Times, dated Dec. 16, 2020, 3 pages. Retrieved on Oct. 3, 2021. Retrieved from the internet [URL: https://www.nytimes.com/2020/12/16/opinion/fireeye-solarwinds-russia-hack.html ].

Bourque, Ditching passwords and increasing e-commerce conversion rates by 54%, CIO, dated May 1, 2017, 4 pages. Retrieved on Oct. 2, 2021. Retrieved from the internet [URL: https://www.cio.com/article/3193206/ditching-passwords-and-increasing-ecommerce-conversion-rates-by-54.html ].

Brook, "What's the Cost of a Data Breach in 2019?", Data Insider-Digital Guardian, dated Dec. 1, 2020, 8 pages. Retrieved on Oct. 2, 2021. Retrieved from the internet [URL: https://digitalguardian.com/blog/whats-cost-data-breach-2019 ].

Callahan et. al., Six Principles for Self-Sovereign Biometrics, Web of Trust Info., GitHub, dated Oct. 6, 2019,7 pages. Retrieved on Oct. 5, 2021. Retrieved from the internet [URL: https://github.com/WebOfTrustInfo/rwot6-santabarbara/blob/master/draft-documents/Biometrics.md].

Callahan, Council Post: Know Your Customer (KYC) Will be a Great Thing When It Works, Forbes, dated Jul. 10, 2018, 8 pages. Retrieved on Oct. 1, 2021. Retrieved from [URL: https://www.forbes.com/sites/forbestechcouncil/2018/07/10/know-your-customer-kyc-will-be-a-great-thing-when-it-works/?sh=722a21178dbb ].

Chadwick et. al., Verifiable Credentials Data Model 1.0: Expressing verifiable information on the Web, World Wide Web Consortium (W3C), dated Nov. 19, 2019, 68 pages. Retrieved on Oct. 1, 2021. Retrieved from the internet [URL: https://www.w3.org/TR/vc-data-model/ ].

Chien et. al., The Last Mile: DSCSA Solution Through Blockchain Technology: Drug Tracking, Tracing and Verification at the Last Mile of the Pharmaceutical Supply Chain with BRUINchain, Blockchain in Healthcare Today, dated Mar. 12, 2020, 28 pages. Retrieved on Oct. 2, 2021. Retrieved from the internet [URL: https://blockchainhealthcaretoday.com/index.php/journal/article/view/134 ].

COVID-19 Credentials Initiative, Hello World from the COVID-19 Credentials Initiative, dated Jun. 25, 2020, 3 pages. Retrieved on Oct. 3, 2021. Retrieved from the internet [URL: https://cci-2020.medium.com/hello-world-from-the-covid-19-credentials-initiative-6d45534c4b3a ].

DIF—Decentralized Identity Foundation, Homepage, dated 2021, 8 pages. Retrieved on Oct. 6, 2021. Retrieved from the internet [URL: https://identity.foundation/ ].

Dodds, Follow Your Nose, Linked Data Patterns, dated May 31, 2012, 2 pages. Retrieved on Oct. 3, 2021. Retrieved from the internet [URL: https://patterns.dataincubator.org/book/follow-your-nose.html ].

Drug Supply Chain Security Act (DSCSA), Food and Drug Administration (FDA), retrieved on Oct. 1, 2021, 3 pages. Retrieved from [URL: https://www.fda.gov/drugs/drug-supply-chain-integrity/drug-supply-chain-security-act-dscsa ].

DSCSA Pilot Project Program, Food and Drug Administration (FDA), updated May 22, 2019, 4 pages. Retrieved on Oct. 2, 2021. Retrieved from the internet [URL: https://www.fda.gov/drugs/drug-supply-chain-security-act-dscsa/dscsa-pilot-project-program ].

Entities, Spherity, 3 pages. Retrieved on Oct. 3, 2021. Retrieved from the internet [URL: https://docs.spherity.com/spherity-api/verifiable-credentials-api/entities ].

FDA's Technology Modernization Action Plan (TMAP), Food and Drug Administration (FDA), dated Sep. 18, 2019, 10 pages. Retrieved on Oct. 3, 2021. Retrieved from the internet [URL: https://www.fda.gov/media/130883/download].

Federal Trade Commission, Federal Law Requires All Businesses to Truncate Credit Card Information on Receipts, Federal Trade Commission (FTC), dated May 2007, 3 pages. Retrieved on Oct. 2, 2021. Retrieved from the internet [URL: https://www.ftc.gov/tips-advice/business-center/guidance/slip-showing-federal-law-requires-all-businesses-truncate ].

Freisleben, VRS Updates: Past, Present and Future, dated Dec. 12, 2018, Healthcare Distribution Alliance (HDA), 6 pages. Retrieved on Oct. 1, 2021. Retrieved from the internet [URL: https://www.hda.org/news/hda-blog/2018/12/07/14/44/2018-12-12-vrs-update-past-present-future ].

Gabay, Federal Controlled Substances Act: Ordering and Recordkeeping, Hospital Pharmacy, dated Dec. 9, 2013, 3 pages. Retrieved on Oct. 2, 2021. Retrieved from the internet [URL: https://www.ncbi.nlm.nih.gov/pmc/articles/PMC3875106/ ].

General Meeting Agenda—Healthcare SIG, Hyperledger Foundation, updated Feb. 17, 2021, 2 pages. Retrieved on Oct. 3, 2021. Retrieved from the internet [URL: https://wiki.hyperledger.org/display/HCSIG/2021.02.17+General+Meeting+Agenda ].

Google Protocol Buffers—Google's data interchange format, Github, dated 2008, 6 pages. Retrieved on Oct. 3, 2021. Retrieved from the internet [URL: https://github.com/protocolbuffers/protobuf ].

Grassi et. al., Digital Identity Guidelines, NIST Special Publication 800-63-3, dated Jun. 2017, 75 pages. Retrieved on Oct. 6, 2021. Retrieved from the internet [URL: https://doi.org/10.6028/NIST.SP.800-63-3 ].

Grassi et. al., Digital Identity Guidelines: Authentication and Lifecycle Management, NIST Special Publication 800-63B, dated Jun. 2017, 79 pages. Retrieved on Oct. 6, 2021. Retrieved from the internet [URL: https://doi.org/10.6028/NIST.SP.800-63b ].

GS1 Healthcare U.S. Standard 1.1—Applying the GS1 Lightweight Messaging Standard for DSCSA Verification of Returned Product Identifiers, dated Mar. 31, 2020, 60 pages. Retrieved on Oct. 1, 2021. Retrieved from the Internet [URL: https://www.gs1us.org/DesktopModules/Bring2mind/DMX/Download.aspx?Command=Core_Download&EntryId=1897&language=en-US&PortalId=0&TabId=134 ].

GS1 Healthcare U.S., Assessing Current Implementation of DSCSA Serialization Requirements, GS1 US, dated 2018, 6 pages. Retrieved on Oct. 2, 2021. Retrieved from the internet [URL: https://www.gs1us.org/DesktopModules/Bring2mind/DMX/Download.aspx?Command=Core_Download&EntryId=1210&language=en-US&PortalId=0&TabId=134 ].

GS1 Healthcare U.S., GS1 Lightweight Messaging Standard for Verification of Product Identifiers, dated Dec. 2018, 30 pages. Retrieved on Oct. 2, 2021. Retrieved from the internet [URL: https://www.gs1.org/docs/epc/GS1_Lightweight_Verification_Messaging_Standard.pdf ].

GS1 Healthcare U.S., Standard 1.2, Applying GS1 Standards for DSCSA and Traceability, dated Nov. 7, 2016, 126 pages. Retrieved on Oct. 2, 2021. Retrieved from the internet [URL: https://www.

(56)                     References Cited

OTHER PUBLICATIONS gs1us.org/DesktopModules/Bring2mind/DMX/Download.aspx? Command=Core_Download&EntryId=749&language=en-US &PortalId=0&TabId=134 ].

GS1 Standards Resources for DSCSA Implementation Support, GS1 US, dated Feb. 22, 2021, 7 pages. Retrieved on Oct. 3, 2021. Retrieved from the internet [URL: https://www.gs1us.org/industries/ healthcare/standards-in-use/pharmaceutical/dscsa-resources ].

GS1 U.S., DSCSA Pilot Project readiness results, PDG FDA Pilot Program Round—Robin Webinar Series, dated Jun. 30, 2020, slides 15-29. Retrieved on Oct. 2, 2021. Retreived from the internet [URL: : https://dscsagovernance org/wp-content/uploads/2020/08/ Attachment-A-Presentations.pdf ], in 160 pages.

Hammi, M.T.et al., Apr. 2018. "BCTrust: A decentralized authentication blockchain-based mechanism". In 2018 IEEE wireless communications and networking conference (WCNC) (pp. 1-6). IEEE. (Year: 2018), in 6 pages.

Hardman, Verifiable Data Registry (Image), Wikipedia, dated Nov. 5, 2019, 1 page. Retrieved on Oct. 6, 2021. Retrieved from the internet [URL: https://en.wikipedia.org/wiki/Verifiable_credentials#/ media/File:VC_triangle_of_Trust.svg ].

HDA Saleable Returns Pilot Study Identifies Two Recommendations to Meet 2019 DSCSA Requirements, Healthcare Distribution Alliance (HDA), dated Nov. 10, 2016, 5 pages. Retrieved on Oct. 3, 2021. Retrieved from the internet [URL: https://www.hda.org/news/ 2016-11-10-hda-pilot-results-revealed ].

Heath, SolarWinds hack was 'largest and most sophisticated attack' ever—Microsoft president, Financial Post, dated Feb. 14, 2021, 3 pages. Retrieved on Oct. 3, 2021. Retrieved from the internet [URL: https://financialpost.com/pmn/business-pmn/solarwinds-hack-was-largest-and-most-sophisticated-attack-ever-microsoft-president ].

Housley et. al., Trust Anchor Format, Internet Engineering Task Force (IETF), dated Jun. 2021, 14 pages. Retrieved on Oct. 3, 2021. Retrieved from the internet [URL: https://datatracker.ietf.org/doc/ html/rfc5914 ].

How to share an OpenPGP public key easily in three steps, Mailfence, dated Jul. 11, 2017, 14 pages. Retrieved on Aug. 13, 2021. Retrieved from the internet [URL: https://blog.mailfence.com/ openpgp-public-key/ ].

Hyperledger, Ursa, Github, updated 2021, 7 pages. Retrieved on Oct. 3, 2021. Retrieved from the internet [URL: https://github.com/ hyperledger/ursa ].

Identity-concept.svg, Wikimedia Commons, 3 pages. Retrieved on Oct. 6, 2021. Retrieved from the internet [URL: https://commons. wikimedia.org/wiki/File:Identity-concept.svg ].

Jurgens, Industry-wide DSCSA Compliance Pilot Successfully Completed, Spherity, dated Dec. 17, 2020, 15 pages. Retrieved on Oct. 1, 2021. Retrieved from the internet [URL: https://medium.com/ spherity/industry-wide-dscsa-compliance-pilot-successfully-completed-d7223a0f2c92 ].

Kaptjin et. al., X.509 Did method, WebOfTrustInfo, GitHub, dated Aug. 12, 2019, 6 pages. Retrieved on Oct. 5, 2021. Retrieved from the internet [URL: https://github.com/WebOfTrustInfo/rwot9-prague/ blob/master/topics-and-advance-readings/X.509-DID-Method.md ].

Keen et. al., Forecasts Worldwide Information Security Spending to Exceed $124 Billion in 2019, Gartner, dated Aug. 15, 2018, 5 pages. Retrieved on Oct. 2, 2021. Retrieved from the internet [URL: https://www.gartner.com/en/newsroom/press-releases/2018-08-15-gartner-forecasts-worldwide-information-security-spending-to-exceed-124-billion-in-2019 ].

Krebs, At Least 30,000 U.S. Organizations Newly Hacked Via Holes in Microsoft's Email, Krebson Security, dated Mar. 5, 2021, 6 pages. Retrieved on Oct. 3, 2021. Retrieved from the internet. [URL: https://krebsonsecurity.com/2021/03/at-least-30000-u-s-organizations-newly-hacked-via-holes-in-microsofts-email-software/ ].

Lodder et al., Sovrin DID Method Specification, Sovrin Foundation, dated Aug. 20, 2021, 16 pages. Retrieved on Oct. 3, 2021. Retrieved from the internet [URL: https://sovrin-foundation.github.io/sovrin/ spec/did-method-spec-template.html ].

Looker et. al., BBS+ Signatures 2020 Draft Community Group Report, W3C Community Group, dated Jun. 13, 2021, 31 pages. Retrieved on Oct. 3, 2021. Retrieved from the internet [URL: https://w3c-ccg.github.io/ldp-bbs2020/ ].

Lu, "How Much are Password Resets Costing Your Company?", Okta, dated Aug. 20, 2019, 2 pages. Retrieved on Oct. 2, 2021. Retrieved from the internet [URL: https://www.okta.com/blog/2019/ 08/how-much-are-password-resets-costing-your-company/ ].

Makaay et. al., Frameworks for Identity Systems, Open Identity Exchange (OIX), dated Jun. 2017, 18 pages. Retrieved on Oct. 5, 2021. Retrieved from the internet [URL: https://connectis.com/wp-content/uploads/2018/05/OIX-White-Paper_Trust-Frameworks-for-Identity-Systems_Final.pdf ].

Matney, Apple's global active install base of iPhones surpassed 900 million this quarter, TechCrunch, dated Jan. 29, 2019, 2 pages. Retrieved on Oct. 2, 2021. Retrieved from the internet [URL: https://techcrunch.com/2019/01/29/apples-global-active-install-base-of-iphones-surpassed-900-million-this-quarter/ ].

Mitre, Broad Coalition of Health and Technology Industry Leaders Announce Vaccination Credential Initiative to Accelerate Digital Access to COVID-19 Vaccination Records, dated Jan. 14, 2021, 5 pages. Retrieved on Oct. 3, 2021. Retrieved from the internet [URL: https://www.businesswire.com/news/home/20210114005294/en/ Broad-Coalition-of-Health-and-Technology-Industry-Leaders-Announce-Vaccination-Credential-Initiative-to-Accelerate-Digital-Access-to-COVID-19-Vaccination-Records ].

Newton, The battle inside Signal, The Verge, dated Jan. 25, 2021, 19 pages. Retrieved onRetrieved from the internet. [URL: https:// www.theverge.com/platform/amp/22249391/signal-app-abuse-messaging-employees-violence-misinformation ].

* cited by examiner

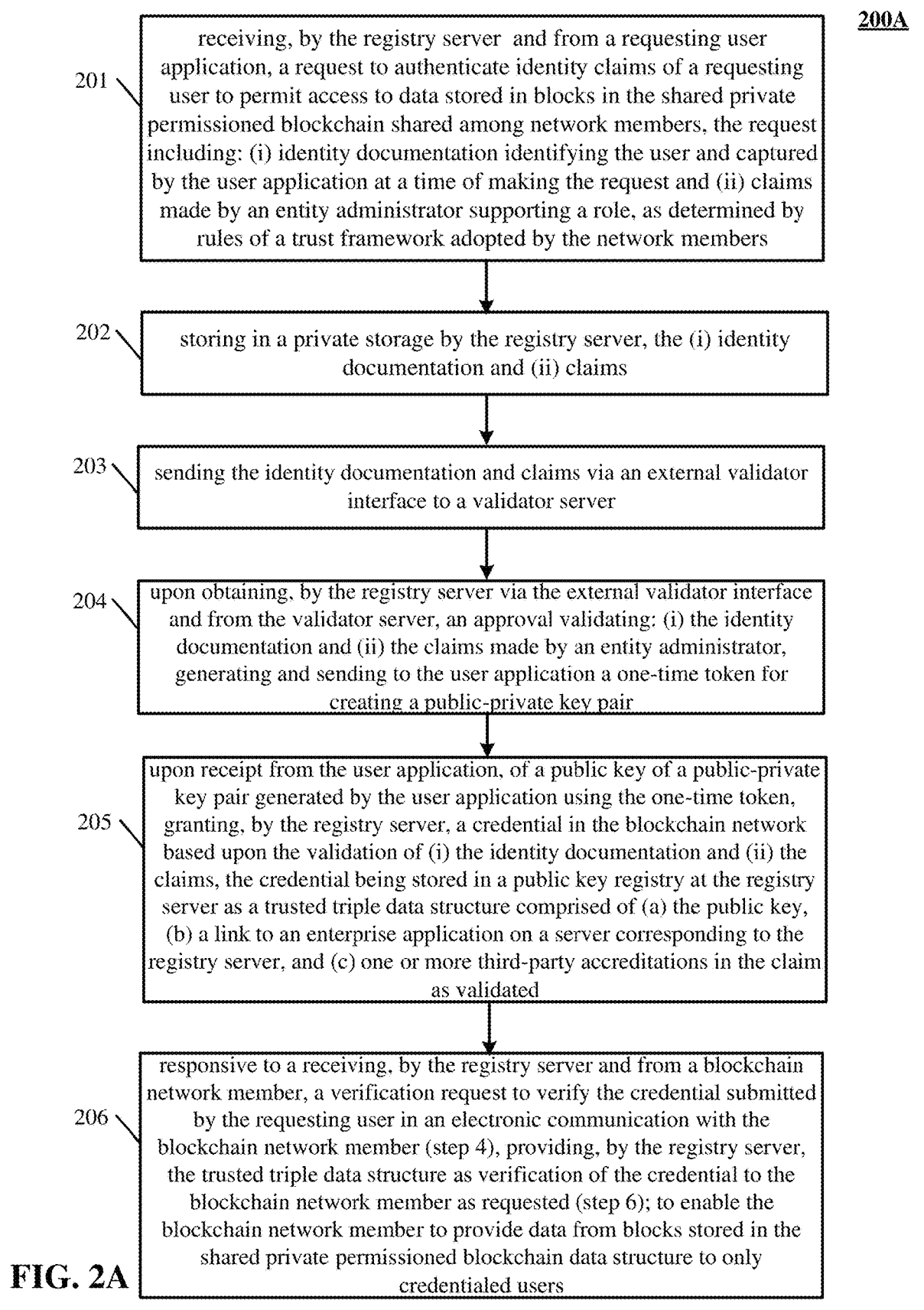

200A 201
receiving, by the registry server and from a requesting user application, a request to authenticate identity claims of a requesting user to permit access to data stored in blocks in the shared private permissioned blockchain shared among network members, the request including: (i) identity documentation identifying the user and captured by the user application at a time of making the request and (ii) claims made by an entity administrator supporting a role, as determined by rules of a trust framework adopted by the network members 202
storing in a private storage by the registry server, the (i) identity documentation and (ii) claims 203
sending the identity documentation and claims via an external validator interface to a validator server 204
upon obtaining, by the registry server via the external validator interface and from the validator server, an approval validating: (i) the identity documentation and (ii) the claims made by an entity administrator, generating and sending to the user application a one-time token for creating a public-private key pair 205
upon receipt from the user application, of a public key of a public-private key pair generated by the user application using the one-time token, granting, by the registry server, a credential in the blockchain network based upon the validation of (i) the identity documentation and (ii) the claims, the credential being stored in a public key registry at the registry server as a trusted triple data structure comprised of (a) the public key, (b) a link to an enterprise application on a server corresponding to the registry server, and (c) one or more third-party accreditations in the claim as validated 206
responsive to a receiving, by the registry server and from a blockchain network member, a verification request to verify the credential submitted by the requesting user in an electronic communication with the blockchain network member (step 4), providing, by the registry server, the trusted triple data structure as verification of the credential to the blockchain network member as requested (step 6); to enable the blockchain network member to provide data from blocks stored in the shared private permissioned blockchain data structure to only credentialed users

FIG. 2A

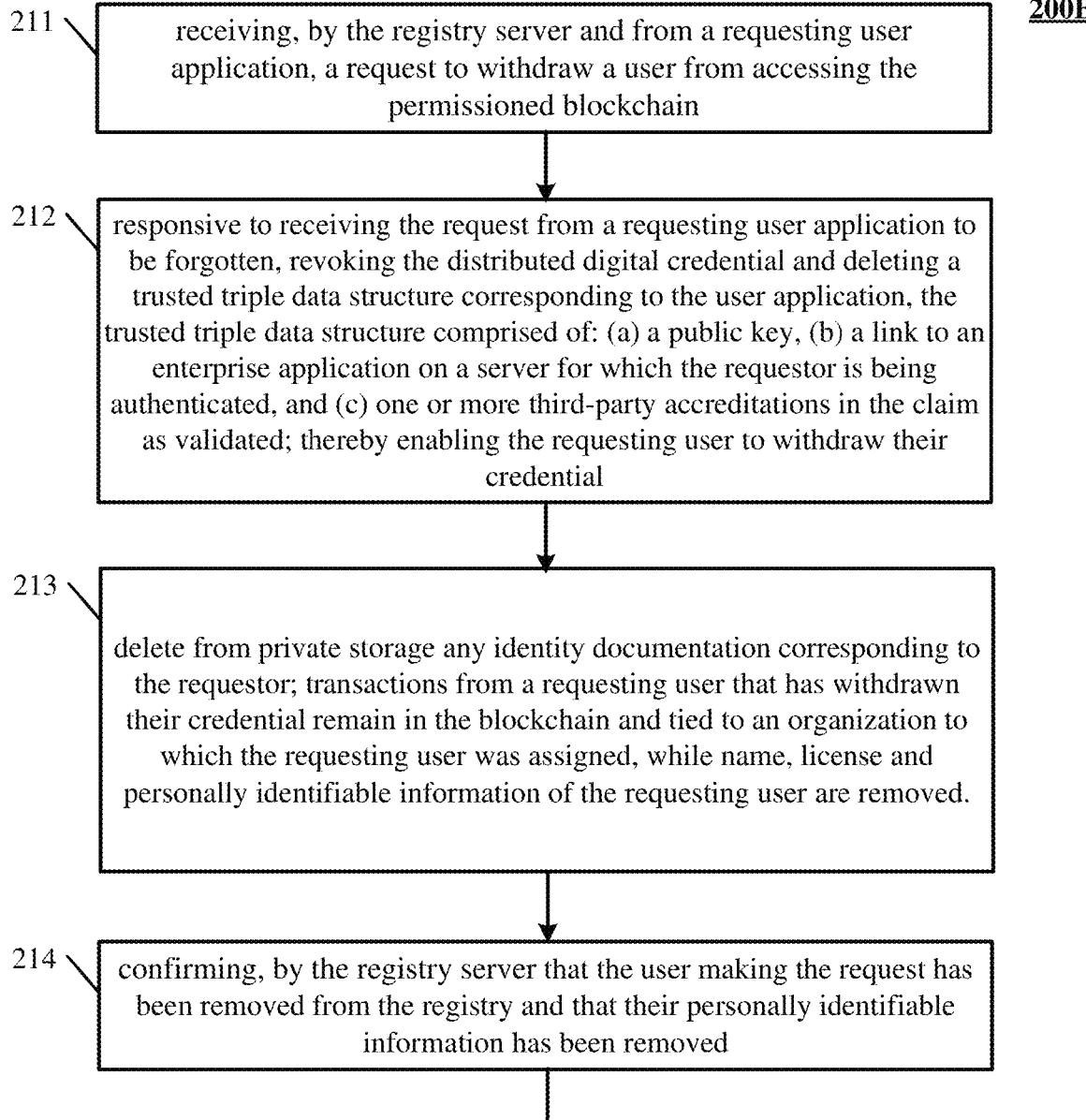

211 — receiving, by the registry server and from a requesting user application, a request to withdraw a user from accessing the permissioned blockchain 212 — responsive to receiving the request from a requesting user application to be forgotten, revoking the distributed digital credential and deleting a trusted triple data structure corresponding to the user application, the trusted triple data structure comprised of: (a) a public key, (b) a link to an enterprise application on a server for which the requestor is being authenticated, and (c) one or more third-party accreditations in the claim as validated; thereby enabling the requesting user to withdraw their credential 213 — delete from private storage any identity documentation corresponding to the requestor; transactions from a requesting user that has withdrawn their credential remain in the blockchain and tied to an organization to which the requesting user was assigned, while name, license and personally identifiable information of the requesting user are removed.

214 — confirming, by the registry server that the user making the request has been removed from the registry and that their personally identifiable information has been removed

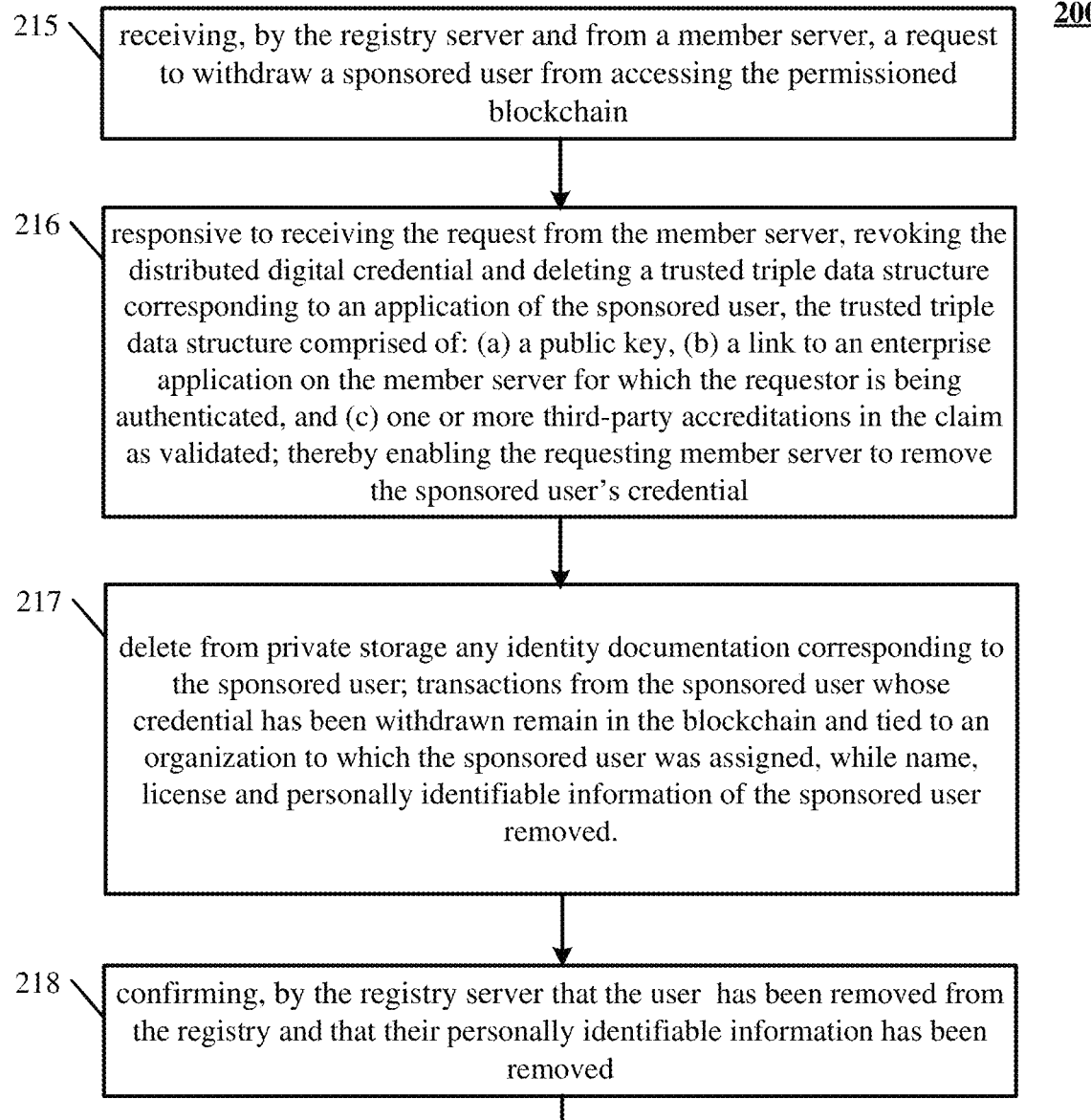

215 — receiving, by the registry server and from a member server, a request to withdraw a sponsored user from accessing the permissioned blockchain 216 — responsive to receiving the request from the member server, revoking the distributed digital credential and deleting a trusted triple data structure corresponding to an application of the sponsored user, the trusted triple data structure comprised of: (a) a public key, (b) a link to an enterprise application on the member server for which the requestor is being authenticated, and (c) one or more third-party accreditations in the claim as validated; thereby enabling the requesting member server to remove the sponsored user's credential 217 — delete from private storage any identity documentation corresponding to the sponsored user; transactions from the sponsored user whose credential has been withdrawn remain in the blockchain and tied to an organization to which the sponsored user was assigned, while name, license and personally identifiable information of the sponsored user removed.

218 — confirming, by the registry server that the user has been removed from the registry and that their personally identifiable information has been removed

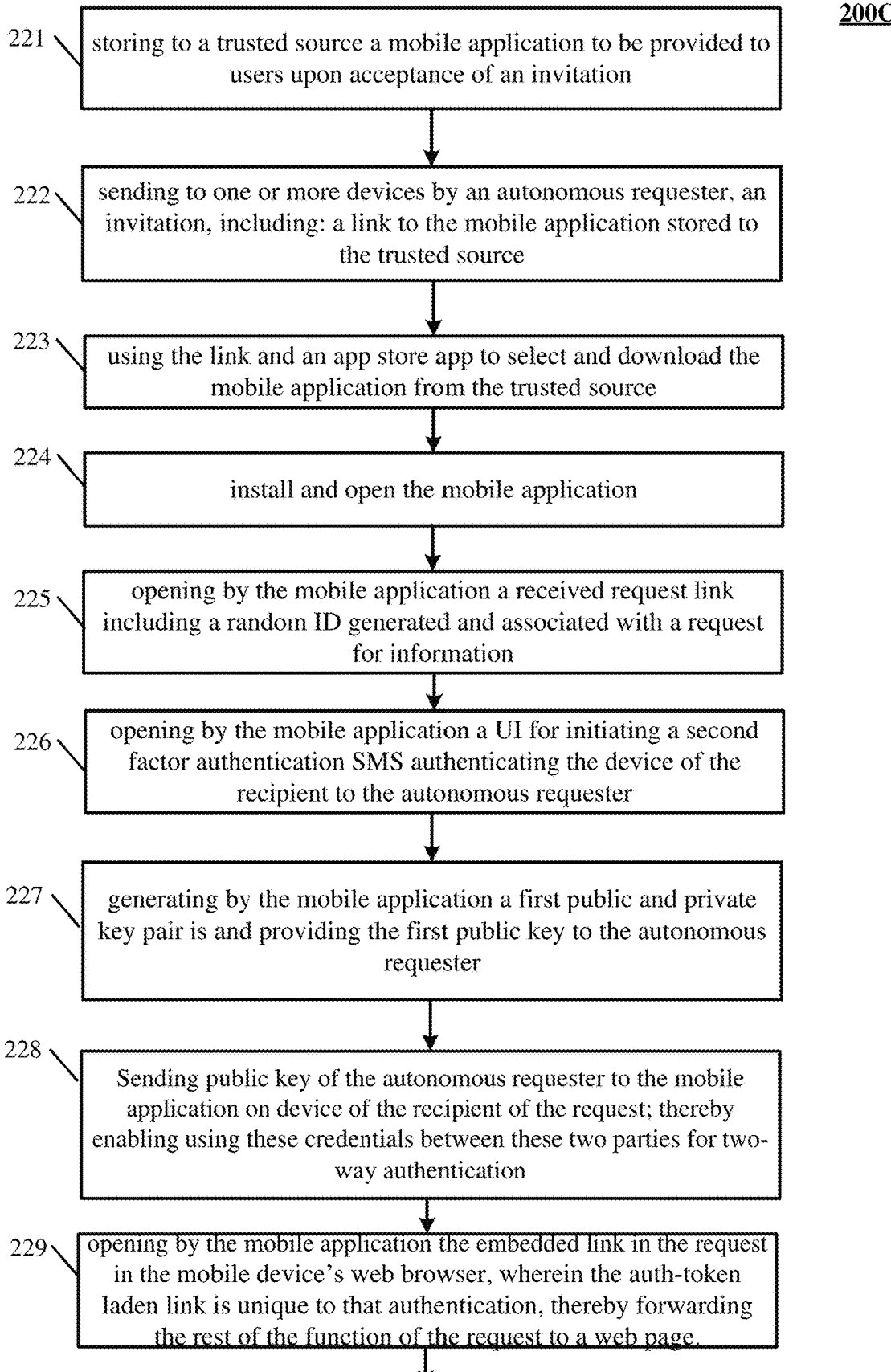

221 — storing to a trusted source a mobile application to be provided to users upon acceptance of an invitation 222 — sending to one or more devices by an autonomous requester, an invitation, including: a link to the mobile application stored to the trusted source 223 — using the link and an app store app to select and download the mobile application from the trusted source 224 — install and open the mobile application 225 — opening by the mobile application a received request link including a random ID generated and associated with a request for information 226 — opening by the mobile application a UI for initiating a second factor authentication SMS authenticating the device of the recipient to the autonomous requester 227 — generating by the mobile application a first public and private key pair is and providing the first public key to the autonomous requester 228 — Sending public key of the autonomous requester to the mobile application on device of the recipient of the request; thereby enabling using these credentials between these two parties for two-way authentication 229 — opening by the mobile application the embedded link in the request in the mobile device's web browser, wherein the auth-token laden link is unique to that authentication, thereby forwarding the rest of the function of the request to a web page.

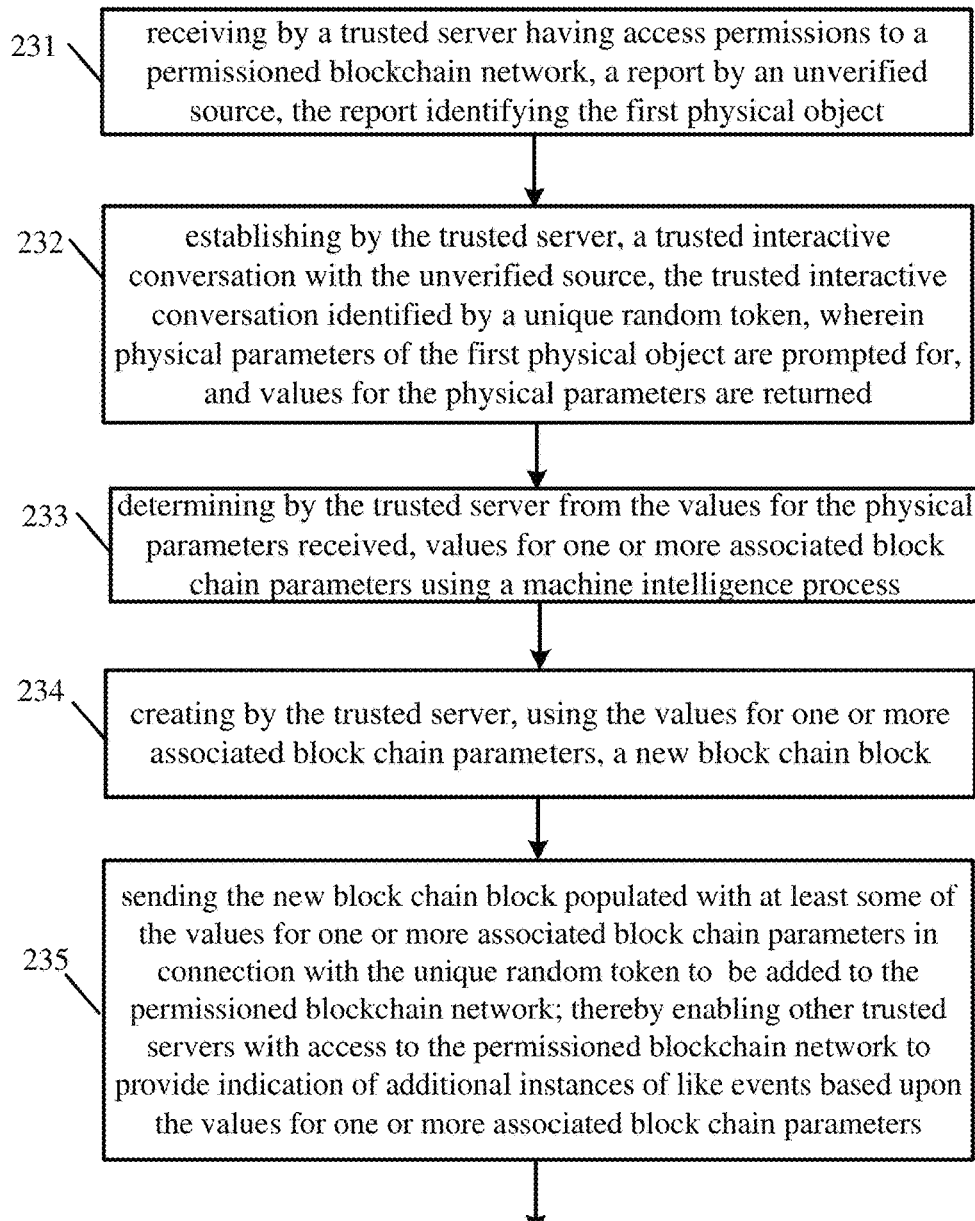

231 — receiving by a trusted server having access permissions to a permissioned blockchain network, a report by an unverified source, the report identifying the first physical object 232 — establishing by the trusted server, a trusted interactive conversation with the unverified source, the trusted interactive conversation identified by a unique random token, wherein physical parameters of the first physical object are prompted for, and values for the physical parameters are returned 233 — determining by the trusted server from the values for the physical parameters received, values for one or more associated block chain parameters using a machine intelligence process 234 — creating by the trusted server, using the values for one or more associated block chain parameters, a new block chain block 235 — sending the new block chain block populated with at least some of the values for one or more associated block chain parameters in connection with the unique random token to be added to the permissioned blockchain network; thereby enabling other trusted servers with access to the permissioned blockchain network to provide indication of additional instances of like events based upon the values for one or more associated block chain parameters

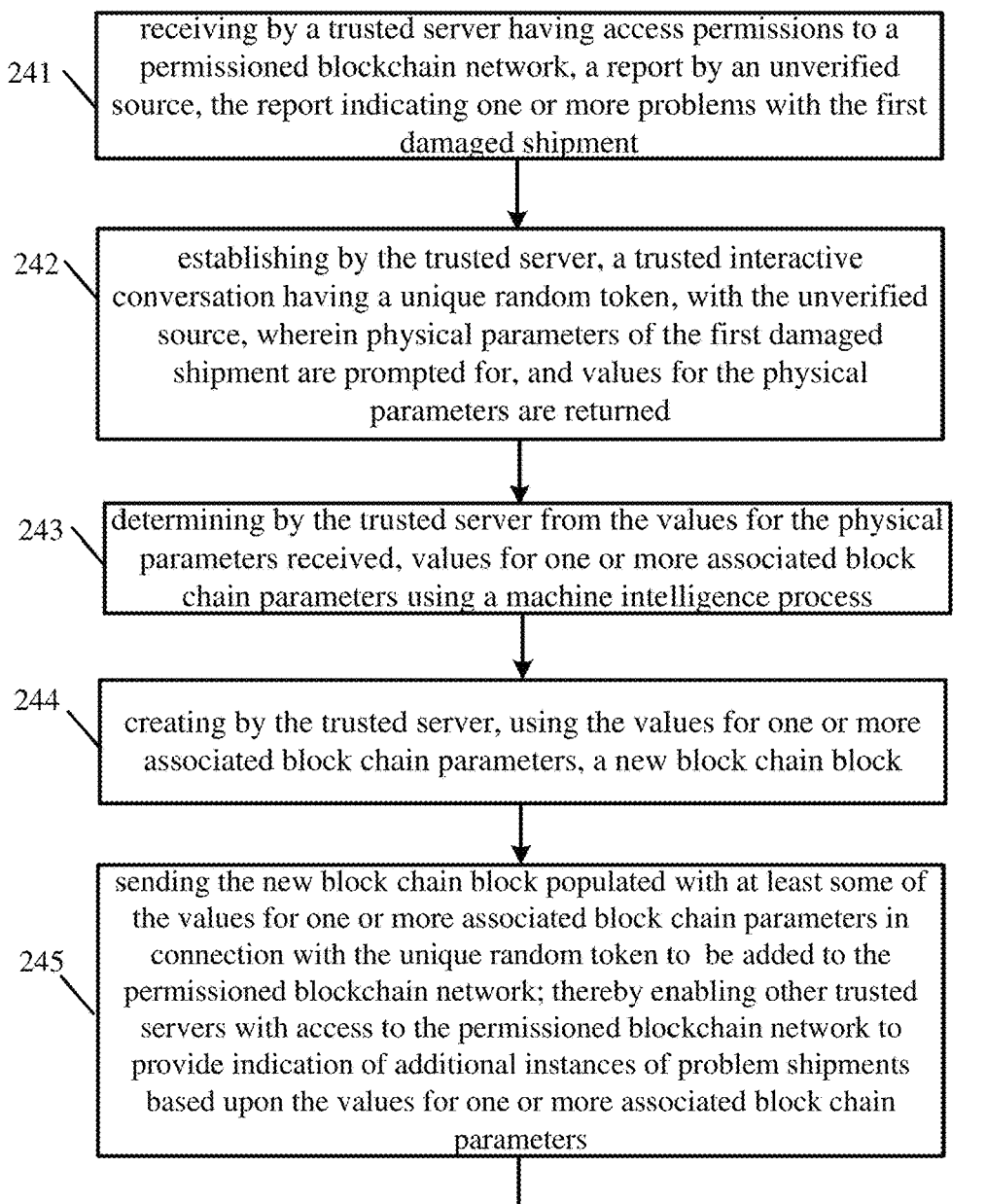

241 — receiving by a trusted server having access permissions to a permissioned blockchain network, a report by an unverified source, the report indicating one or more problems with the first damaged shipment 242 — establishing by the trusted server, a trusted interactive conversation having a unique random token, with the unverified source, wherein physical parameters of the first damaged shipment are prompted for, and values for the physical parameters are returned 243 — determining by the trusted server from the values for the physical parameters received, values for one or more associated block chain parameters using a machine intelligence process 244 — creating by the trusted server, using the values for one or more associated block chain parameters, a new block chain block 245 — sending the new block chain block populated with at least some of the values for one or more associated block chain parameters in connection with the unique random token to be added to the permissioned blockchain network; thereby enabling other trusted servers with access to the permissioned blockchain network to provide indication of additional instances of problem shipments based upon the values for one or more associated block chain parameters

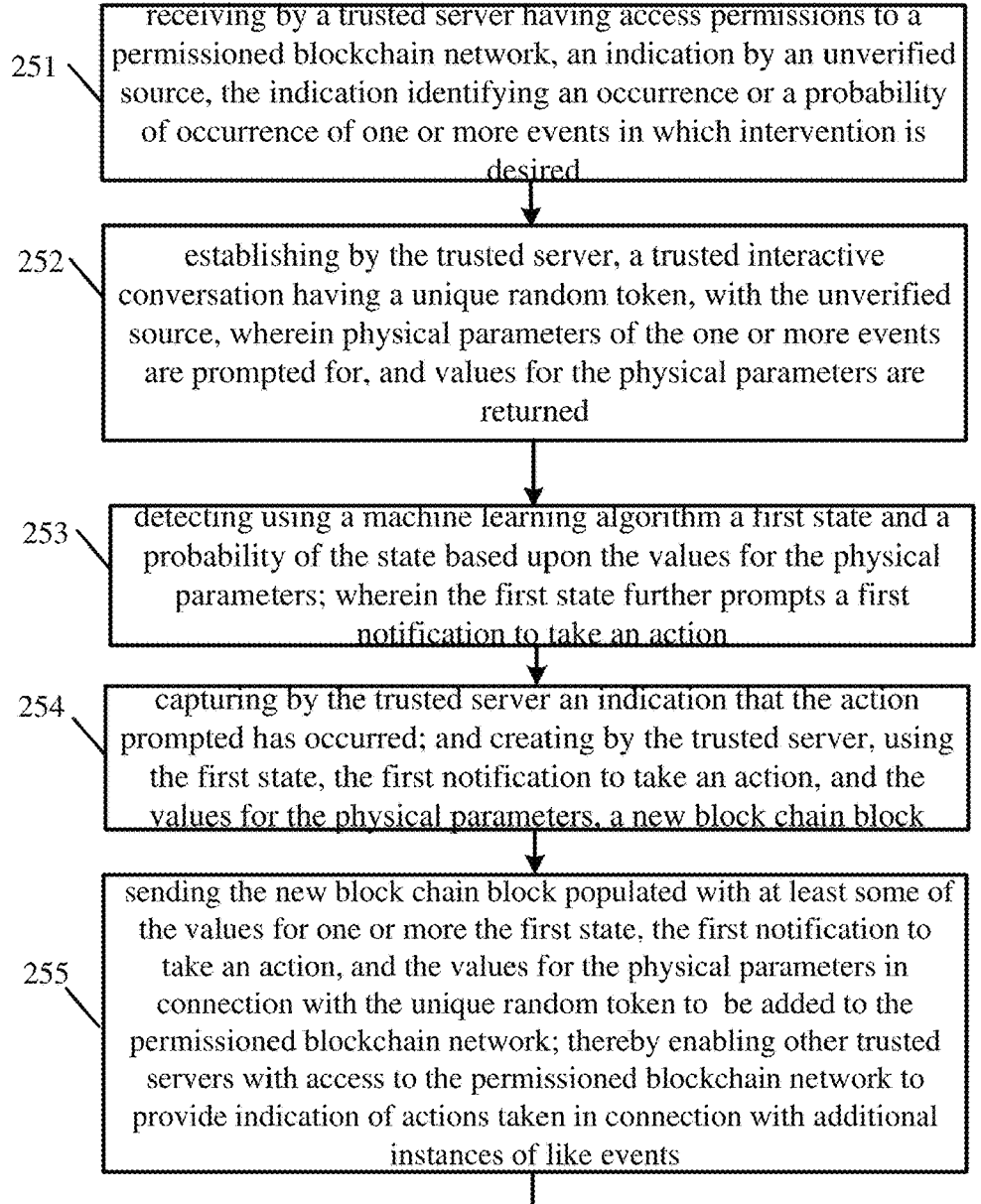

251  receiving by a trusted server having access permissions to a permissioned blockchain network, an indication by an unverified source, the indication identifying an occurrence or a probability of occurrence of one or more events in which intervention is desired 252  establishing by the trusted server, a trusted interactive conversation having a unique random token, with the unverified source, wherein physical parameters of the one or more events are prompted for, and values for the physical parameters are returned 253  detecting using a machine learning algorithm a first state and a probability of the state based upon the values for the physical parameters; wherein the first state further prompts a first notification to take an action 254  capturing by the trusted server an indication that the action prompted has occurred; and creating by the trusted server, using the first state, the first notification to take an action, and the values for the physical parameters, a new block chain block 255  sending the new block chain block populated with at least some of the values for one or more the first state, the first notification to take an action, and the values for the physical parameters in connection with the unique random token to be added to the permissioned blockchain network; thereby enabling other trusted servers with access to the permissioned blockchain network to provide indication of actions taken in connection with additional instances of like events

FIG. 2F

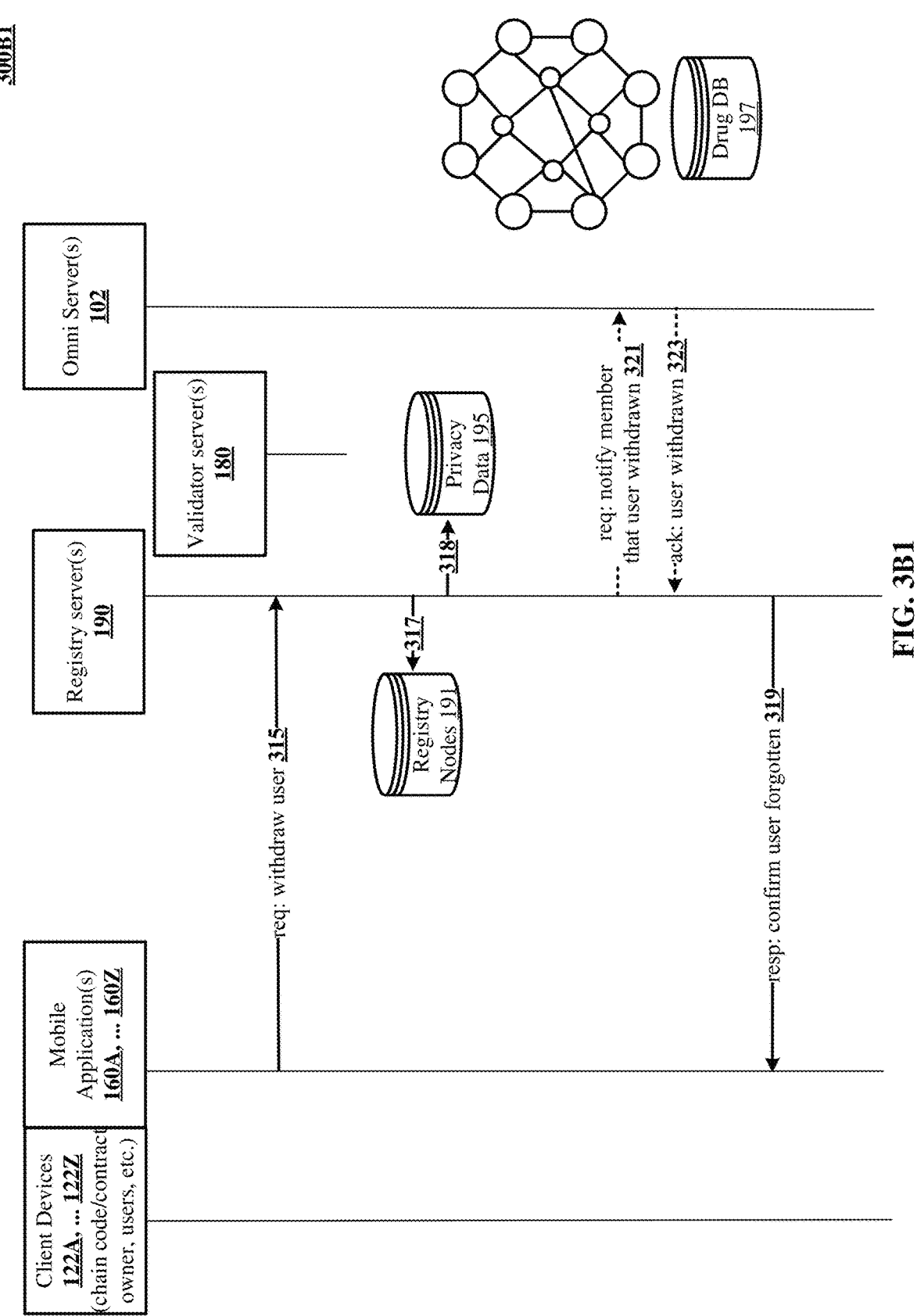
FIG. 3B1

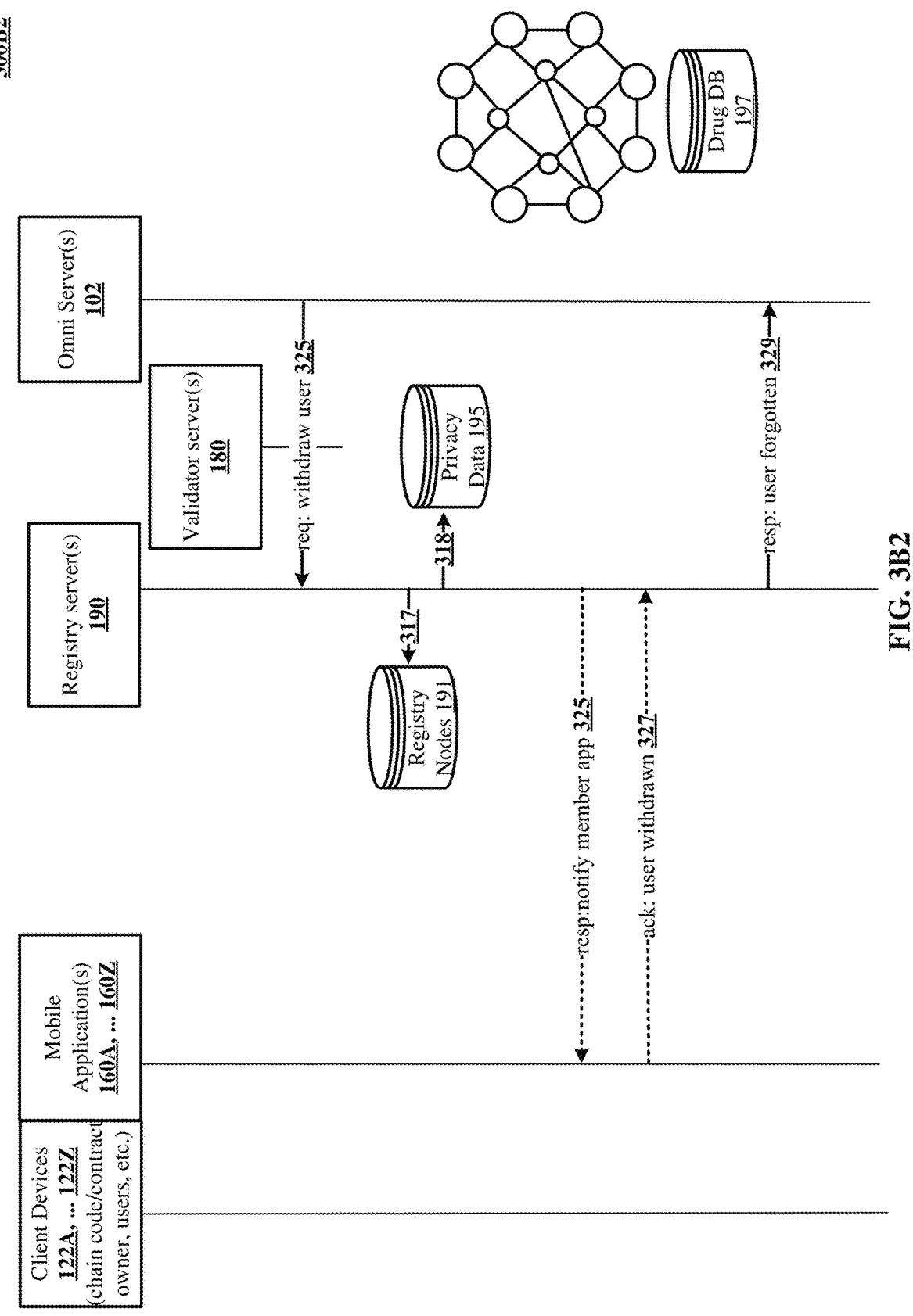
FIG. 3B2

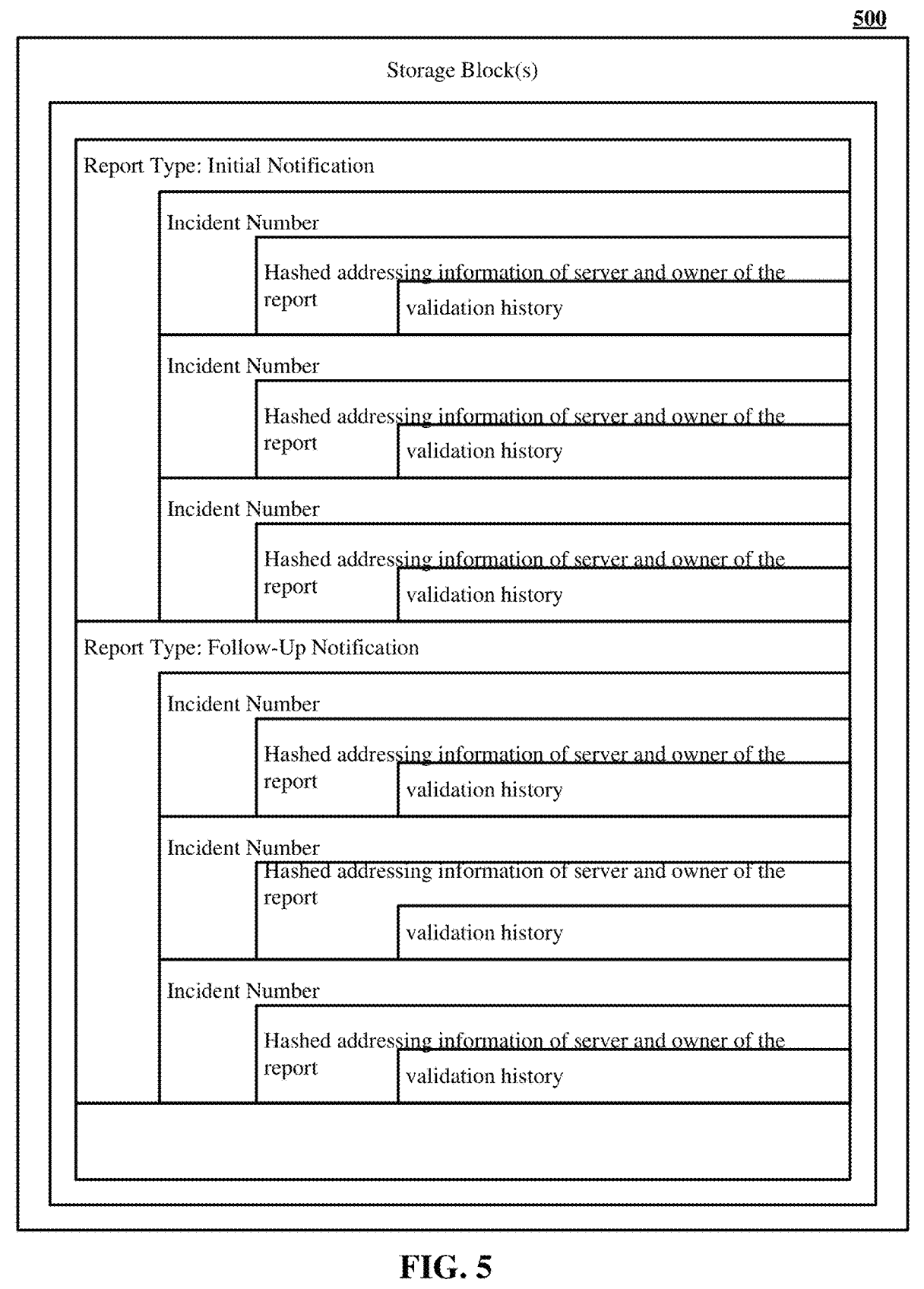

500

Storage Block(s)

Report Type: Initial Notification

Incident Number

Hashed addressing information of server and owner of the report validation history Incident Number Hashed addressing information of server and owner of the report validation history Incident Number Hashed addressing information of server and owner of the report validation history Report Type: Follow-Up Notification Incident Number Hashed addressing information of server and owner of the report validation history Incident Number Hashed addressing information of server and owner of the report validation history Incident Number Hashed addressing information of server and owner of the report validation history

FIG. 5

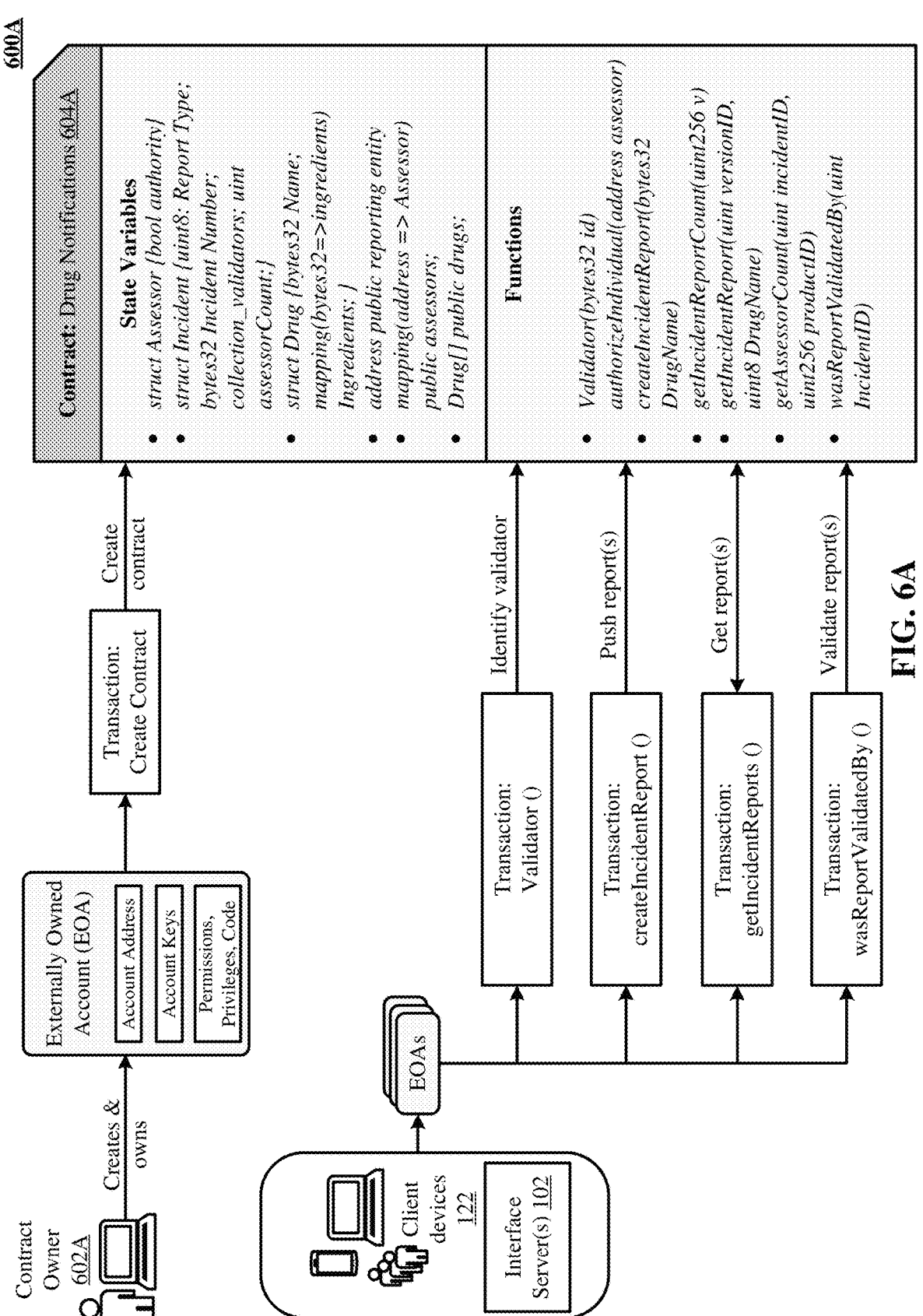

Contract: Drug Notifications 604A

State Variables

- struct Assessor {bool authority}
- struct Incident {uint8: Report Type; bytes32 Incident Number; collection_validators; uint assessorCount;}
- struct Drug {bytes32 Name; mapping(bytes32=>ingredients) Ingredients; }
- address public reporting entity
- mapping(address => Assessor) public assessors;
- Drug[] public drugs;

Functions

- Validator(bytes32 id)
- authorizeIndividual(address assessor)
- createIncidentReport(bytes32 DrugName)
- getIncidentReportCount(uint256 v)
- getIncidentReport(uint versionID, uint8 DrugName)
- getAssessorCount(uint incidentID, uint256 productID)
- wasReportValidatedBy(uint IncidentID)

Transaction: Create Contract

Create contract

Externally Owned Account (EOA)
- Account Address
- Account Keys
- Permissions, Privileges, Code Contract Owner 602A Creates & owns Transaction: Validator ()

Identify validator

Transaction: createIncidentReport ()

Push report(s)

Transaction: getIncidentReports ()

Get report(s)

Transaction: wasReportValidatedBy ()

Validate report(s)

EOAs

Client devices 122

Interface Server(s) 102

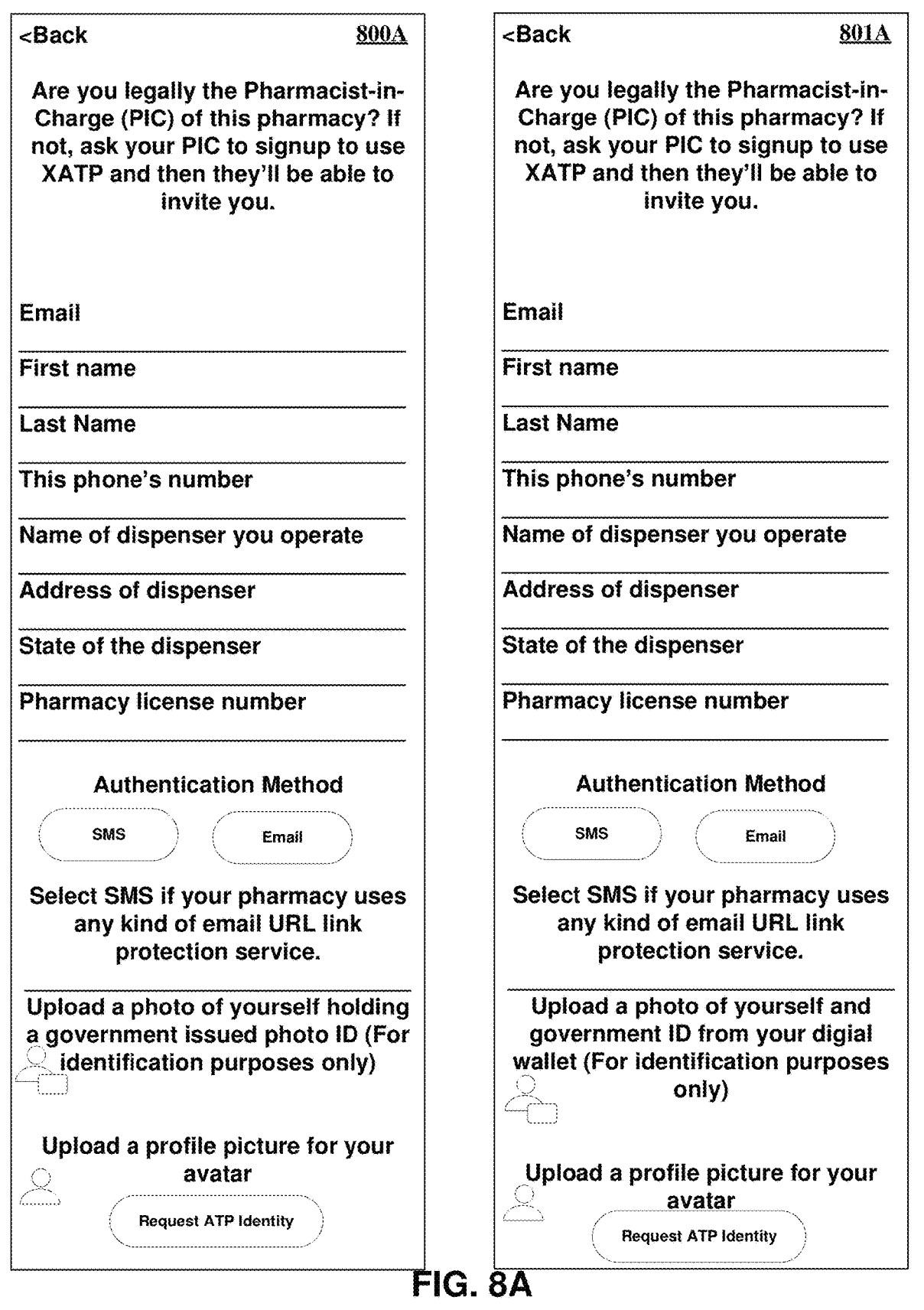

<Back                                    800A

Are you legally the Pharmacist-in-
Charge (PIC) of this pharmacy? If
not, ask your PIC to signup to use
XATP and then they'll be able to
invite you.

Email
_____

First name
_____

Last Name
_____

This phone's number
_____

Name of dispenser you operate
_____

Address of dispenser
_____

State of the dispenser
_____

Pharmacy license number
_____

Authentication Method ( SMS )          ( Email )

Select SMS if your pharmacy uses
any kind of email URL link
protection service.

Upload a photo of yourself holding
a government issued photo ID (For
identification purposes only)

Upload a profile picture for your
avatar ( Request ATP Identity )

---

<Back                                    801A

Are you legally the Pharmacist-in-
Charge (PIC) of this pharmacy? If
not, ask your PIC to signup to use
XATP and then they'll be able to
invite you.

Email
_____

First name
_____

Last Name
_____

This phone's number
_____

Name of dispenser you operate
_____

Address of dispenser
_____

State of the dispenser
_____

Pharmacy license number
_____

Authentication Method ( SMS )          ( Email )

Select SMS if your pharmacy uses
any kind of email URL link
protection service.

Upload a photo of yourself and
government ID from your digial
wallet (For identification purposes
only)

Upload a profile picture for your
avatar ( Request ATP Identity )

FIG. 8A

800C

Joe Bag O'Code   has applied for an XATP Digital ID!

Joe Bag O'Code   has applied for an XATP Digital ID!

Please review the following application and click the APPROVE button below to verify their identity as the Pharmacist in Charge. If you have any questions or concerns, please contact admin@xatp.org.

Name: Joe Bag O'Code
Email: JBOC@anymail.com
Phone: 123-456-7890
Dispenser Name: Any Pharmacy
Dispenser Address: 123 Main Street
License No.: 12345

*Profile picture (will be visible to other users; full sized version here)*

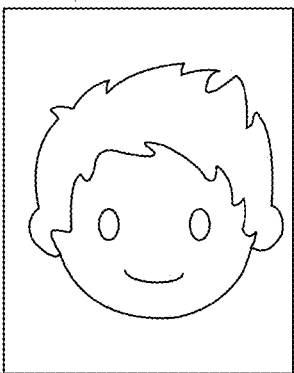

*License picture (will not be shared with anyone else; full sized version here)*

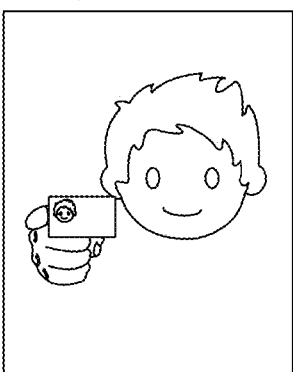

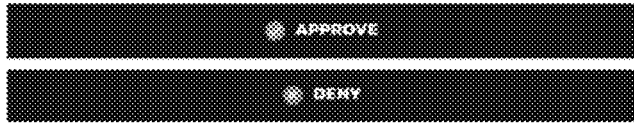

XATP is a tool designed for pharmacists to make drug verification under the US Drug Supply Chain Security Act (DSCSA) faster, easier, and more secure. This is not an advertisement. If you have any questions, or received this message in error, please contact admin@xatp.org.

By clicking the APPROVE button, you verify that the applicant is the Pharmacist in Charge (PIC) at the dispenser identified above. If the information above is incorrect or incomplete, click DENY to reject the application. (The applicant will have the option to re-apply.) These links will expire in 7 days.

Learn more at xatp.org.

 XATP          FIG. 8C

800D

Joe Bag O'Code   has applied for an XATP Digital ID!

Joe Bag O'Code   has applied for an XATP Digital ID!

Please review the following application and click the APPROVE button below to verify their identity as the Pharmacist in Charge. If you have any questions or concerns, please contact admin@xatp.org.

Name: Joe Bag O'Code
Email: JBOC@anymail.com
Phone: 123-456-7890
Dispenser Name: Any Pharmacy
Dispenser Address: 123 Main Street
License No.: 12345

*Profile picture (will be visible to other users; full-sized version here)*

*License picture (will not be shared with anyone else; full-sized version here)*

APPROVE

DENY

XATP is a tool designed for pharmacists to make drug verification under the US Drug Supply Chain Security Act (DSCSA) faster, easier, and more secure. This is not an advertisement. If you have any questions, or received this message in error, please contact admin@xatp.org.

By clicking the APPROVE button, you verify that the applicant is the Pharmacist in Charge (PIC) at the dispenser identified above. If the information above is incorrect or incomplete, click DENY to reject the application. (The applicant will have the option to re-apply.) These links will expire in 7 days.

Learn more at xatp.org.

 XATP

BOARD OF PHARMACY

LICENSING DETAILS FOR: PHE 12345
Name: Any Pharmacy
License Type: Pharmacy (Government owned community)
License Status: Clear LICENSING RELATIONSHIPS
Name: Bag O'Code, Joseph
License/Registration Type: Registered Pharmacist
License Number: 1234 Primary Status: Clear

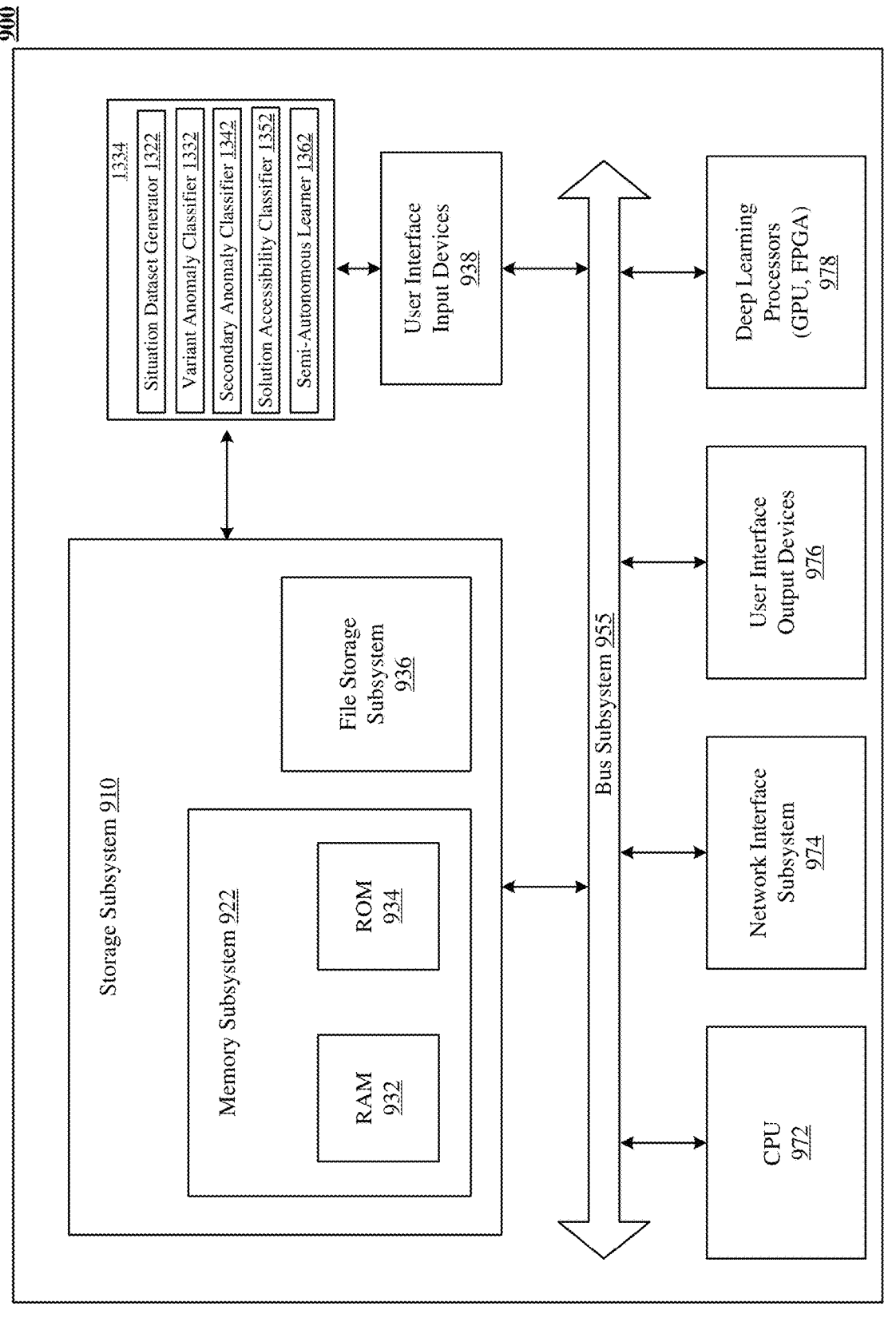
FIG. 9 – Computer System

Convolutional Neural Network

Figure 11:
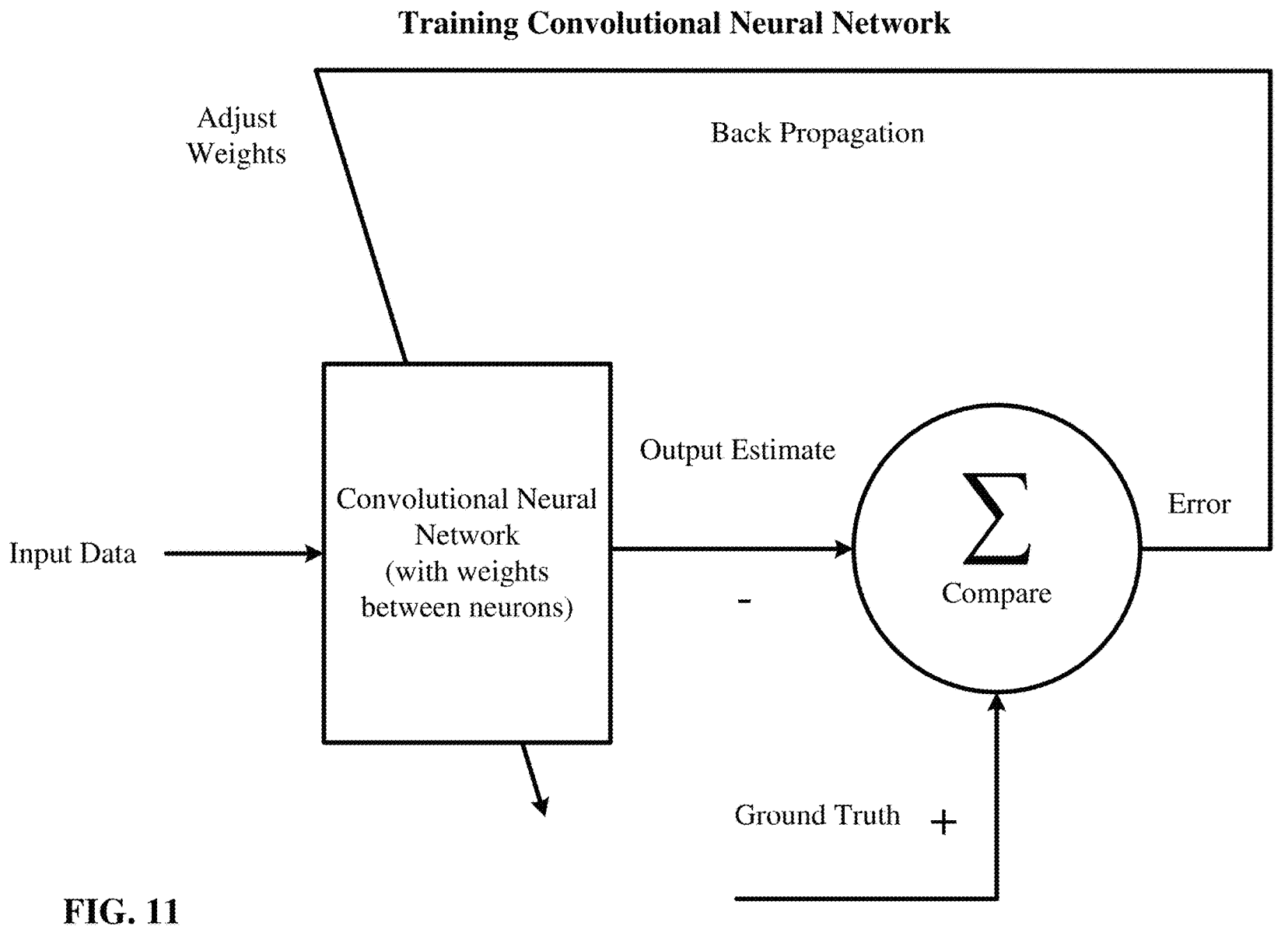

Training Convolutional Neural Network

Back Propagation

Adjust Weights

Error

Compare

Output Estimate

Ground Truth

Convolutional Neural Network (with weights between neurons)

Input Data

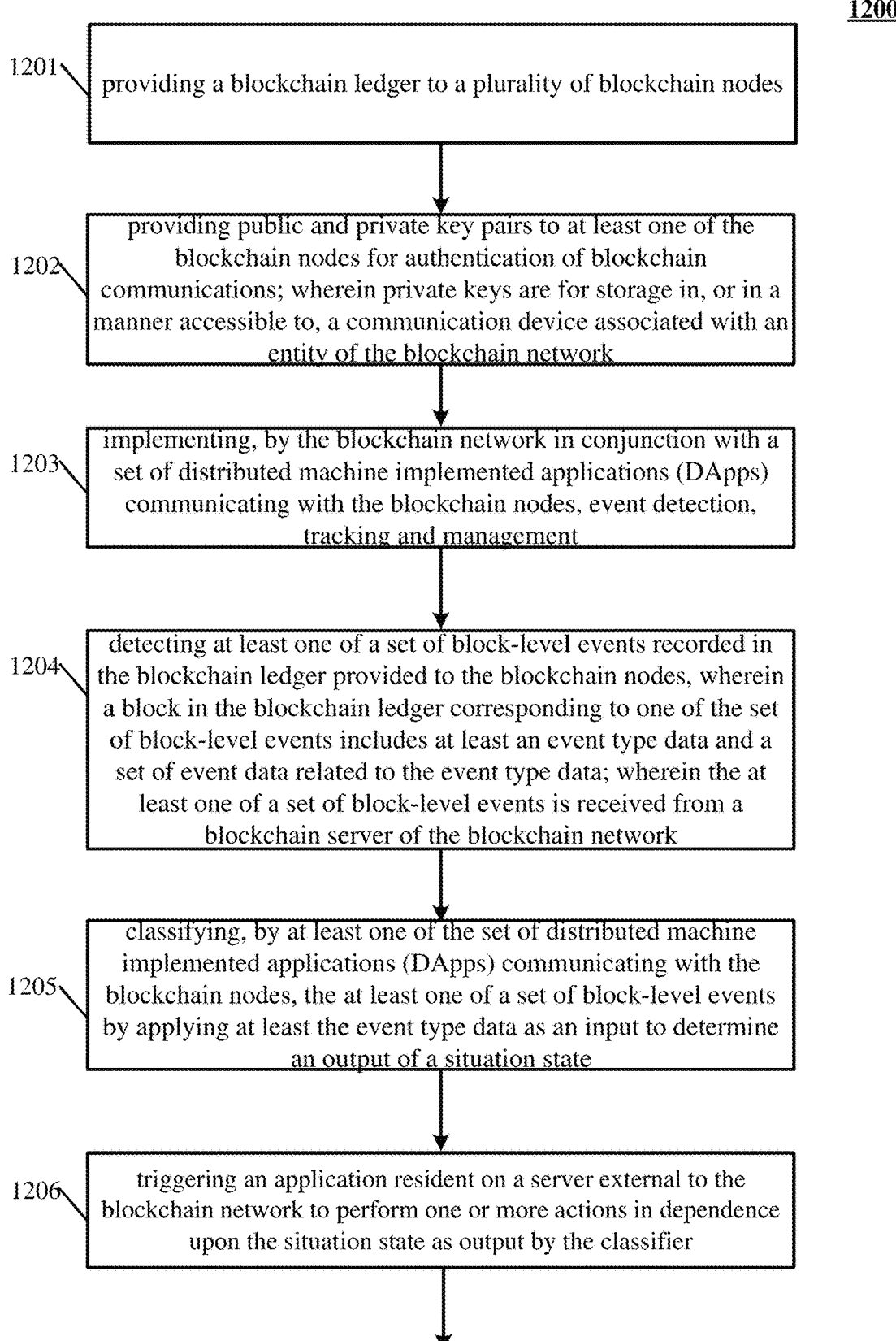

1201 — providing a blockchain ledger to a plurality of blockchain nodes

1202 — providing public and private key pairs to at least one of the blockchain nodes for authentication of blockchain communications; wherein private keys are for storage in, or in a manner accessible to, a communication device associated with an entity of the blockchain network 1203 — implementing, by the blockchain network in conjunction with a set of distributed machine implemented applications (DApps) communicating with the blockchain nodes, event detection, tracking and management 1204 — detecting at least one of a set of block-level events recorded in the blockchain ledger provided to the blockchain nodes, wherein a block in the blockchain ledger corresponding to one of the set of block-level events includes at least an event type data and a set of event data related to the event type data; wherein the at least one of a set of block-level events is received from a blockchain server of the blockchain network 1205 — classifying, by at least one of the set of distributed machine implemented applications (DApps) communicating with the blockchain nodes, the at least one of a set of block-level events by applying at least the event type data as an input to determine an output of a situation state 1206 — triggering an application resident on a server external to the blockchain network to perform one or more actions in dependence upon the situation state as output by the classifier

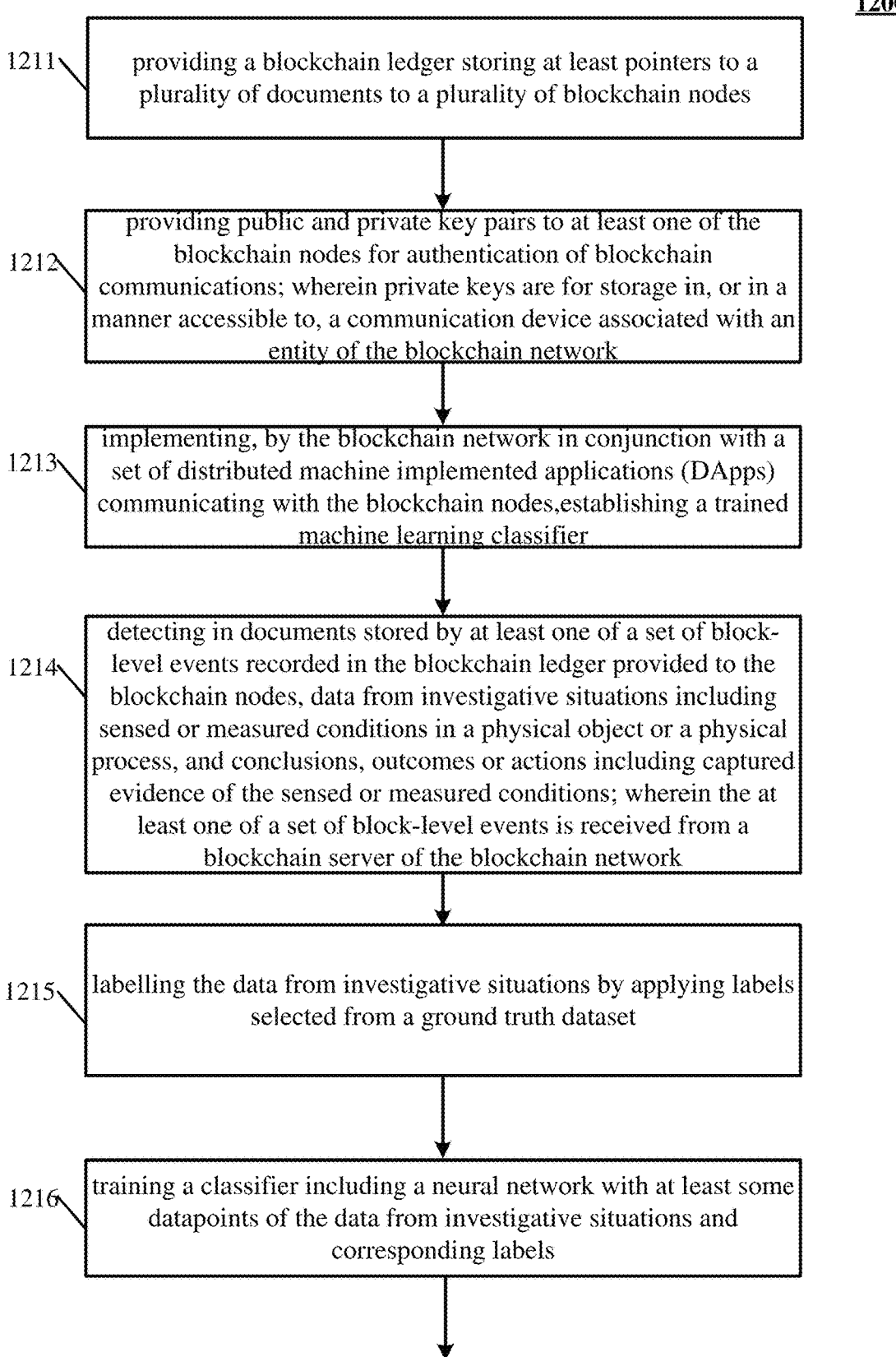

1211 — providing a blockchain ledger storing at least pointers to a plurality of documents to a plurality of blockchain nodes 1212 — providing public and private key pairs to at least one of the blockchain nodes for authentication of blockchain communications; wherein private keys are for storage in, or in a manner accessible to, a communication device associated with an entity of the blockchain network 1213 — implementing, by the blockchain network in conjunction with a set of distributed machine implemented applications (DApps) communicating with the blockchain nodes,establishing a trained machine learning classifier 1214 — detecting in documents stored by at least one of a set of block-level events recorded in the blockchain ledger provided to the blockchain nodes, data from investigative situations including sensed or measured conditions in a physical object or a physical process, and conclusions, outcomes or actions including captured evidence of the sensed or measured conditions; wherein the at least one of a set of block-level events is received from a blockchain server of the blockchain network 1215 — labelling the data from investigative situations by applying labels selected from a ground truth dataset 1216 — training a classifier including a neural network with at least some datapoints of the data from investigative situations and corresponding labels

FIG. 12B

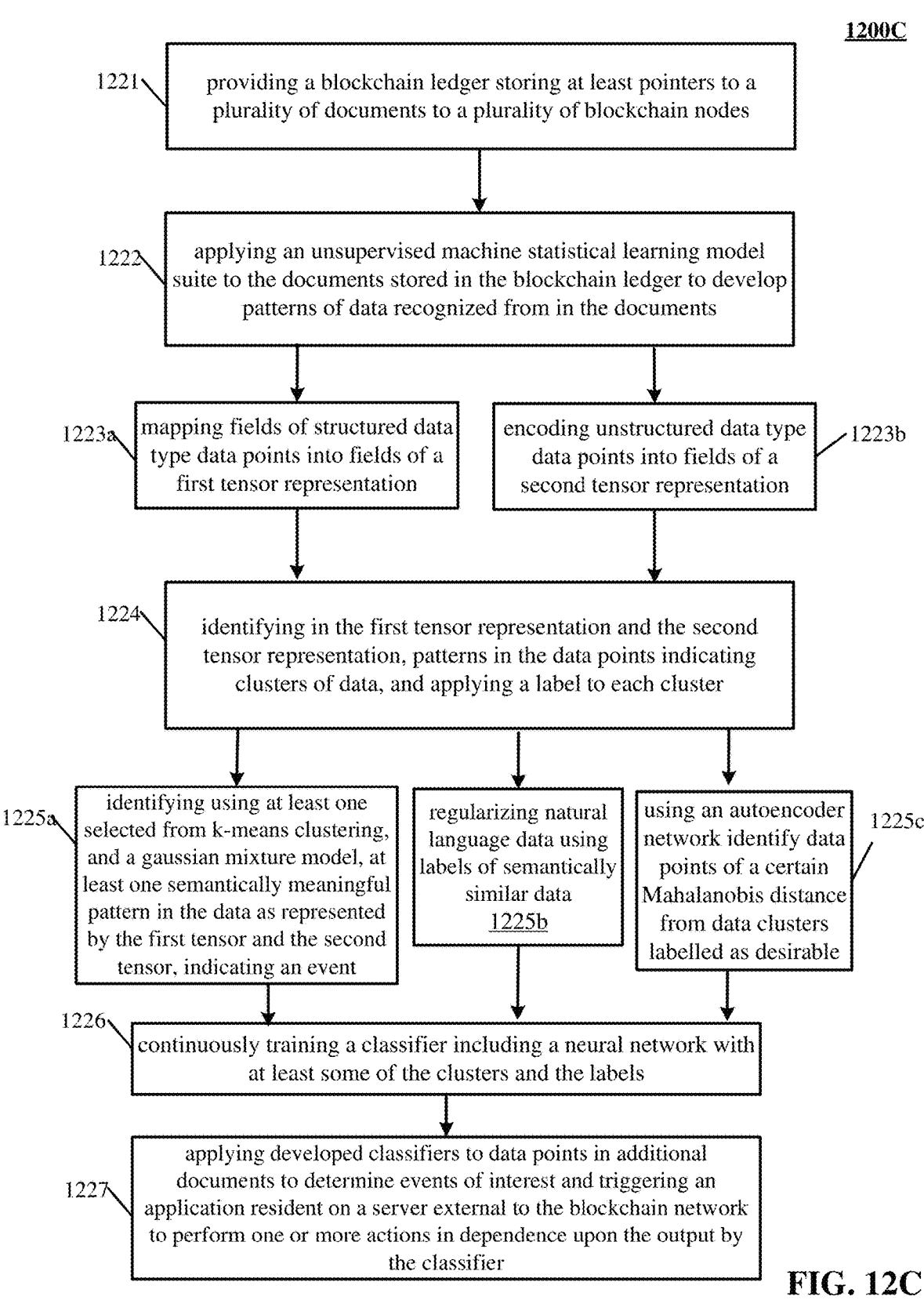

1200C

1221 — providing a blockchain ledger storing at least pointers to a plurality of documents to a plurality of blockchain nodes 1222 — applying an unsupervised machine statistical learning model suite to the documents stored in the blockchain ledger to develop patterns of data recognized from in the documents 1223a — mapping fields of structured data type data points into fields of a first tensor representation 1223b — encoding unstructured data type data points into fields of a second tensor representation 1224 — identifying in the first tensor representation and the second tensor representation, patterns in the data points indicating clusters of data, and applying a label to each cluster 1225a — identifying using at least one selected from k-means clustering, and a gaussian mixture model, at least one semantically meaningful pattern in the data as represented by the first tensor and the second tensor, indicating an event 1225b — regularizing natural language data using labels of semantically similar data 1225c — using an autoencoder network identify data points of a certain Mahalanobis distance from data clusters labelled as desirable 1226 — continuously training a classifier including a neural network with at least some of the clusters and the labels 1227 — applying developed classifiers to data points in additional documents to determine events of interest and triggering an application resident on a server external to the blockchain network to perform one or more actions in dependence upon the output by the classifier

FIG. 12C

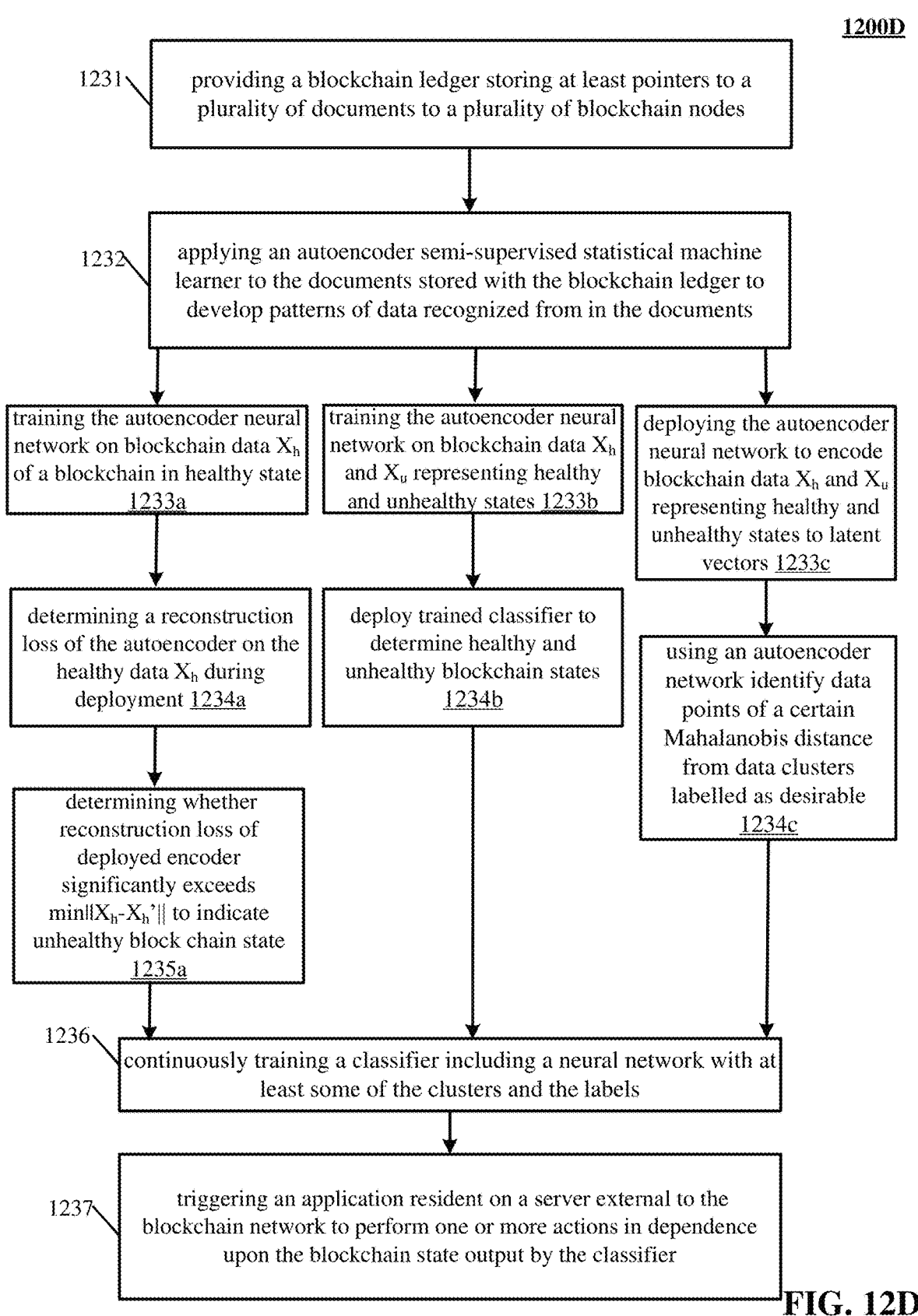

1200D

1231 — providing a blockchain ledger storing at least pointers to a plurality of documents to a plurality of blockchain nodes 1232 — applying an autoencoder semi-supervised statistical machine learner to the documents stored with the blockchain ledger to develop patterns of data recognized from in the documents training the autoencoder neural network on blockchain data $X_h$ of a blockchain in healthy state 1233a training the autoencoder neural network on blockchain data $X_h$ and $X_u$ representing healthy and unhealthy states 1233b deploying the autoencoder neural network to encode blockchain data $X_h$ and $X_u$ representing healthy and unhealthy states to latent vectors 1233c determining a reconstruction loss of the autoencoder on the healthy data $X_h$ during deployment 1234a deploy trained classifier to determine healthy and unhealthy blockchain states 1234b using an autoencoder network identify data points of a certain Mahalanobis distance from data clusters labelled as desirable 1234c determining whether reconstruction loss of deployed encoder significantly exceeds min$\|X_h-X_h'\|$ to indicate unhealthy block chain state 1235a 1236 — continuously training a classifier including a neural network with at least some of the clusters and the labels 1237 — triggering an application resident on a server external to the blockchain network to perform one or more actions in dependence upon the blockchain state output by the classifier

DECENTRALIZED IDENTITY AUTHENTICATION FRAMEWORK FOR DISTRIBUTED DATA

RELATED APPLICATION

This application is a continuation application of U.S. patent application Ser. No. 17/492,488, titled "DECENTRALIZED IDENTITY AUTHENTICATION FRAMEWORK FOR DISTRIBUTED DATA", filed Oct. 1, 2021, which is a continuation-in-part U.S. patent application Ser. No. 17/384,585, titled "SECURE MESSAGING IN A MACHINE LEARNING BLOCKCHAIN NETWORK", filed Jul. 23, 2021, which is a continuation of U.S. patent application Ser. No. 17/063,605, titled "SECURE MESSAGING IN A MACHINE LEARNING BLOCKCHAIN NETWORK", filed Oct. 5, 2020 which claims the benefit of U.S. Provisional Patent Application No. 62/961,594, titled "Supply Chain Tracking and Management Using Blockchain Technology", filed Jan. 15, 2020, which are incorporated herein by reference in their entirety for all purposes.

This application is a continuation application of U.S. patent application Ser. No. 17/492,488, titled "DECENTRALIZED IDENTITY AUTHENTICATION FRAMEWORK FOR DISTRIBUTED DATA", filed Oct. 1, 2021, which claims the benefit of U.S. Provisional Patent Application No. 63/122,875, titled "GRANTING AND REVOKING CREDENTIALS IN A BLOCKCHAIN NETWORK USING PASSWORD PROTECTED TRUNCATED DATA TO CERTIFY PAPERWORK AND TRUST TRIPLETS IDENTITY AUTHENTICATION FRAMEWORK", filed Dec. 8, 2020, which is incorporated herein by reference it its entirety for all purposes.

INCORPORATIONS

The following materials are incorporated herein by reference in their entirety for all purposes:
  U.S. Non-Provisional patent application Ser. No. 16/740,348, titled "Neural Network Classifiers for Block Chain Data Structures", filed Jan. 10, 2020;
  U.S. Non-Provisional patent application Ser. No. 16/740,350, titled "Establishing a Trained Machine Learning Classifier in a Blockchain Network", filed Jan. 10, 2020;
  The FDA Product-Specific Guidance database, fda.gov/drugs/guidances-drugs/product-specific-guidances-generic-drug-development;
  Andy Greenberg, "SECURITY SOFTWARE HAS A SERIOUS SUPPLY-CHAIN SECURITY PROBLEM", Wired (Sep. 18, 2017); and
  Andy Greenberg, "SUPPLY CHAIN HACKERS SNUCK MALWARE INTO VIDEOGAMES", Wired (Apr. 23, 2019).

FIELD OF THE TECHNOLOGY DISCLOSED

The technology disclosed relates to decentralized identity authentication and management in a network of computers and corresponding data processing methods and products implementing secure authentication of users and user's credential claims for access to a distributed permissioned data structure sharable among disparate enterprises. In particular, the technology disclosed relates to using security software technology to implement authentication and credentialing by a trusted party of a non-credentialed user, enabling controlled access to a secure permissioned blockchain data distributed among disparate enterprise actors.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Much of the world's business activity is driven by individuals working together collaboratively, joining together through legal as well as less formal entities which we will term "enterprises." Very few people work in a vacuum—rather they apply legal veneer to organize their activities, while supporting privacy rights of their stakeholders. Technologies must of course keep up with this trend toward newer, decentralized services. This trend also drives increased regulation, especially in the area of privacy rights, e.g., GDPR, Calprivacy, etc., which brings with it increased privacy as well as concomitant increases in cost. Research by the Mercatus Center at George Mason University indicates that the accumulation of rules over the past several decades has slowed economic growth, amounting to an estimated $4 trillion loss in US GDP in 2012 (had regulations stayed at 1980 levels).

As online systems are pressed into service to meet the needs driven by increased regulation, conventional technologies fail to address the complexities posed by distributed collaboratively acting systems, such as for example the need for security and authentication of users of collaborative systems acting in other parts of the world. For example, conventional technologies frequently implement older identity schemas whose centralization results in single points of failure. Many existing systems retain and manage credentials on behalf of all users in the system, creating vulnerability to attack. In a conventional implementation, a single admin provisioning many accounts, would have access to (or maintain a separate email account to collect) that information, and could therefore unwittingly create a single point of failure. In a classic scenario, a malevolent attacker could send an authentic-looking request to another system actor, which diverts to the attacker's own website, could then issue an authentic-looking one-time verification code via SMS, and then ask the victim questions about whatever the attacker would like.

Recent news events such as the Solarwinds hack reinforce the fact that centralized approaches can be susceptible to malfeasance. Usage scenarios such as diagnosis, analysis, and compliance historically require one human to have centralized access to all of other parties' data. This represents a substantial threat surface. In fact, according to a study by IBM, human error is the main cause of 95% of cyber security breaches. Further, compliance requires accurate input of information. Diagnosis requires voluminous amounts of data about complex topics. Thus not all actors that provide information to automated systems can be trusted with access to the data.

What is really needed are improvements in authenticating/credentialing users of transactional based systems that enables trusted entities to share access to private distributed shared data.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 2A is a flow diagram 200A depicting a method for implementing decentralized identity authentication and management in the embodiment of FIG. 1A.

FIG. 2B1 is a flow diagram 200B1 depicting a method for withdrawing a user from decentralized identity authentication and management in the embodiment of FIG. 1A.

FIG. 2B2 is a flow diagram 200B2 depicting an alternative method for withdrawing a user from decentralized identity authentication and management in the embodiment of FIG. 1A.

FIG. 2C is a flowchart illustrating a method for establishing trusted relationship(s) between requester(s) and recipient(s) in a blockchain network, according to various embodiments.

FIG. 2D is a flowchart illustrating a method for finding additional instances of like events from a reported first event involving a first physical object in a blockchain network, according to various embodiments.

FIG. 2E is a flowchart illustrating a method for finding additional instances of problem shipments from a problem report of a first damaged shipment in a blockchain network, according to various embodiments.

FIG. 2F is a flowchart illustrating a method for initiating commanded actions responsive to reported events in which intervention is desired in a blockchain network, according to various embodiments.

FIG. 3B1 is a flow diagram 300B1 depicting flows for withdrawing a user from decentralized identity authentication and management in the embodiment of FIG. 1A.

FIG. 3B2 is a flow diagram 300B2 depicting alternative flows for withdrawing a user from decentralized identity authentication and management in the embodiment of FIG. 1A.

FIG. 5 illustrates an example storage block of a blockchain network that implements the technology disclosed.

FIG. 6A illustrates an example workflow 600 in which a smart contract 604A implements the technology disclosed.

FIGS. 8A, 8B, 8C, 8D, and 8E depict examples of authentication documentation submissions 800.

FIG. 9 illustrates one implementation of a computer system 900 that can be used to implement the technology disclosed.

FIG. 11 depicts a block diagram of training a convolutional neural network in accordance with one implementation of the technology disclosed.

FIG. 12A is a flowchart illustrating a method for establishing a blockchain network implementing event detection, tracking and management for rule-based compliance, according to various embodiments.

FIG. 12B is a flowchart illustrating a method for establishing a trained machine learning classifier using a blockchain network, according to various embodiments.

FIG. 12C is a flowchart illustrating a method for establishing a trained machine learning classifier using unsupervised machine learning in a blockchain network.

FIG. 12D is a flowchart illustrating a method for establishing a trained machine learning classifier using semi-supervised machine learning for classifying nodes in a blockchain network in a healthy blockchain network state(s) or an unhealthy blockchain network state(s).

FIG. 13B illustrates using a neural network for implementing autoencoding to detect a blockchain network health state of a block chain.

DETAILED DESCRIPTION OF SPECIFIC IMPLEMENTATIONS

Motivation

Figure 1A:
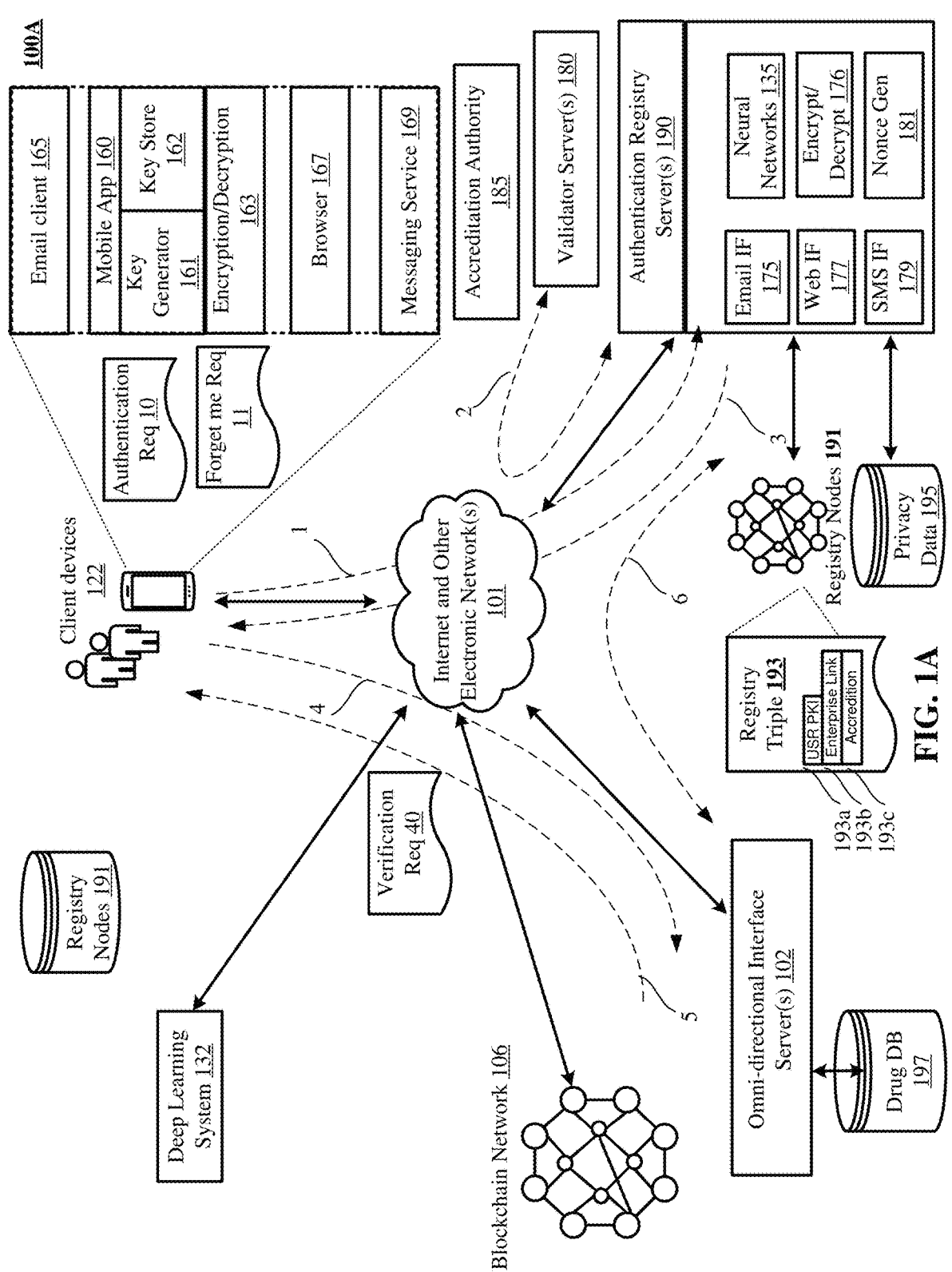
FIG. 1A shows an architectural level schematic of a system 100A that implements technology for implementing decentralized identity authentication and management.

Disclosed are system and method implemented decentralized identity authentication and management enabling secure interoperability and sharing of permissioned data structures between enterprise and/or other entities. Implementations can include automated processes and systems that gather evidence from requestors, as well as professional certification authorities, obtain determinations of authenticity, and create digital identifiers for authenticated requestors. Some determinations can be obtained from neural network implemented trained classifiers. Other determinations can be obtained from data entry. Requestors seeking to withdraw from certification can do so using a process that eliminates personally identifiable information of the withdrawing requestor. Implementations can enable more uniform application of security and authentication frameworks and protocols across a spectrum of interoperable enterprise entities in applications requiring restricted access to sensitive but shared data held in permissioned blockchain or other data structures. Implementations can provide greater levels of security for data by employing decentralized approaches to credential data, eliminating single points of failure scenarios in critically important supply scenarios without sacrificing user privacy. The disclosed technology is applicable in drug and food shipments and other types of high value secure supply chains.

INTRODUCTION

The technology disclosed relates to secure systems and methods implementing decentralized identity authentication and management used for accessing, creating and maintaining private, shared and sensitive documents. The technology disclosed includes an aggregation of enterprise-generated decentralized identifiers (i.e. DIDs) assigned to authenticated users, each contributing their associated public keys to form a public key registry, which in turn establishes a registry node. These registry nodes may be replicated. In some implementations, registry nodes are stored in a blockchain or other distributed ledger. Alternatively, the registry nodes can be implemented with databases, relational or object oriented, or other data structures or combinations thereof. In some implementations, registry nodes can interact with other registry nodes, subject to the governance of an agreed trust framework. The disclosed technology further includes decentralized systems and methods that implement the DIDs and associated verifiable credentials (or VCs) that may be stored, challenged, updated and (re-) authenticated and distributed/decentralized ledgers (including blockchain) Typically these ledgers are implemented as blockchains that record a DID document corresponding to a DID (Decentralized IDentifier). The DID document generally lists public keys for the DID.

Documents can be stored using a data structure comprised of a network of nodes, such as a permissioned block chain, and more particularly to authenticating actors to access permissioned block chain data shared among enterprises to validate documents in high security, high data integrity applications. Information about requestors can be gathered from the requestors themselves, licensing bodies, professional certification bodies, and the like, that can be either trusted or non-trusted, validated, and once validated, stored in a private data store. Requestors whose certifications are validated are given access via their smartphone or portable device, to create a unique digital identifier, e.g., a public-private key pair, of which their private secret key is maintained by them on a digital device or address under their control. The public key can be stored in a registry node using a trusted triple data structure comprised of the public key, enterprise link to an application on a server belonging to an enterprise network member sponsoring the requestor, e.g., a root or source of trust, such as a digital certificate, and the accreditation. Accreditations can be implemented using DIDs, e.g., a DID is implemented in embodiments using a uniform resource identifier (URI) having the form "did: <did-method-name>:<content>", which identifies a particular entity (e.g., a human, a server, a logical object, a physical object). Associated with a DID is a DID document listing associated public keys. The DID document corresponding to a DID is obtained through a process called "DID resolution", which is specific to the DID method. The DID document could be derived from the DID itself (as in did:key) or downloaded from a web server (as in did:web) or retrieved from a public blockchain (as in did:ethr). DID resolution involves producing a canonical DID document from the public key itself, with no need to query a server. For example, a DID defined by—did:web:w3c.xyz might translate into a URL //w3c.xyz/.well-known/did.json, in which case DID resolution involves a HTTP GET of that URL. When the requestor seeks to access data in the permissioned private data structure on behalf of her enterprise, she attaches the digital credential. The recipient server upon receiving the request to access data by the requestor can initiate a transaction with the registry to verify the digital credential. Some applications relate to pharmaceuticals, artificial heart valves and other compositions, systems and apparatus for medical uses and other high security, high data integrity applications.

System Overview

The technology disclosed describes system and method implementations of decentralized identity authentication and management for securing sensitive private data shared among an array of enterprise actors while preserving individual user privacy in permissioned block chain—or other shared data structure—centric systems. Implementations can control gathering of evidence of certifications and identity from requestors and/or professional certification bodies or licensing bodies, in accordance with a common framework and/or protocols agreed upon by the enterprise actors. Implementations obtain determinations that the evidence is sufficient to certify the requestor and issue a digital identifier to the requestor. Information gathered from requestor and trusted/semi-trusted sources can be stored privately, such that it does not get exposed to other actors and/or software in the permissioned blockchain. A digital credential can be created for the authenticated requestor and a portion of this credential can be stored in a registry. The requestor retains control of the private key portion of the digital credential and it can be stored locally on the requestor's device, reducing the vulnerability of the system to attack, as each requestor's private information is not part of the transactions between the requestor and the permissioned block chain. FIGS. 1A, 1B, 1C, and 1D show an architectural level schematic diagrams of a system in accordance with some of these implementations. Because FIGS. 1A, 1B, 1C, and 1D are architectural diagrams, certain details are intentionally omitted to improve the clarity of the description.

The discussion of FIGS. 1A, 1B, 1C, and 1D will be organized as follows. First, the elements of the figure will be described, followed by their interconnections. Then, the use of the elements in the system will be described in greater detail.

FIG. 1A shows an architectural level schematic of a system 100A that implements decentralized identity authentication and management. One implementation called XATP is suitable for authenticating users to access data in the blockchain networks of FIGS. 1B and 1C, however the disclosed technology is suited for other application environments as well. For example, with identity toolchains, such as Hyperledger Indy™ blockchains comprising a subset of a broader family of decentralized ledger technologies are supported. The components and subcomponents of the entities making up the implementation depicted in FIG. 1A will be described in relation to one another. Then, operation of these entities will be described below with further reference to FIGS. 2A, 2B1 and 2B2 and 3A, 3B1 and 3B2. The system 100A includes authentication registry servers 190, which are coupled to the internet 101 and can interoperate with various servers and components belonging to member organizations, such as omni-directional interface server(s) 102, for example, to verify credentials of users making requests for information. Omni-directional interface server(s) 102 have access to sensitive, private or confidential data shared among organizations using the blockchain network 106, as well as access to private collections of data 197 stored for an organization, as well as other servers and other entities (not shown by FIG. 1A for clarity sake) that comprise a blockchain network 106. Omni-directional interface server(s) 102 can receive requests via Internet 101 to access to the blockchain network 106 from client devices 122 belonging to users that have a decentralized identifier (DID) created by the authentication registry servers 190 for users that the authentication registry servers, in cooperation with external resources of various types, such as validation servers 180, have authenticated using the disclosed decentralized authentication technology described herein below with reference to FIGS. 2A, 2B1 and 2B2 and 3A, 3B1 and 3B2.

Users interact with the components of system 100A via a plurality of client devices 122, some of which are mobile applications hosting a mobile application 160. New users seeking authentication, herein termed "requestors" can be sponsored by member enterprises and organizations subject to a commonly agreed upon framework of enterprises authorized to interact with one another, to share common data in various forms, including in some implementations a block chain network 106. In some implementations, a machine intelligence process is used to authenticate the requestor. In one implementation, a trained neural network classifier determines whether a requestor's request can be properly authenticated. Classifiers can be trained to classify requests into "good" e.g., authentic, vs. "bad" e.g., fraudfeasor, based upon evidence provided by a requestor in a request as well as certificates of third-party professional or licensing bodies related to the requestor. Trained classifiers can be implemented by Neural networks 135 for example, or other machine learning technology can be used. A deep learning system 132 can be used to train one or more neural networks or other learning model(s) 135, and Internet and/or other electronic communications network(s) 101. A machine intelligence process can include using a training set of example submissions of evidence and ground truth outcomes. In one implementation, the machine intelligence process includes identifying patterns in data points indicating clusters of data, and applying a label to each cluster; and continuously training a classifier including a neural network with at least some of the clusters and labels. In one implementation, values for one or more labels associated with the training set are determined from a set including at least a plurality of counterfeit, expired, hacked, intentional adulteration, unfit for authentication, and fraudulent activity.

Authentication registry server(s) 190 implement a verifiable data registry comprised of registry nodes 191 using servers and methods for accessing data about an ID that can be trusted by all member organizations of the network. In some implementations, registry nodes 191 are stored in a blockchain or other distributed ledger. Alternatively, the registry nodes can be implemented with databases, relational or object oriented, or other data structures or combinations thereof.

Authentication registry server 190 can cooperatively interface and interoperate with an accreditation authority validator server(s) 180 to obtain validation of claims of authority, e.g., professional licenses, professional certificates, professional society memberships and so forth, presented by the requestors seeking authentication. In some implementations a neural network is trained to perform the validation functionality. Training sets to train the neural network can include both correct conclusions as well as false conclusions.

Requestor Authentication Modalities

Figure 3A:
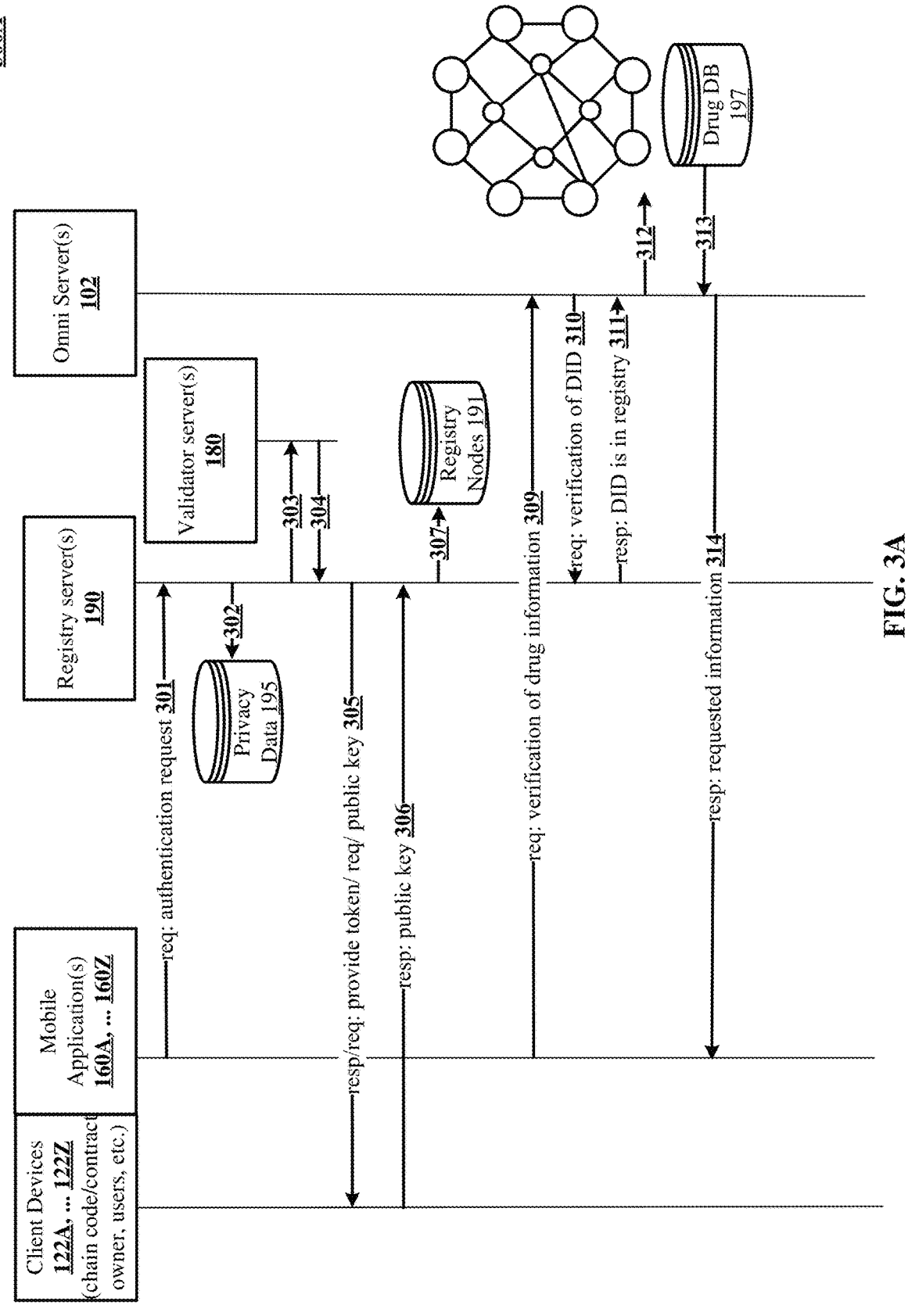
FIG. 3A is a flow diagram 300A depicting flows for implementing decentralized identity authentication and management in the embodiment of FIG. 1A.

Our disclosed decentralized authentication and management technology of FIG. 1A can be implemented in the blockchain ecosystem 100B, 100C, 100D of FIGS. 1B, 1C and 1D based upon a distributed, decentralized authentication process, an example of which will be described with reference to flowcharts 200A of FIG. 2A, and flow diagrams 300A of FIG. 3A illustrating a method for authenticating a user and establishing a verifiable digital identifier in a decentralized registry, and flowcharts 200B1, 200B2 of FIG. 2B1, FIG. 2B2 and flow diagrams 300B1, 300B2 of FIG. 3B1, FIG. 3B2 illustrating a method for removing a user who requests to withdraw from the registry or whose removal is requested by a member of the blockchain ecosystem, respectively. Our decentralized authentication and management technology is applicable to installations implementing shared, private data, high security, and user privacy, such as a blockchain network implementing pharmaceuticals supply chain event detection, tracking and management according to various embodiments in the technology of FIG. 1A.

Accordingly, in the flowchart 200A, a user of a client device 122 has downloaded a mobile application 160 that is stored to a trusted source 120 (e.g., an app store) to be provided to users upon acceptance of an invitation to authenticate with a multi-organizational system. An authentication registry server 190 provides a verifiable data registry, in which members of a multi-organizational system e.g., permissioned blockchain network 106, can obtain verification of a Decentralized ID (DID) presented by a user, e.g., look up Alice's public key in the DID registry node to confirm she is who she claims to be.

Figure 1B:
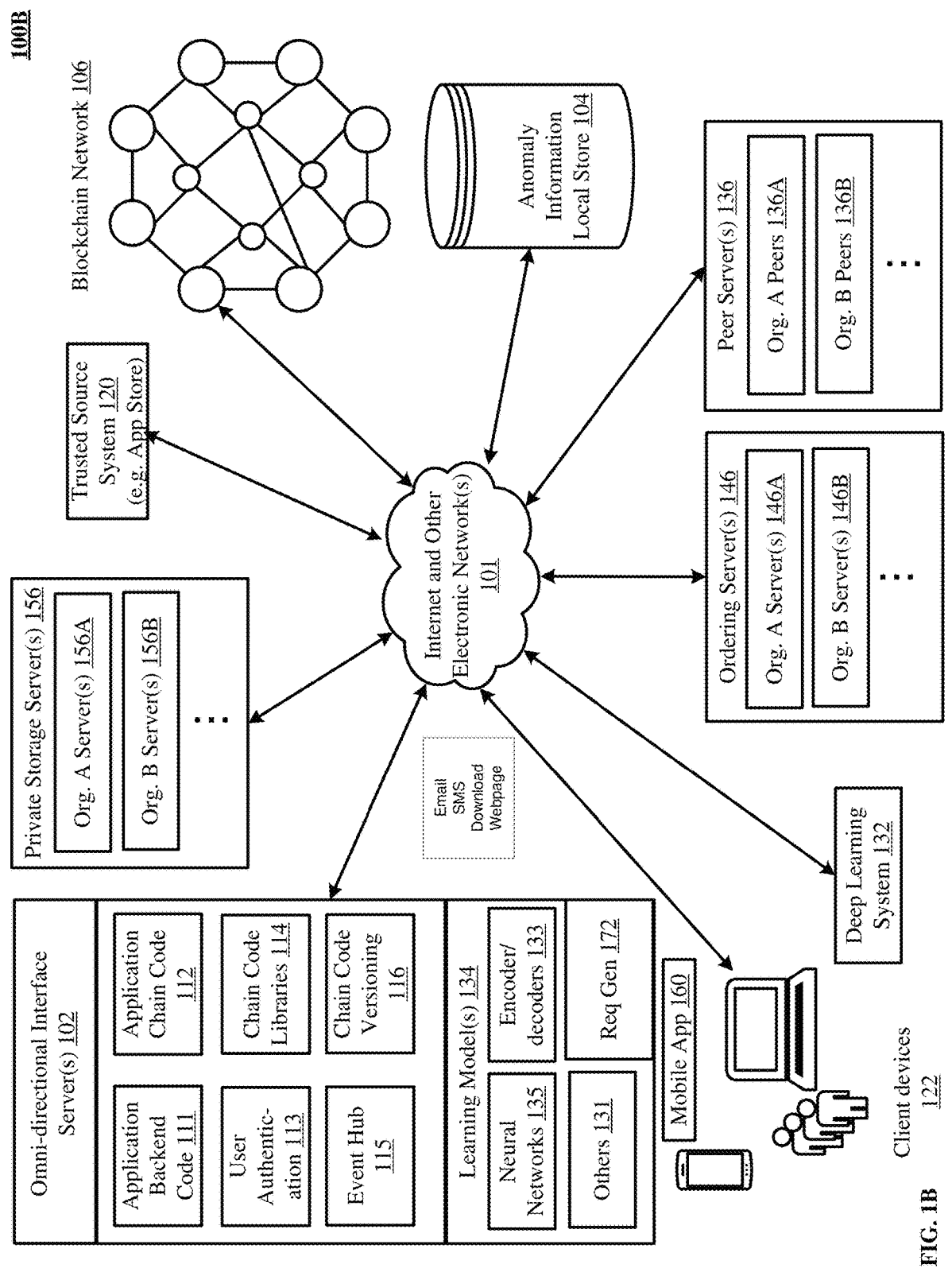
FIG. 1B shows an architectural level schematic of a system 100B that implements a blockchain network of trusted actors in which the disclosed technology implementing decentralized identity authentication and management can be embodied.

In a decentralized authentication process block 201 of flowchart 200A and flow 301 of flow diagram 300A, an authentication registry server 190 (of FIG. 1A) receives (Action 1 of FIG. 1A) a request 10 from an application 160 of a client device(s) 122 (belonging to a human requestor(s)) a request to authenticate the user of device 122 with the multi-organizational system 100B of FIG. 1B. In implementations, this request can be Email as the vehicle for sending this request, however other channels of Networks 101, e.g., SMS, HTTPS, etc. are also available. As also shown by FIG. 1A, the request 10 includes: (i) identity documentation identifying the user and captured by the user application at a time of making the request and (ii) claims made by an entity administrator supporting a role, as determined by rules of a trust framework adopted by the network members with request 10 for information. The authentication registry server 190 upon receiving 1 request 10 to authenticate, controls evidence collection, authentication, and credentialing of the requestors once they are authenticated.

In block 202 and flow 302, registry server 190 stores in a private storage 195 by the registry server, the (i) identity documentation and (ii) claims from the device 122. In one implementation, documentation supporting the claim is uploaded to private storage 195 with a message authentication code (MAC) written to a distributed ledger (not shown in FIG. 1A for clarity sake). In one implementation, the distributed ledger implemented a public hash, file body content and hashed metadata, thereby protecting from dictionary attack. Hash of metadata is stored on a block chain, such as registry nodes 191. In some implementations, registry nodes 191 are stored in a blockchain or other distributed ledger. Alternatively, the registry nodes can be implemented with databases, relational or object oriented, or other data structures or combinations thereof. During an audit, the server 190 can produce metadata and document and algorithm in order to proves the registry server 190 created it; thereby providing an auditable document engine. This process involves three components: (i) a public file seal, an unforgeable public hash record that is recorded to the blockchain and authenticates the private file seal; (ii) a private file seal, which contains document metadata and the "salt," and is necessary to authenticate a private document body; and (iii) the private document body, i.e., the actual content that has been sealed. In this way, the user has total control over their data, while logging a digital signature to the distributed ledger ultimately ensures that the documentation cannot be altered without detection.

In block 203 and flow 303, registry server 190 sends (Action 2 of FIG. 1A) the identity documentation and claims via an external validator interface to a validator server 180. In some installations, use of an external validator ensures that credentialling is consistent on a super-organizational level. In implementations, machine learning techniques are implemented by the external validator, in which a machine intelligence process is used to authenticate the requestor using a trained neural network classifier trained using a training set of example submissions of evidence and ground truth outcomes. In one implementation, the machine intelligence process identifies patterns in data points indicating clusters of data, and applies a label to each cluster; and continuously trains a classifier including a neural network with at least some of the clusters and labels. In one implementation, the machine intelligence process employs values for one or more labels associated with the training set are determined from a set including at least a plurality of counterfeit, expired, hacked, intentional adulteration, unfit for authentication, and fraudulent activity.

In block 204 and flow 304, a requestor's evidence and claims of authority are validated by the validator servers 180. The requestors are credentialed by the registry server 190 which controls the process of creating a decentralized digital identifier (DID) for the requestor. In flow 305, the registry server 190 sends (Action 3 of FIG. 1A) to the client device 122 (i) a one-time token to create a public-private key pair; and (ii) a request to provide a public key of the public-private key pair. In implementations, this request can be Email that can be opened by the application 160 as the vehicle for sending this one-time token and request, however other channels of Networks 101, e.g., SMS, HTTPS, etc. are also available.

In block 205 and flow 306, the registry server 190 receives the requestor's public key, and creates a registry triple 193 that includes (a) the public key 193a, that in one implementation, can be an X509 certificate. The public id of the user's keypair is provided to the server and the user receives a certificate while keeping their private key private; (b) along with a link 193b to the enterprise sponsoring the newly validated user, that in one implementation is a trust root, e.g., a certificate signed by a trusted source e.g., Verisign; and (c) the accreditation data 193c (e.g., a DID). The registry triple 193 implements a pseudonymous ID e.g., a public key; thereby avoiding use of PII of the certified user. Server 190 stored PII is stored separately in private data store 195 so that it can be expunged. Some implementations provide a Selective disclosure credential in which a user can choose the elements to disclose to make a verifiable presentation, e.g., an age and a picture to prove the user is over 18 years of age, need not disclose a home address, etc. Registry server 190 creates a signature that allows such selective disclosure and to use the selective disclosure credential throughout the permissioned blockchain system, thereby enabling implementations to disclose minimal PII and store minimal PII. In flow 307, the registry server 190 stores the registry triple 193 as created in the registry nodes 191 on the newly credentialled user's behalf.

Authenticated Requestor Use of the Authentication

With continuing reference to FIGS. 1A, 2A and 3A, once credentialled, the user can send requests to other systems and components of member organizations of the blockchain network 106, such as an omni-directional interface server 102. In an example pharmaceuticals implementation, with reference to block 206 of FIG. 2A and flow 309 of FIG. 3A, a credentialed user 122 can send (Action 4 of FIG. 1A) a drug information verification request 40 to an omni-directional interface server(s) 102 of a drug manufacturer to obtain verification of drug information stored in their drug database 197 or in nodes on the block chain 106. The user device 122 will include their public key portion of their decentralized identifier (DID) with the request 40. In block 206 and flow 310, the omni-directional interface server belonging to a member organization of the blockchain network 106 can verify the decentralized identifier (DID) of the user 122 by sending (Action 6 of FIG. 1A) a request for verification of authentication registry server 190. In flow 311, the authentication registry server 190 responds indicating that the user's DID is in the registry 191. Omni interface server 102, having confirmed the request is from a certified user, in flows 311, 312 and 313, retrieves the requested information from private drug storage and/or from blockchain network 106, and responds to the request in flow 314.

In implementations no registry node 191 contains credentials for all users permitted access to the shared private permissioned blockchain data structure. In such fashion, the approach of our technology implements a self-sovereign identity, meaning that the registry server 190 does not need store sensitive data, e.g., there is no collection of private keys, social security numbers, etc.

Requestor Withdrawing Authentication Modalities

Now with reference to FIG. 2B1 and FIG. 3B1, illustrating a flowchart 200B1 and a flow diagram 300B1 respectively, depicting example process for withdrawing a user from decentralized identity authentication and management in the embodiment of FIG. 1A.

In a decentralized authentication process block 211 of flowchart 200B1 of FIG. 2B1 and flow 315 of flow diagram 300B1 of FIG. 3B1, an authentication registry server 190 (of FIG. 1A) receives a request 11 from an application 160 of a client device(s) 122 (belonging to a human requestor(s)) to withdraw the user from accessing the permissioned blockchain. In implementations, this request can be Email as the vehicle for sending this request, however other channels of Networks 101, e.g., SMS, HTTPS, etc. are also available. receiving by the registry server, a second request by the requestor to withdraw from accessing the permissioned blockchain.

In block 212 and flow 317 responsive to receiving a request from a requesting user application to be forgotten, the registry server 190 rescinds the distributed digital credential issued to the requestor by revoking the distributed digital credential by deleting a trusted triple data structure corresponding to the user application from the registry of nodes 191, the trusted triple data structure comprised of: (a) a public key 193*a*, (b) a link 193*b* to an enterprise application on a server for which the requestor is being authenticated, and (c) one or more third-party accreditations 193*c* in the claim as validated; thereby enabling the requesting user to withdraw their credential.

In block 213 and flow 318, the registry server 190 deletes from private storage any identity documentation corresponding to the requestor. Transactions from a requesting user that has withdrawn their credential remain in the blockchain and tied to an organization to which the requesting user was assigned; however name, license and any personally identifiable information of the requesting user are removed. Accordingly, by application of our technology, PII need never be present on a blockchain, addressing and solving the problem that if it were present on the blockchain it would not be able to be deleted without deleting the whole blockchain.

In block 214 and flow 319, the registry server 190 confirms that the user making the request has been removed from the registry and that their personally identifiable information has been removed.

In some embodiments, the registry server 190 (optionally) confirms with an omni server 102 of the appropriate network member (e.g., read from the trust-triple a link to an appropriate omni server belonging to an organization who sponsored the withdrawing member) has been deleted and that any PII of the user withdrawing has been removed. For example, in a first scenario, the registry server 190 searches the trust triple 193 for a link 193*b* to the appropriate omni server 102 belonging to an organization who sponsored the withdrawing member, and communicates to the omni server 102 that the withdrawing user has been deleted from the registry in first optional flow 321. Of course, this notification would also ideally be devoid of PII, so the notification would just be along the lines of "Certificate holder 123 is deleted from the registry". In a second optional flow 323, the omni server 102 acknowledges the deletion. In a second scenario, if the member has PII of the user, the omni server 102 can confirm to the registry server 190 that the member has removed the user's PII.

Member Triggered Withdrawal Authentication Modalities

Now with reference to FIG. 2B2 and FIG. 3B2, illustrating a flowchart 200B2 and a flow diagram 300B2 respectively, depicting an alternative process for withdrawing a user from decentralized identity authentication and management in the embodiment of FIG. 1A.

In a decentralized authentication process block 215 of flowchart 200B2 of FIG. 2B2 and flow 325 of flow diagram 300B2 of FIG. 3B2, an authentication registry server 190 (of FIG. 1A) receives a request 11 from an omni server 102 of a member of blockchain network 106 (belonging to an organization sponsoring human requestor(s)) to withdraw a sponsored user from accessing the permissioned blockchain.

In block 216 and flow 317 responsive to receiving a request from a requesting user application to be forgotten, the registry server 190 rescinds the distributed digital credential issued to the requestor by revoking the distributed digital credential by deleting a trusted triple data structure corresponding to the user application from the registry of nodes 191, the trusted triple data structure comprised of: (a) a public key 193*a*, (b) a link 193*b* to an enterprise application on a server for which the requestor is being authenticated, and (c) one or more third-party accreditations 193*c* in the claim as validated; thereby enabling the requesting member server to remove the sponsored user's credential.

In block 217 and flow 318, the registry server 190 deletes from private storage any identity documentation corresponding to the sponsored user. Transactions from the sponsored user whose credential has been withdrawn remain in the blockchain and tied to an organization to which the sponsored user was assigned; however name, license and any personally identifiable information of the sponsored user are removed. Accordingly, by application of our technology, PII need never be present on a blockchain, addressing and solving the problem that if it were present on the blockchain it would not be able to be deleted without deleting the whole blockchain.

In block 218 and flow 329, the registry server 190 confirms that the user has been removed from the registry and that their personally identifiable information has been removed.

In some implementations, the registry server 190 communicates to the application 122 of the sponsored user that the sponsored user has been deleted from the registry in first optional flow 325. In a second optional flow 327, the application 122 acknowledges the deletion. In a second scenario, if the application 122 has PII, the application 122 can confirm to the registry server 190 that the user's PII is deleted.

Credential/Authentication Renewals Modalities

Certain implementations include methods for periodic renewals addressing expired memberships, re-authentication/re-credentialing of users, and/or comparison of evidence submitted with prior submitted evidence by in the validator 180, etc. In one implementation, if at the end of the year, a user's evidence (e.g., license) or membership expires, the application 160 on user's device 122 will prompt the user to enter a re-authentication process (see e.g., FIGS. 8A-8E and accompanying description hereinbelow). In one implementation, the user seeking to re-authenticate or renew their expired membership can retrieve a photo submitted as identity documentation in action 204 of FIG. 2A during authentication processing and stored by the application 160 on the user's own device 122, in private data store 195 of FIG. 1A, or both. In alternative implementations the user can change their avatar photo but the photo with their license and only a new photo is permitted.

In some implementations, the application 160 on device 122 might invite the user to re-use a previously captured photo for verification. In some implementations, re-authenticating users are prompted for both a fresh photograph and the previously captured photograph previously captured during first authentication/credentialling, and a trained machine classifier 135 of deep learning system 132 (or other neural network or machine intelligence process) is used to verity that the two photographs are indeed of the same person.

If a user withdraws, e.g., asks to delete their membership forever, implementations will remove the photo from the private store 195. In such case, if the withdrawn user desires to again become known to the blockchain network 106, the withdrawn user would now be treated as a completely new user and will go through the initial authentication process of FIG. 2A. Further in implementations the user's photo is removed from any registry nodes 191 if it has been stored there.

Network of Trusted Actors and Decentralized Credentialing

FIG. 1B shows an architectural level schematic of a system 100B that implements a blockchain network of trusted actors in which the disclosed technology implementing decentralized identity authentication and management can be embodied. The system 100B includes omni-directional interface server(s) 102, anomaly information local store 104, private storage server(s) 156 accessing private collections data stored for each organization, deep learning system 132 can be used to train one or more neural networks or other learning model(s) 134, peer server(s) 136 that also include chain code (or smart contracts) implementing decentralized applications (DApps), ordering server(s) 146, and other servers and other trusted entities 170, not shown by FIG. 1B for clarity sake, that comprise a blockchain network 106, communicatively coupled to one another as well as client devices 122 of credentialed users, users requesting access, and other entities, by Internet and/or other electronic communications network(s) 101. Process flows of validating requests, claims of certifications of third party professional boards, licensing bodies, etc. between client devices 122 and authentication registry server 190 are described in further detail herein with reference to FIG. 1A. Pathways for establishing communications between trusted entities 170, such as omni-directional interface server(s) 102, etc. and non-credentialed entities, such as users of client devices 122, are described in further detail herein below with reference to FIG. 1D.

The interconnection of the elements of system 100B will now be described. Network(s) 101 couples the interface server(s) 102, the anomaly information local store 104, with the other servers and other entities that comprise a blockchain network 106, the client devices 122, private storage server(s) 156 accessing private collections data stored for each organization, the deep learning system 132, the learning model(s) 134, peer server(s) 136 that also include chain code (or smart contracts) implementing the DApps, and the ordering server(s) 146, that can be in communication with each other (indicated by solid double-arrowed lines). The actual communication path can be point-to-point over public and/or private networks comprising network(s) 101. The communications can occur over a variety of networks, e.g., private networks, VPN, MPLS circuit, or Internet, and can use appropriate application programming interfaces (APIs) and data interchange formats, e.g., Representational State Transfer (REST), JavaScript Object Notation (JSON), Extensible Markup Language (XML), Simple Object Access Protocol (SOAP), Java Message Service (JMS), and/or Java Platform Module System. At least some of the communications can be encrypted. The communication is generally over a network such as the LAN (local area network), WAN (wide area network), telephone network (Public Switched Telephone Network (PSTN), Session Initiation Protocol (SIP), wireless network, point-to-point network, star network, token ring network, hub network, Internet, inclusive of the mobile Internet, via protocols such as EDGE, 3G, 4G LTE, Wi-Fi, and WiMAX. Additionally, a variety of authorization and authentication techniques, such as username/password, Open Authorization (OAuth), Kerberos, SecureID, digital certificates and more, can be used to secure the communications. The engines or system components of FIGS. 1A, 1B, 1C, and 1D such as deep learning system 132, private storage server(s) 156, ordering server(s) 146, peer server(s) 136, the interface server(s) 102, and other trusted entities comprising blockchain network 106 as well as mobile applications 160 of client devices 122 can be implemented by software running on varying types of computing devices. Example server devices are a workstation, a server, a computing cluster, a blade server, and a server farm. Example client devices include a smart phone, smart tablet, laptop computer, wearable smart headset and/or goggles such as GOOGLEGLASS™ and AR/VR headsets such as Oculus GO™, HTC VIVE™, Sony Playstation™ VR and the like.

Interface server(s) 102, associated by a set of trust relationships with peer server(s) 136, and other servers and other entities, comprise the blockchain network 106, that acts as a distributed database or an immutable ledger which maintains records of all electronic transactions conducted by participants such as interface server(s) 102 and peer server(s) 136 in a peer-to-peer network. A blockchain is maintained by a network of nodes (e.g., interface server(s) 102, peer server(s) 136, etc.) where every node executes and records electronic transactions to a particular chain. The blockchain structure is replicated among the nodes in the network. Because blockchain network 106 implements a peer-to-peer network, it does not require a central authority or trusted intermediaries to authenticate or to settle the electronic transactions or control the underlying infrastructure. Examples of popular blockchain platforms include Hyperledger Fabric™, and Hyperledger Corda™, Hyperledger Ursa™, Hyperledger Indy™ Hyperledger Besu™, Ethereum™, Solana™, Polkadot™, Eris™, Multichain™, and Bitcoin™ Blockchain network 106 includes a distributed data structure (i.e., a "ledger" or "blockchain ledger") comprising a chain of blocks. Servers implementing nodes of blockchain network 106 can host chain code or "smart contracts". Chain code is a piece of code that resides on blockchain and is identified by a unique address. A chain code includes a set of executable functions and state variables. The function code is executed when transactions are sent to the functions. The transactions include input parameters which are required by the functions in the chain code. Upon the execution of a function, the state variables in the chain code change depending on the logic implemented in the function. Chain code can be written in various high-level languages (such as Golang™ or Solidity™ or Python™). Language-specific compilers for chain code (such as Golang™ or Solidity™ or Serpent™ compilers) are used to compile the chain code into bytecode. Once compiled, the chain code is uploaded to peer server(s) 136 of the blockchain network 106 which assign a unique address to each chain code. In permissioned blockchain systems, such as Hyperledger Fabric™, a node in the network can read electronic transactions for which it has permission. (In other blockchain systems, such as Ethereum™, all transactions are accessible to all nodes.)

The electronic transactions in the blockchain ledger are time-stamped and bundled into blocks where each block is identified by its cryptographic hash. The blocks form a linear sequence where each block references the hash of the previous or parent block, forming a chain of blocks called the blockchain. Each block maintains records of all the transactions on the network received since the creation of its previous block. Instead of storing the information on all the transactions within the block itself, a special data structure called a Merkle tree is used to store the transactions and only the hash of the root of the Merkle tree is stored in the block. Blockchain is an immutable and durable data structure which maintains a record of the transactions that are tamper-resistant. Once a transaction is recorded in a block, it cannot be altered or deleted as long as a majority of the computational power of the network is not controlled by peers who collude to alter the blockchain.

Interface server(s) 102 can leverage blockchain platforms to enable device-to-device and data consumer-to-device electronic transactions. Interface server(s) 102 are preferably configured using application backend code 111 as proxies that have their own blockchain accounts for communicating with peer server(s) 136 in the blockchain network 106 and associated chain code (or smart contracts).

The application chain code 112 can store information on the device identities and usage patterns of client devices 122. Chain code versioning 116 keeps chain code of chain code libraries 114 deployed on Interface server(s) 102 compatible with chain code deployed on associated peer server(s) 136, enabling one of the interface server(s) 102 of "Organization A" to send transactions to the associated chain codes deployed on "Organization A" peer server(s) 136A and receive transactions from the peers of Organization A on the blockchain network 106. Application backend code 111 enables this by running a blockchain client on the interface server(s) 102 that uses a controller service to connect the interface server(s) 102 with peer server(s) 136A of Organization A and peer servers 136B of Organization B, as well as any others that interface server(s) 102 are configured to be in a trusted entity with. An example of a blockchain client is Hyperledger Fabric™. (In alternative implementations, an EthJsonRpc Python™ client for Ethereum™ that uses JSON-based remote procedure calls (RPCs) to implement client-specific methods and provides a high-level interface to create smart contracts on Ethereum™ and to call contract functions.)

New blocks are created and added to the blockchain by participants (e.g., interface server(s) 102, peer server(s) 136). In a permissioned blockchain platform, such as Hyperledger Fabric™, access to the blockchain network 106 is restricted only to a set of pre-defined participants. Participants may elect to permit new blocks to be created and added to the chain by any one of them without a consensus (called "No-op") or to be added by meeting an agreement protocol, such as Practical Byzantine Fault Tolerance (PBFT). For example, two or more parties can agree on a key in such a way that both influence the outcome. This precludes undesired third parties from forcing a key choice on the agreeing parties.

Network of Trusted Actors and Supporting Infrastructure

Figure 1C:
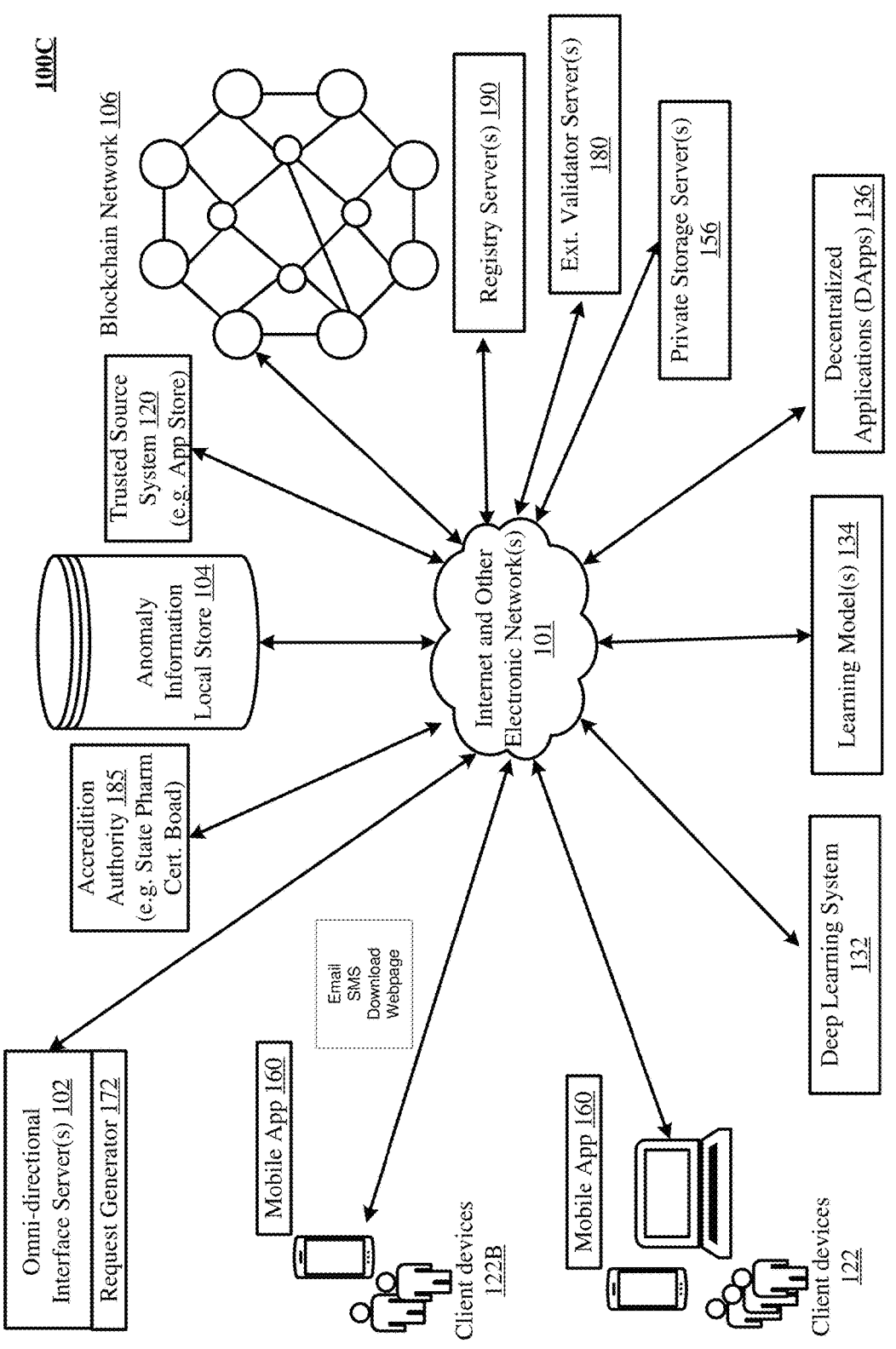
FIG. 1C shows an architectural level schematic of another system 100C that implements a blockchain network of trusted actors in which the disclosed technology implementing decentralized identity authentication and management can be embodied.

FIG. 1C shows an architectural level schematic of a system 100C that implements a blockchain network of trusted actors in which the disclosed technology can be embodied. A public or private without permissions blockchain platform, such as Ethereum™, can be suited for implementing the disclosed technology also. The process of adding blocks to the blockchain in a public or private without permissions blockchain platform is called mining. As shown in FIG. 1C, a plurality of distributed applications 136 hosted on server(s) that are decentralized in nature, with no single entity or organization controlling the infrastructure on which the blocks are stored. FIG. 4B is a block diagram 400B with an example distributed application(s) 136 that can be used to host smart contracts that implement nodes in the blockchain network that perform the mining operations are called miners. New transactions are broadcast to all the nodes on the network. Each miner node creates its own block by collecting the new transactions and then finds a proof-of-work (PoW) for its block by performing complex cryptographic computations. The miners validate the transactions and reach a consensus on the block that should be added next to the blockchain. The newly mined block, called the winning block, is then broadcast to the entire network. The winning block is the one that contains a PoW of a given difficulty.

While each miner on the blockchain network 106 can create its own block, only the block which has a PoW of a given difficulty is accepted to be added to the blockchain. The consensus mechanism ensures that all the nodes agree on the same block to contain the canonical transactions. Blockchain offers enhanced security as compared to centralized systems as every transaction is verified by multiple miners. The integrity of the transaction data recorded in the blocks is protected through strong cryptography. In addition to the transaction data, each block contains a cryptographic hash of itself and the hash of the previous block. Any attempts to modify a transaction would result in a change in the hash and would require all the subsequent blocks to be recomputed. This would be extremely difficult to achieve as long as the majority of miners do not cooperate to attack the network.

With renewed reference to FIG. 1B, in implementations, data too sensitive to risk being stored directly on the blocks of the blockchain network 106 can be stored locally in local store(s) 104. For example, medical privacy laws such as health insurance portability and accountability act (HIPAA), general data protection regulation (GDPR), and others, legal, regulatory or private, place restrictions on the usage and keeping of data. In such cases, information can be stored locally by participants in the blockchain network 106 in local store(s) 104. Addressing information can be pushed by the custodian of the locally stored data, typically in encrypted or other non-human readable form to provide protection from tampering by a single actor and provides for data confidentiality with encryption at the block level.

When client devices 122 wish to avail the services of the interface server(s) 102, these devices execute application software implementing web applications, mobile applications 160, event subscriber (user, automation, business applications), automated applications and the like to authenticate with user authentication code 113. Once authenticated using the processing described hereinbelow with reference to FIGS. 2A-2F and 3A-3C, the authenticated device is enabled to conduct data transactions via the chain code 112 associated with the interface server(s) 102, including responding to Oraculous™ requests to provide information generated by request generator 172. The interface server 102, will obtain services on behalf of the authenticated device, effectively blocking direct linking between user device and nodes in the block chain. For example, one of the client devices 122 accesses the system using an application deployed on a workstation or mobile devices and driven by the interface server(s) 102 accessed over network 101. The mobile application, when backed by the interface server(s) 102, reads barcodes on questionable package and gathers user information enabling the interface server(s) 102 to obtain using neural networks implementing learning models 134 diagnostic information and applications that can trigger remedial action, such as completing a discrepancy report. One implementation can enable photos of barcodes to be taken by a third party, optical character recognition of the human-readable label, and XML or other machine files with the same information. One implementation provides pill recognition using image recognition driven CNN classifiers of learning models 134 trained using ground truth training sets drawn from publicly available and/or other image recognition frameworks. One implementation provides client devices 122 at the reporting party with a series of learning model 134 selected modal screens, enabling client devices 122 to accurately and rapidly notify regulators and counter-parties ("trading partners") of problems.

Ordering server(s) 146 are used by interface server(s) 102 to request transactions with the peer server(s) 136 to retrieve or store information, such as anomaly reports, to the block chain ledger. In this manner the identities of the peer server(s) 136 are anonymized and known to the ordering server(s) 146 in the tamper-proof blockchain network 106.

Private storage server(s) 156 access private collections data stored for each organization, which may comprise information of various drug databases (e.g., the FDA Product-Specific Guidance database, which enables searching and clustering by active ingredient(s)) and communications including machine reading of emails on recalls. Interface server(s) 102 is cooperatively coupled with private storage server(s) 156 that can comprise multiple sources of data stored by individual organizations that are members of the blockchain network 106, thereby minimizing the need to change notification protocols that can be related to machine-readable data and image recognition (e.g., images of pills).

Learning model(s) 134 in conjunction with event hub 115 enable interface server(s) 102 to apply machine learning techniques (cluster identification, free form input learning) to observational global state of the block level events in the block chain, input of responses to follow-up questions obtained from user responses and actions, to identify anomalies, and decide when to gather additional information and/or filing a report to another entity int the blockchain network 106. Learning model(s) 134 implement unsupervised and transitioning to semi-supervised machine learning techniques, thereby enabling (re-)training and refinement to occur.

In one implementation, learning model(s) 134 implement multi-layer ensembles of neural subnetworks includes a first anomaly subnetwork, and a second solution accessibility subnetwork. The learning model(s) 134 are further configured to classify inputs indicating various anomalous sensed conditions into probabilistic anomalies using a first anomaly subnetwork. Determined probabilistic anomalies may be classified into remedial application triggers. Remedial application triggers are invoked to recommend or take actions to remediate, and/or report the anomaly. One implementation the learning model(s) 134 can select a report type to submit based upon the situation state. One implementation can select a report recipient based upon the situation state. For example within the drug and healthcare reporting field, learning model(s) 134 can address reporting among both professionals and consumers: FDA: Field Alert Report (FAR), FDA: Biological Product Deviation Report (BPDR), FDA: Form 3500 (Medwatch, voluntary reporting by healthcare professionals, consumers, and patients), FDA: Form 3500A (Medwatch, mandatory reporting by IND reporters, manufacturers, distributors, importers, and user facilities personnel), FDA: Form 3500B (Medwatch, voluntary reporting by consumers), FDA: Reportable Food Registry, FDA: Vaccine Adverse Event Reporting System (VAERS), FDA: Investigative Drug/Gene Research Study Adverse Event Reports, FDA: Potential Tobacco Product Violations Reporting (Form FDA 3779), USDA *APHIS* Center for Veterinary Biologics Reports, USDA Animal and Plant Health Inspection Service: Adverse Event Reporting, USDA FSIS Electronic Consumer Complaints, DEA Tips, Animal Drug Safety Reporting, Consumer Product Safety Commission Reports, State/local reports: Health Department, Board of Pharmacy, and others.

The deep learning system 132 trains some of the learning model(s) 134 implementing neural networks in semi-supervised modalities to recognize anomalies and trigger remedial actions. In one implementation, neural networks are trained on one or more training servers (e.g., 1302 of FIG. 13C) using training datasets (e.g., 1312 of FIG. 13C) and deployed on one or more production servers (e.g., 1304 of FIG. 13C). For additional description of deep learning system 132 and learning model(s) 134, the skilled person can have reference to commonly owned, copending U.S.

Non-Provisional patent application Ser. No. 16/740,348, titled "Neural Network Classifiers for Block Chain Data Structures", filed Jan. 10, 2020, the entirety of which is incorporated herein by reference for all purposes.

Oraculous™ Communications Server

Figure 1D:
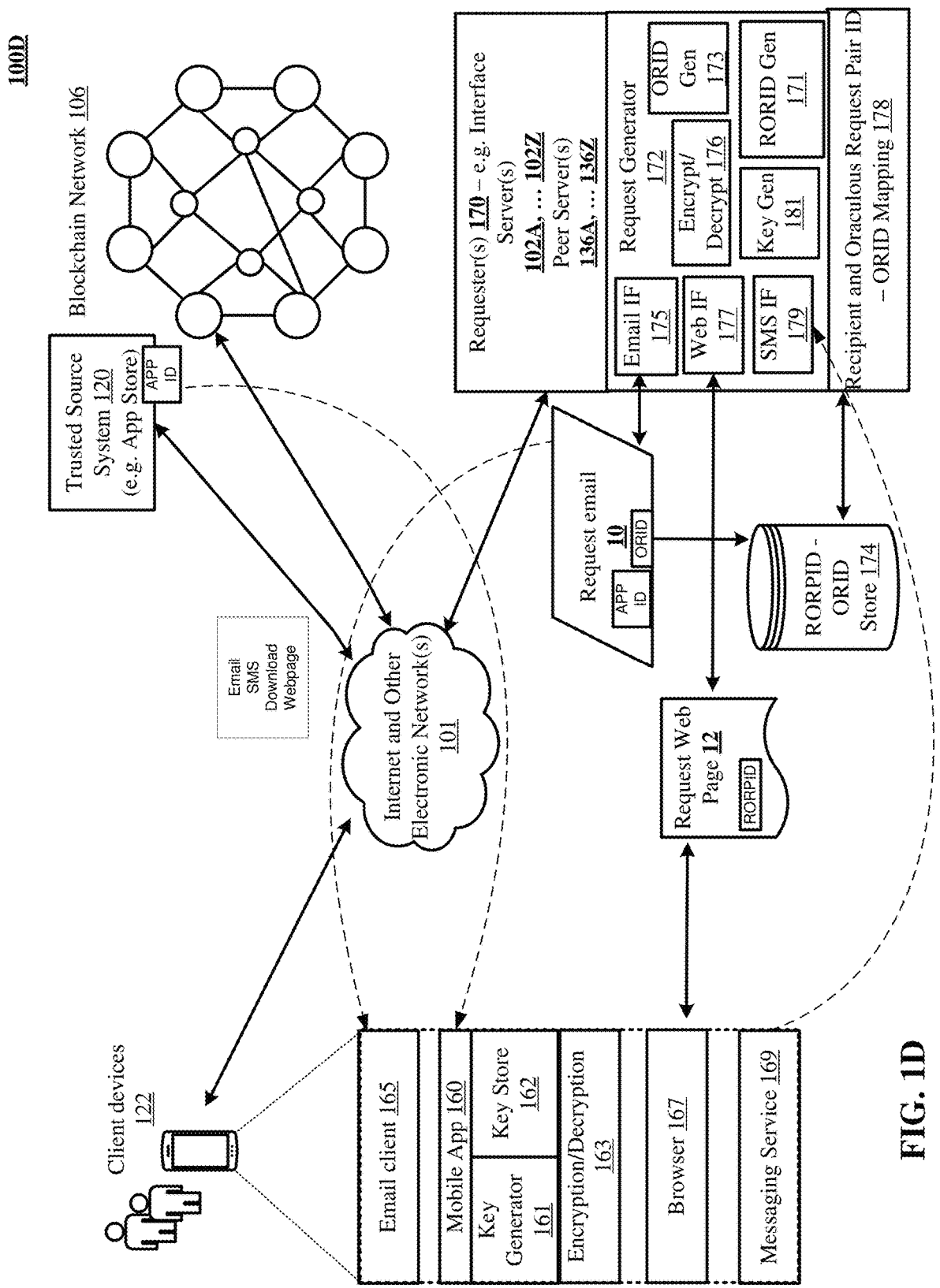
FIG. 1D shows an architectural level schematic of a system 100D that implements technology for establishing trusted relationship(s) between requester(s) and recipient(s) in the blockchain networks of FIGS. 1B and 1C.

FIG. 1D shows an architectural level schematic of a system 100D that implements technology for establishing trusted relationship(s) between requester(s) and recipient(s) in the blockchain networks of FIGS. 1B and 1C. The components and subcomponents of the entities making up the implementation depicted in FIG. 1D will be described in relation to one another. Then, operation of these entities will be described below with further reference to FIGS. 2C and 3C. The system 100D includes requesters 170, which can comprise omni-directional interface server(s) 102, peer server(s) 136 that also include chain code (or smart contracts) implementing decentralized applications (DApps), ordering server(s) 146, private storage server(s) 156 accessing private collections data stored for each organization, as well as other servers and other entities that comprise a blockchain network 106, any of which can make requests of client devices 122, that do not have access to the blockchain network 106 using the two-way multiple modality cross-authentication technology implementing user authentication 113 and described herein below with reference to FIGS. 2C and 3C. A deep learning system 132 can be used to train one or more neural networks or other learning model(s) 134, and Internet and/or other electronic communications network(s) 101.

Requester 170 includes a request generator 172. Request generator 172 includes program logic that creates a request to a non-credentialed recipient soliciting information. In an implementation the request is structured to include a means of authenticating the source of the request, the requester 170 to the recipient of the request.

Request Modalities

In an example embodiment illustrated by FIG. 1D, request generator 172 of a typical requester generates a request 10 as an email using email IF 175. Implementations can, however, generate requests in a variety of modalities, including mixtures of modalities, such as without limitation: (i) email sent to an email address; (ii) push notification sent to a phone number (note that push notifications are not 100% reliable, i.e. a push notification may silently fail to be delivered); (iii) automated phone call made to phone number, employing either additional infrastructure or the use of third-party services; (iv) combinations of (i)-(iii); (v) others.

Two-Way Authentication

In one implementation, request email 10 includes a link (APP ID) identifying a mobile application stored with a trusted source 120, such as an app store provided by a trusted third party (e.g., Apple App Store™, Google Play Store™, etc.) that the recipient device 122 can download and install as mobile application 160; and (ii) a randomized unique identifier (ORID) generated by ORID generator 173 and associated by request generator 172 with request 10 for information that identifies the request 10 to the mobile application 160 once installed. Noteworthy, because the recipient device 122 retrieves his copy of the mobile application 160 from a trusted source 120, i.e., the app store, the mobile application is authentic, and the sender of the request is authentic. Noteworthy is that the mobile application 160 presence in the trusted source 120 is what is providing the authentication to the recipient; in other words, an attacker would not be able to put a fake "look-a-like" in the trusted source 120 (e.g., app store). Using the mobile application 160, the user of device 122 can view links to requests that the mobile application as received, and can open a received request link including a random ID (ORID) generated by ORID generator 173 and associated by request generator 172 with request 10 for information.

An SMS IF 179 in conjunction with messaging service 169 of device 122 enables request generator 172 to obtain a second factor authorization of the device 122 once the mobile application 160 is installed by the user of the device 122. While illustrated by an example using SMS in FIG. 1D, implementations can employ any of a variety of different types of two-factor authorizations having different security levels and requirements for advance setup. The choice of which one to use will depend on app specific and use-case-specific considerations. Types of two-factor authorizations that could be used: (i) one-time code sent to email address—no credentials does not require recipient to possess credentials; (ii) one-time code sent to phone number via push notification—does not require recipient to possess credentials; (iii) one-time code sent encrypted to email address—a public encryption key of the recipient must be known in advance, though this could be specified alongside the recipient email address; (iv) time-based code with shared secret (e.g. Google Authenticator™)—requires recipient to set up the shared secret in advance. Once this second verification processing is complete, the request recipient device 122 has authenticated to the requester 170, and therefore the two-way authentication is complete.

Encryption/decryption 163, key generator 161 and key store 162 of mobile application 160 installed on device 122 and corresponding encryption/decryption 176, key generator 181 and key store 182 of request generator 172 enable corresponding pairs of public and private key pair to be generated by each of the mobile application 160 and the requester 170 and the public keys exchanged. These are the credentials that will be used between these two entities for two-way authentication. In one implementation, the keys are exchanged using Email. In another implementation, keys are exchanged using direct communications between application and server. Once exchanged, keys can be used to pass encrypted traffic between requester and application.

It is noteworthy that in an implementation, when a recipient has already performed actions of installing the mobile application and mutually authenticating application 160 and requester 170, then a notification can be sent directly to the mobile application 160, bypassing the need for switching between email 10 and mobile application 160.

Oracle Request Processing

Once authenticated, the mobile application 160 opens the embedded link in the request 10 in the mobile device's web browser 167. The link includes an auth-token (RORPID) that is unique to that request and that authentication. The RORID generator 171 of the request generator 172 creates the RORPID. The RORPID is embedded into the request link of a request web page 12 and sent to the mobile application 160 by web IF 177. The mobile application 160 can open the link accompanying the RORPID in the browser 169 of the device 122, enabling the recipient to enter the requested information into appropriate fields in the request web page 12. When complete, the information entered is forwarded to the web IF 177 of the request generator 172 of requester 170. The requester 170 commits some information from the request to the blockchain 106.

A recipient and request pair ID—ORID mapping 178 enables multiple requests to be sent to multiple recipients, wherein each is a unique entity in the blockchain ecosystem. The link sent to each recipient should be different, each one containing a unique identifier which can be tied uniquely to that recipient and can be mapped uniquely to that request.

This way, the identity of the recipient who is responding is known. When combined with uniqueness of the ORID described above, this criterion provides for a random, unique "Recipient and Oraculous™ Request Pair ID" (call this RORPID for brevity). Implementing a randomness criterion ensures that the ORID itself does not expose information about the underlying components of the system, as is the case with the ORID. In particular, the RORPID should not be a function of the ORID, as this would expose such information.

A RORPID-ORID store 174 persistent storage is accessible to the requester(s) 170 and stores in persistent storage a variety of data for preserving the integrity of the requests, recipients and other information. For example, a mapping from RORPID to ORID (i.e. the mapping from a recipient and request pair to its corresponding request) can be maintained in the RORPID-ORID store 174 persistent storage. The mapping from RORPID to recipient identity—a recipient identity is a record which defines the recipient's medium of request, two factor authentication, and any other relevant context—can be maintained in the RORPID-ORID store 174 persistent storage. The mapping from ORID to the set of corresponding RORPIDs (i.e. the mapping from an request to the set of its recipient and request pairs) can be maintained in the RORPID-ORID store 174 persistent storage. The RORPID-ORID store 174 persistent storage can also store other relevant data regarding each request tracked, such as without limitation: (i) issue timestamp; (ii) expiration timestamp; (iii) other necessary use-case-specific context for the request; (iv) other relevant data regarding each recipient of a request, e.g., (i) any request-specific context that is specific to this recipient.

Removing Authentications

In an implementation, authentication of the user's mobile application is terminated by command of the server when information needed by the server is gathered and the trusted conversation is completed. In some implementations, the authentication of the user's mobile application is terminated based upon expiry of a time limit to respond. In some implementations, the authentication of the user's mobile application is terminated based upon expiry of a time limit defining a maximal length that authentications can persist. In some implementations, a user of an installed application and re-authenticate with the trusted server. In some implementations, the trusted server resends the request for information to the non-credentialed device as an authorized recipient upon expiry of a time limit to respond.

Failed Authentications

Some implementations will limit the number of attempts for performing two-factor authentication. For example, some implementations may place a limit on the number of failed attempts to authenticate in response to a request. This limit can be made preferably per RORPID (i.e. per recipient, per request), so that if the limit is 10 attempts, a rogue wave of 10 legitimate recipients all getting the authentication wrong once, but in good faith, does not trigger the limitation. Implementations can include a variety of actions to be taken should the limit be exceeded or authentication otherwise fails, such as for example any or combination(s) of: (i) log the triggering offense; (ii) invalidate that request; (iii) ban the IP address of the offender for a period of time, e.g., 10 or greater minutes; (iv) flag the offending recipient as potentially compromised; (v) notify some security admin that some unusual activity is occurring; (vi) if the request pertains to some business arrangement, initiate human contact with the business to see whether something has gone wrong, and potentially to change the email address/cell phone number used as the recipient.

Invalidating an Existing Request

In one implementation, a request can be canceled or revoked by the application server 102. For example, a user initiating cancelling a request is first authenticated and checked for appropriate authority to cancel the request (e.g., user has full credentials on the app server and is authorized to make such an invalidation). Such an invalidation should (unless explicitly blocked by app-specific or use-case-specific configuration) send a notification to the recipients' devices 122 of the invalidated request. In an example scenario, if the request solicited information for: "can you verify the date that XYZ occurred?" but there was some error in the request itself, such as XYZ not having occurred, or XYZ is not the correct fact that occurred, and the issuer of the request wanted to "retract" the request before any recipient responded to it.

In a yet further implementation, a mechanism is provided on the "landing page" of a live request—this would be the landing page that a recipient would see when responding—that to ask that that request be invalidated. For example, the recipient pre-empting an error condition by asking for invalidation. An example of this scenario could be if the request solicited, "what is the car insurance policy number for the car with this license plate number?", an invalidation request could be issued with reason "you have the wrong license plate number, so the question itself is moot.").

Expired Requests

In one implementation, any attempt to open an expired verification request is captured by the request generator 172 and an error handling sequence of actions can be initiated. For example, one error sequence would present a page saying something to the effect of "this verification request has expired—sending a fresh request to the appropriate recipients."

Other implementations may include a non-transitory computer readable storage medium storing instructions executable by a processor to perform actions of the system described above. Yet another implementation may include a method performing actions of the system described above.

Cross Authentication Processes

Figure 3C:
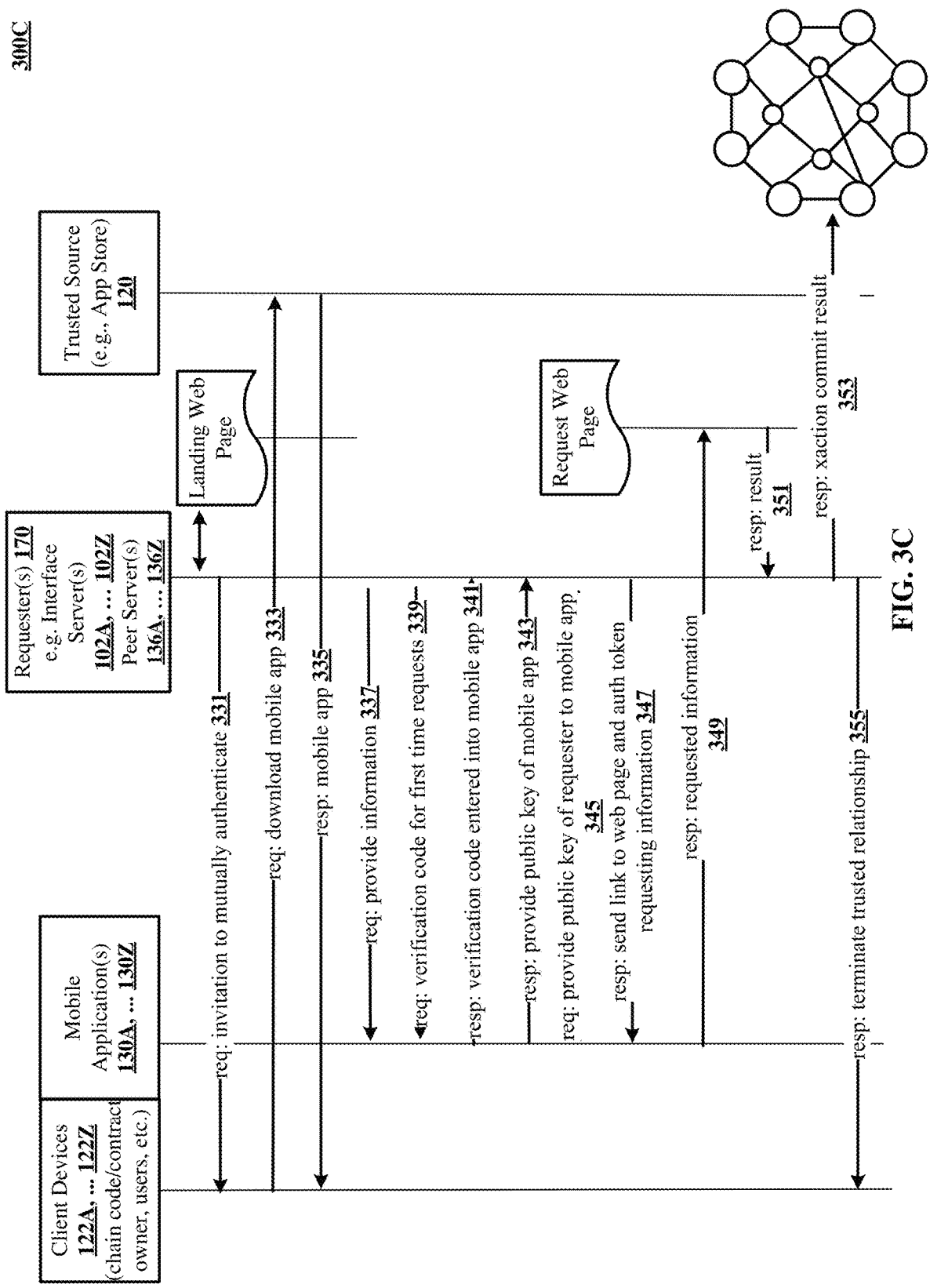
FIG. 3C is a flow diagram 300C depicting flows for establishing trusted relationship(s) between requester(s) and recipient(s) in the technology of FIG. 1D.

Trusted communications in the blockchain ecosystem 100B, 100C of FIGS. 1B and 1C can be based upon a two-way authentication process, an example of which will be described with reference to FIG. 2C, a flowchart illustrating a method for establishing trusted relationship(s) between requester(s) and recipient(s) in a blockchain network implementing event detection, tracking and management according to various embodiments, and FIG. 3C, a flow diagram 300C depicting flows for establishing trusted relationship(s) between requester(s) and recipient(s) in the technology of FIG. 1D.

Accordingly, in the flowchart 200C, at block 221, a mobile application 160 is stored to a trusted source 120 (e.g., an app store) to be provided to users upon acceptance of an invitation.

In an two-way authentication process block 222 of flowchart 200C and flow 331 of flow diagram 300C, an autonomous requester 170 (e.g., 102A, . . . 102Z, 136A, . . . 136Z of FIG. 1B, FIG. 1C) sends a request 10 to a client device(s) 122 (belonging to a human recipient(s)). Email is chosen as the vehicle for sending this request, however other channels of Networks 101, e.g., SMS, HTTPS, etc. are also available. As also shown by FIG. 1D, the request 10 includes: (i) a link to the mobile application provided in the trusted source system 120 (e.g., app store); and (ii) a link including a random ID (ORID) generated by ORID generator 173 and associated by request generator 172 with request 10 for information.

In block 223 and flow 333, device 122 uses the link and an app store app to select and download the mobile application from the trusted source. Accordingly, because the recipient retrieves his copy of the mobile application 160 from a trusted source 120, i.e., the app store, the mobile application is authentic, and the sender of the request is authentic. Noteworthy is that the mobile application 160 presence in the trusted source 120 is what is providing the authentication to the recipient; in other words, an attacker would not be able to put a fake "look-a-like" in the trusted source 120 (e.g., app store).

In block 224 and flow 335 the user installs and opens the mobile application 160 to the device 122.

In block 225 and flow 337, the mobile application opens a received request link including a random ID (ORID) generated by ORID generator 173 and associated by request generator 172 with request 10 for information.

In block 226, and flow 339, the mobile application opens a UI for initiating a second factor authentication (e.g., SMS, telephone call/message, software application, webpage, push notification, email, other side channel or combinations thereof) authenticating the device of the recipient to the autonomous requester 170. The mobile application 160 implements, by presenting a UI to the recipient of the request, a second factor authentication of the recipient to the autonomous requester 170. In an example implementation, when the mobile application 160 is downloaded and run for the first time, opening a request link from a particular requester 170 (some implementations include multiple servers, controlled by different organizations, each sending requests), the mobile application can present the UI for the second factor of authentication, such as e.g. a one-time verification code sent by SMS or telephone call or email. In flow 341, the verification code entered by the user is sent by the mobile application 160 to the requester 170 for authentication. Once this second verification processing is complete, the request recipient has authenticated to the requester 170, and therefore the two-way authentication is complete. The mobile application user can authenticate themselves to the trusted server using any of a variety of techniques such as entry of a passphrase, or certification credential (license information, professional identifier, PIN or other unique code, passphrase, or other credential uniquely identifying the user). Some implementations include checking against a whitelist/blacklist. Some implementations will include prompting for and saving biometric information of the user. In some applications, biometric application is stored by the user on the user's device, and the application request authentication of the user via an operating system facility provided by the mobile device, thereby safeguarding the user's privacy. In some applications, if the user's phone is lost or stolen, authentication is invalidated.

In block 227, public and private key pair is generated by the mobile application and the public key is provided to the requester 170 in flow 343.

In block 228, in flow 345 the public key of the requester 170 is received by the mobile application on behalf of the recipient of the request. These are the credentials that will be used between these two entities for two-way authentication. In some implementations, the keys are used to pass encrypted traffic between requester and application. In some implementations, the keys are used to authenticate the user and server to one another.

In block 229 and flow 347, the mobile application 160 opens the embedded link in the request in the mobile device's web browser 167. The link includes an auth-token (RORPID) that is unique to that request and that authentication. In flow 349, the recipient can enter the requested information into appropriate fields in the request web page 12. When complete, the information is forwarded in flow 351 to the web IF 177 of the request generator 172 of requester 170. In flow 353, the requester 170 commits some information from the request to the blockchain 106. In flow 355 the trusted relationship terminates.

It is noteworthy that in an implementation, when a recipient has already performed actions of blocks 222-228 installing the mobile application and mutually authenticating application and requester, then a notification can be sent directly to the mobile application 160, bypassing the need for switching between email 10 and mobile application 160. One mobile application 160 implementation can present UI for viewing all mutually authenticated requesters, all pending requests, closed requests, etc. Accordingly, implementations of the described technology enable the mobile application 160 to provide portal functionality to the permissioned blockchain ecosystem for the recipient not otherwise authorized to access the blockchain 106 directly.

Having described two-way authentication and messaging operations in a permissioned blockchain ecosystem, the discussion now turns to smart contract implementations.

Use Cases: Report of Problem in Shipment/Finding Like Events

Features and functionality of trusted communications in the blockchain ecosystem 100B, 100C of FIGS. 1B, 1C and 1D implementing a two-way authentication process, can be further understood using an example use case that will be described with reference to FIG. 2D, a flowchart illustrating a method for finding additional instances of like events from a reported first event involving a first physical object in a blockchain network implementing event detection, tracking and management for rule-based compliance leveraging establishing trusted relationship(s) between requester(s) and recipient(s), according to various embodiments.

Accordingly, in the flowchart 200D, at block 231, a trusted server having access permissions to a permissioned blockchain network, receives a report by an unverified source, the report identifying the first physical object.

In a block 232, the trusted server establishes a trusted interactive conversation with the unverified source, the trusted interactive conversation identified by a unique random token, wherein physical parameters of the first physical object are prompted for, and values for the physical parameters are returned.

In a block 233, the trusted server determines from the values for the physical parameters received, values for one or more associated block chain parameters using a machine intelligence process.

In a block 234, the trusted server, using the values for one or more associated block chain parameters, creates a new block chain block.

In a block 235, the trusted server sends the new block chain block populated with at least some of the values for one or more associated block chain parameters in connection with the unique random token to be added to the permissioned blockchain network; thereby enabling other trusted servers with access to the permissioned blockchain network to provide indication of additional instances of like events based upon the values for one or more associated block chain parameters.

Report of Problem in Shipment/Notification of Additional Instances

In a further example use case, the features and functionality of trusted communications in the blockchain ecosystem 100B, 100C of FIGS. 1B, 1C and 1D implementing a two-way authentication process, can be further understood with reference to FIG. 2E, a flowchart illustrating a method for finding additional instances of problem shipments from a problem report of a first damaged shipment in a blockchain network implementing event detection, tracking and management for rule-based compliance leveraging establishing trusted relationship(s) between requester(s) and recipient(s), according to various embodiments.

Accordingly, in the flowchart 200E, at block 241, a trusted server having access permissions to a permissioned blockchain network, receives a report by an unverified source, the report indicating one or more problems with the first damaged shipment.

In a block 242, the trusted server establishes a trusted interactive conversation with the unverified source, the trusted interactive conversation identified by a unique random token, wherein physical parameters of the first damaged shipment are prompted for, and values for the physical parameters are returned.

In a block 243, the trusted server determines from the values for the physical parameters received, values for one or more associated block chain parameters using a machine intelligence process.

In a block 244, the trusted server, using the values for one or more associated block chain parameters, creates a new block chain block.

In a block 245, the trusted server sends the new block chain block populated with at least some of the values for one or more associated block chain parameters in connection with the unique random token to be added to the permissioned blockchain network; thereby enabling other trusted servers with access to the permissioned blockchain network to provide indication of additional instances of problem shipments based upon the values for one or more associated block chain parameters.

Report of Problem in Shipment/Commanded Actions

In another example use case, the features and functionality of trusted communications in the blockchain ecosystem 100B, 100C of FIGS. 1B, 1C and 1D implementing a two-way authentication process, can be further understood with reference to FIG. 2F, a flowchart illustrating a method for initiating commanded actions responsive to reported events in which intervention is desired in a blockchain network implementing event detection, tracking and management for rule-based compliance leveraging establishing trusted relationship(s) between requester(s) and recipient(s), according to various embodiments.

Accordingly, in the flowchart 200F, at block 251, a trusted server having access permissions to a permissioned blockchain network, receives a report by an unverified source, the report indicating one or more problems with the first damaged shipment.

In a block 252, the trusted server establishes a trusted interactive conversation with the unverified source, the trusted interactive conversation identified by a unique random token, wherein physical parameters of the first damaged shipment are prompted for, and values for the physical parameters are returned.

In a block 253, the trusted server determines from the values for the physical parameters received, values for one or more associated block chain parameters using a machine intelligence process.

In a block 254, the trusted server, using the values for one or more associated block chain parameters, creates a new block chain block.

In a block 255, the trusted server sends the new block chain block populated with at least some of the values for one or more of the first state, the first notification to take an action, and the values for the physical parameters in connection with the unique random token to be added to the permissioned blockchain network; thereby enabling other trusted servers with access to the permissioned blockchain network to provide indication of actions taken in connection with additional instances of like events.

Blockchain-Based Chain Code/Smart Contract

Figure 4A:
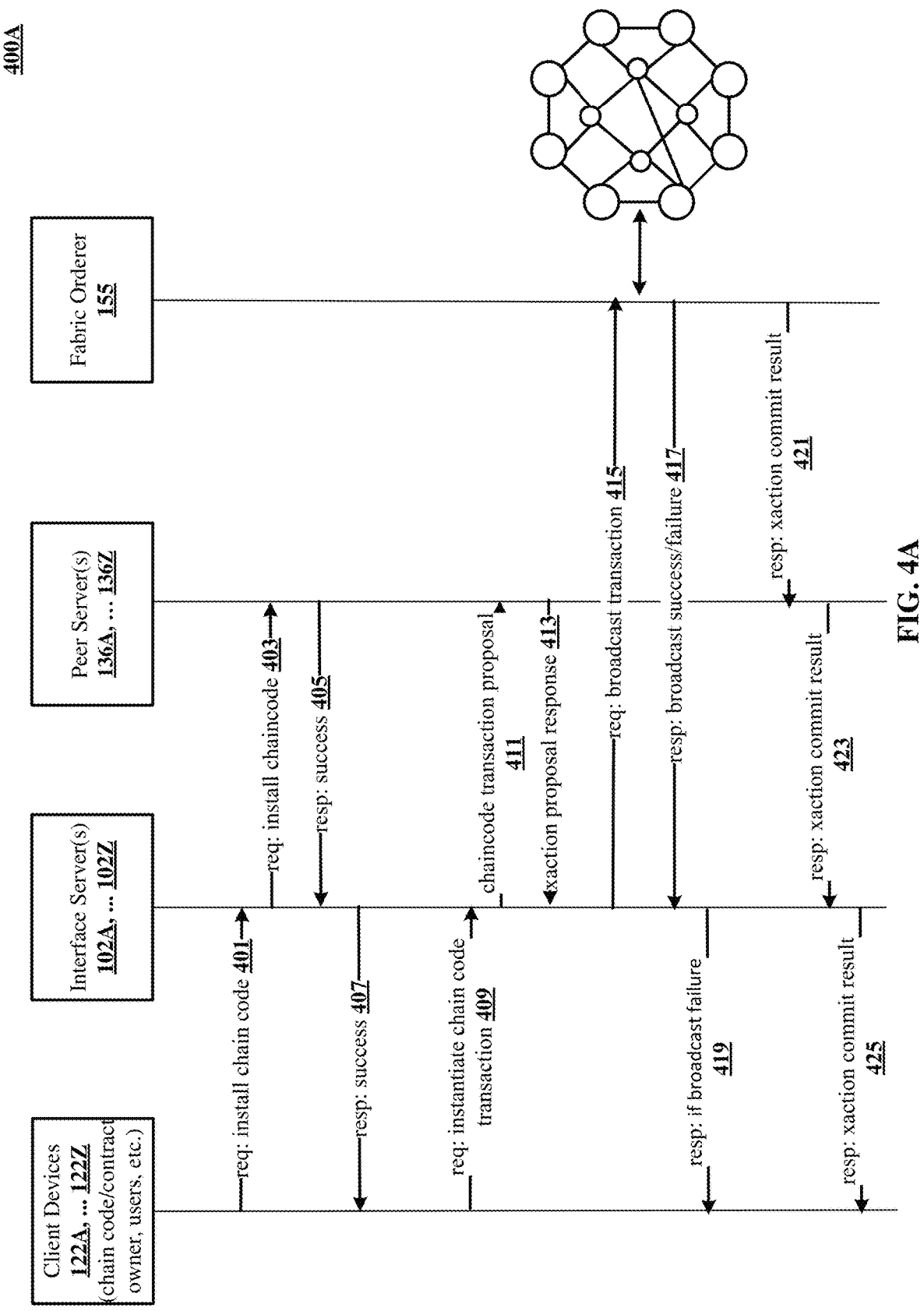
FIG. 4A is a flow diagram 400A depicting an example permissioned blockchain transactions that can be used to implement the technology disclosed.
Figure 4B:
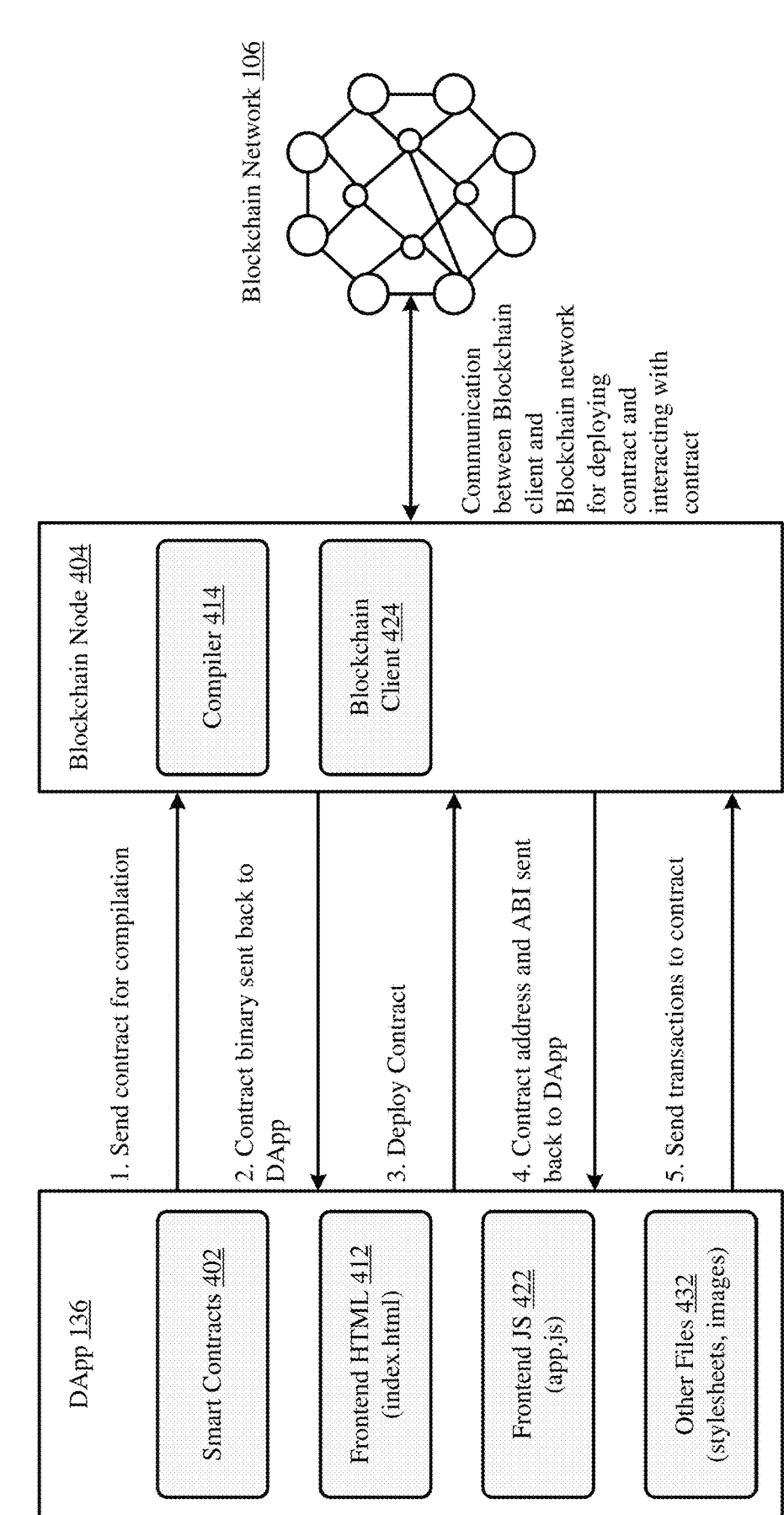
FIG. 4B is a flow diagram 400B depicting an example publicly accessible blockchain transactions that can be used to implement the technology disclosed.

FIG. 4A is a flow diagram 400A depicting an example permissioned blockchain transactions that can be used to implement the technology disclosed. In permissioned blockchain implementations, chain code can be installed onto peer server(s) 136 by interface server(s) 102 using a multiple-phase process.

In an install chain code process (flows 401-407) the source code is uploaded to the peer server(s) 136. There is no effect on the blockchain ledger here. This process is typically initiated via a peer administrator, an automaton identity which has admin privileges on the peer, including privileges to install chain code (i.e., upload source code of the chain code). In a flow 401, a request from the peer admin to install a chain code is received by an interface server(s) 102. Then, in a flow 403, the interface server(s) 102 makes a request to install chain code on the peer server(s) 136. The peer server(s) 136 perform the requested chain code install and reply in a flow 405 with a response indicating the operation was successful (or a failure). In a flow 407, the particular one of the interface server(s) 102 passes the response to the peer administrator that made the install request.

In an instantiate chain code process (flows 409-425) causes the chain code installed previously to be compiled and executed, typically placed in a ready state waiting for transaction requests. This takes the form of a formal transaction conducted upon the blockchain ledger; and it is subject to the same flow and rules. This process is typically initiated via a channel administrator, an automaton identity which has admin privileges on the channel (here, "channel" is another term for the blockchain), including privileges to instantiate chain code (instantiate or upgrade what chain code is running on the channel). In a flow 409, a request from the channel admin to instantiate a chain code is received by an interface server(s) 102. Then, in a flow 411, the interface server(s) 102 makes a chain code transaction proposal to instantiate chain code installed on the peer server(s) 136. The peer server(s) 136 perform instantiating the requested chain code and reply in a flow 413 with a response indicating the operation was successful (or a failure). The interface server(s) 102 makes a request to broadcast the instantiate chain code transaction in a flow 415, which is received by fabric orderer 155. The fabric orderer 155, which executes on a server other than the interface server(s) 102, orders the transaction and adds it to the blockchain ledger and replies in a flow 417 with a response indicating whether the operation was successful (or a failure). In a flow 419, if the broadcast failed, the particular one of the interface server(s) 102 passes the response to the channel administrator that made the install request. In a flow 421, the fabric orderer 155 sends a transaction commit result response to the peer server(s) 136. Peer server(s) 136 then send a transaction commit result response in flow 423 to the particular one of the interface server(s) 102 that initiated the instantiate chain code transaction in flow 411. The particular one of the interface server(s) 102 in flow 425 sends a response transaction commit result indicating the operation was successful (or a failure) to the channel administrator to indicate the outcome of the requested adding the transaction to the blockchain ledger.

In a blockchain access process, such as when a user at client device 122 wants to issue an electronic transaction that affects the blockchain ledger, the structure of this workflow is identical to that of the instantiate chain code process workflow described above with reference to flows 409-425 (since instantiate is just a particular kind of transaction).

FIG. 4B is a flow diagram 400B depicting an example publicly accessible blockchain transactions that can be used to implement the technology disclosed. DApp 136 is used to store the anomaly reports in the tamper-proof blockchain network 106. DApp 136 is decentralized in nature, with no single entity or organization controlling the infrastructure on which the applications are deployed. In the context of Ethereum™, DApp 136 is backed by smart contracts 402 which are deployed on the Ethereum™ blockchain platform that is maintained by the Ethereum™ nodes or peers worldwide. Even though DApp 136 is deployed on a central server which is either a full Ethereum™ node or a can communicate with an Ethereum™ node, the server only serves the DApp's web interface. The DApp logic is controlled by the associated smart contracts 402 which are deployed on the blockchain network 106. DApp 136 provides a friendly interface to smart contracts 402 where the client devices 122 can submit transactions to the contracts from a web interface based on frontend HTML 412, frontend JavaScript (JS) 422, and other files 432 like stylesheets and images. A DApp's web interface forwards the transactions to the blockchain platform and displays the transaction receipts or state information in the smart contracts 402 in the web interface. DApp 136 can use a decentralized messaging protocol such as Whisper™ for communication and decentralized storage platforms such as Swarm™ for static storage.

In example 400B, DApp 136 sends a smart contract to the blockchain node 404 for compilation. Blockchain node 404 comprises a compiler 414 and a blockchain client 424. Compiler 414 can compile smart contracts written in various high-level languages such as Solidity™, Serpent™, and Lisp™. Blockchain client 424 communicates with the blockchain network 106 and performs tasks such as creating accounts and contracts, sending transactions to contracts, and others. Examples of blockchain client devices 424 include geth (written in Go™) and pyethapp (written in Python™).

In response, the blockchain node 404 sends the contract binary to DApp 136. This allows DApp 136 to deploy the contract on the blockchain node 404. Once the contract is deployed, the blockchain node 404 sends a contract address and an application binary interface (ABI) to DApp 136. ABI provides an interface to the state variables and functions defined in the deployed contract. After this, DApp 136 sends transactions to the deployed contract.

FIG. 5 illustrates an example storage block 500 of a blockchain network 106 that implements the technology disclosed. Storage block(s) 500 identifies two related versions of an FDA 3911 report: version 1 is the initial notification and version 2 is the follow-up notification. For each version, the storage block(s) 500 identifies an incident number assigned to the anomaly. In implementations, data too sensitive to risk being stored directly on the blocks of the blockchain network 106 can be stored by Private storage server(s) 156 that access private collections data stored for each organization, which may comprise information of various drug databases (e.g., the FDA Product-Specific Guidance database, which enables searching and clustering by active ingredient(s)) and communications including machine reading of emails on recalls. Interface server(s) 102 is cooperatively coupled with, and permissively enabled to access the private collections stored by private storage server(s) 156 that can comprise multiple sources of data stored by individual organizations that are members of the blockchain network 106, thereby minimizing the need to change notification protocols that can be related to machine-readable data and image recognition (e.g. images of pills).

For example, medical privacy laws such as health insurance portability and accountability act (HIPAA), general data protection regulation (GDPR), and others, legal, regulatory or private, place restrictions on the usage and keeping of data. In such cases, information can be stored locally by participants in the blockchain network 106 in private storage server(s) 156. Addressing information can be pushed by the custodian of the locally stored data, typically in encrypted or other non-human readable form to provide protection from tampering by a single actor and provides for data confidentiality with encryption at the block level.

The storage block(s) 500 can also include hashed addressing information for private storage server(s) 156 that control copies of the potentially private information of other fields of the FDA 3911 form, such as a date of initial notification, name of the product, primary ingredients, etc. that are too sensitive to be included in bock(s) 500; thereby enabling the interface server(s) 102 to obtain this information when permitted and safeguarding this information from public release.

For example, data useful in regulatory compliance reporting stored by private storage server(s) 156 and pointed on by storage block(s) 500, can include without limitation: A type of report (e.g., initial notification, follow-up notification, or request for termination), an incident number (provided by FDA) for follow-up and request for termination, a date of initial notification to FDA (MM/DD/YYYY), a date company determined product was illegitimate (MM/DD/YYYY), a name of product as it appears on the label, primary ingredients, drug use (human, other), a drug description (e.g., finished prescription drug, vaccine, plasma derivative (e.g., coagulation factors, immunoglobulins, albumin), allergenic (e.g., standardized and non-standardized), or multiple), a strength of drug (e.g., 500 mg. 1 g/10 mL), a dosage form (e.g., tablet, capsule, aerosol, oral liquid, sublingual, injectable, topical, suppository, other, or multiple), a quantity of drug (Number and Unit), an NDC (Nat'l Drug Code) number, a serial number, lot number(s), expiration date(s), (for notification) a description of event/issue, (for request for termination of notification) description of why notification is no longer necessary, other reports submitted to the FDA (e.g., FAR—Field Alert Report, BPDR—Biological Product Deviation Report, Medwatch 3500, Medwatch 3500A, none, other), company name and address, company category, manufacturer, wholesale distributer, dispenser (Pharmacy), repackager, Unique Facility Number (D-U-N-S), and contact information.

Output(s) of classifier(s) once trained on a training dataset can also be stored by private storage server(s) 156 and pointed on by storage block(s) 500, can include without limitation: a classification of notification (e.g., counterfeit, diverted, stolen, intentional adulteration, unfit for distribution, fraudulent transaction, others) for a particular situation state.

FIG. 6A illustrates an example workflow 600A in which a smart contract 604A implements the technology disclosed. Workflow 600A illustrates a contract owner 602A creates the smart contract 604A called "Drug Notifications" (e.g., "contract Validator") via an externally owned account (EOA). EOA has a public-private key pair associated with it. The account address (e.g., "address public chairperson") is derived from the public key. When a new EOA is created, a JSON key file is created which has the public and private keys associated with the account. The private key is encrypted with the password which is provided while creating the account. For sending transactions to other accounts, the private key and the account password are required. The contract account is controlled by the associated contract code which is stored with the account. The contract code execution is triggered by transactions sent by the EOA. In some implementations, smart contract 604A can be created by interface servers(s) 102.

Transactions are the electronic messages sent by EOAs to other EOAs or contract accounts. Each transaction includes the address of the recipient, transaction data payload, and a transaction value. When a transaction is sent to an EOA, the transaction value is transferred to the recipient. When a transaction is sent to a contract account, the transaction data payload is used to provide input to the contract function to be executed.

Smart contract 604A is used to store and validate the drug notification reports. Smart contract 604A includes state variables (e.g., "struct Incident", "struct Drug", "Drug[ ] public drugs") that can store and identify different versions of a reporting file. In addition, smart contract 604A also includes state variables (e.g., "struct Assessor", "struct Incident") that can store and identify data origin validation of given version by one or more validators.

Smart contract 604A also includes functions (e.g., "createIncidentReport") that can be used by client devices 122 and interface server(s) 102 to send the FDA forms 3911 to the smart contract 604A and in turn to the blockchain network 106. In implementations, a single function can be used to send FDA forms 3911 for the entire reporting file or separate functions can be used for individual reporting instances of the reporting file. Similarly, smart contract 604A includes functions (e.g., "getIncidentReports") that can be used by client devices 122 and interface server(s) 102 to get the FDA 3911 reports stored on the blockchain network 106. Smart contract 604A also includes functions (e.g., "wasReportValidatedBy") that allow client devices 122 and interface server(s) 102 to validate a report stored on the blockchain network 106. Smart contract 604A also includes functions (e.g., "Validator") that allow client devices 122 and interface server(s) 102 to identify themselves by sending their account addresses to the smart contract 604A.

Figure 6B:
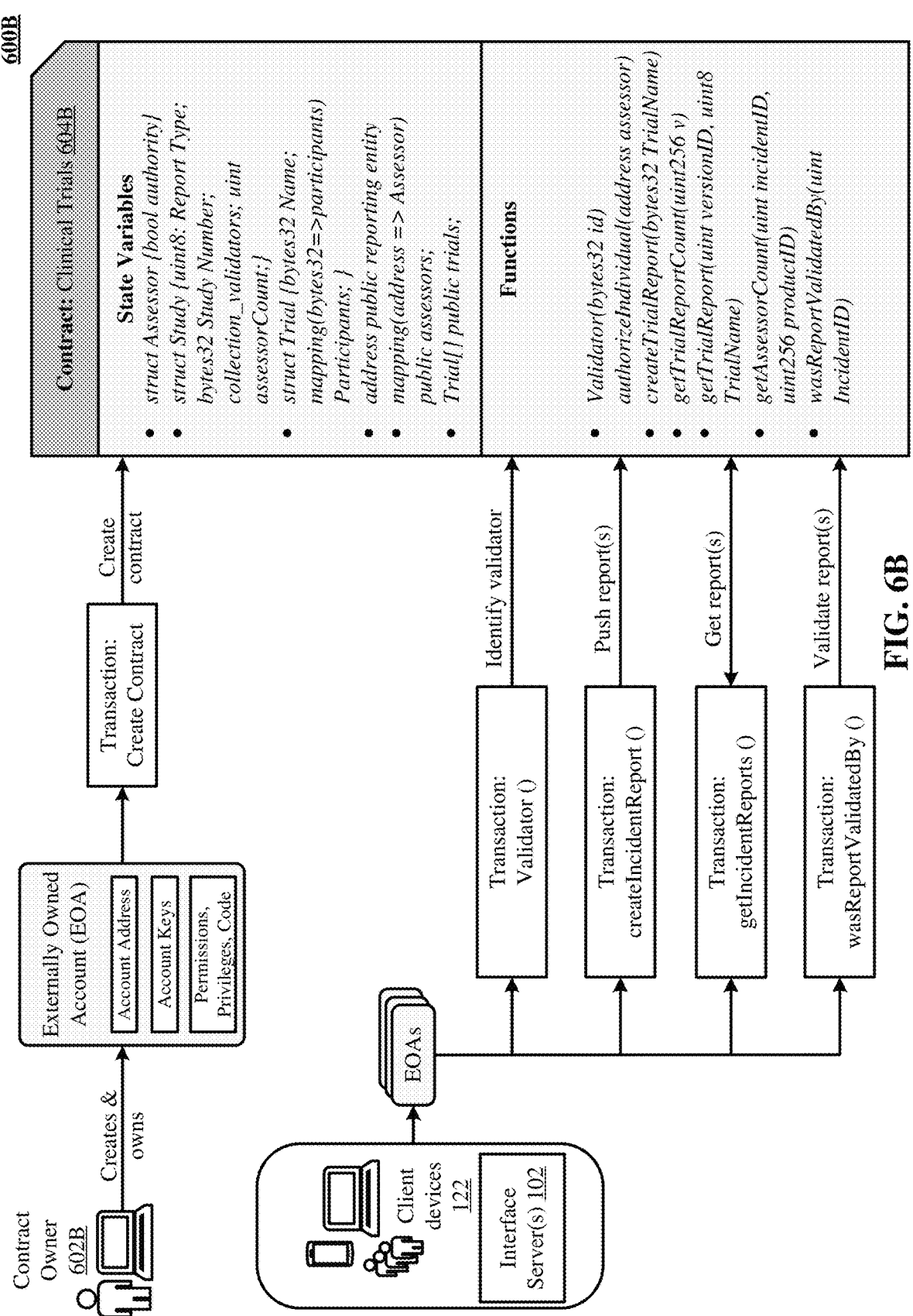
FIG. 6B illustrates an example workflow 600 in which a smart contract 604B implements the technology disclosed.

FIG. 6B illustrates another example workflow 600B in which a smart contract 604B implements the technology disclosed. Workflow 600B illustrates a contract owner 602B creates the smart contract 604B called "Clinical Trials" (e.g., "contract Validator") via an externally owned account (EOA). EOA has a public-private key pair associated with it. The account address (e.g., "address public chairperson") is derived from the public key. When a new EOA is created, a JSON key file is created which has the public and private keys associated with the account. The private key is encrypted with the password which is provided while creating the account. For sending transactions to other accounts, the private key and the account password are required. The contract account is controlled by the associated contract code which is stored with the account. The contract code execution is triggered by transactions sent by the EOA. In some implementations, smart contract 604B can be created by interface server(s) 102.

Transactions are the electronic messages sent by EOAs to other EOAs or contract accounts. Each transaction includes the address of the recipient, transaction data payload, and a transaction value. When a transaction is sent to an EOA, the transaction value is transferred to the recipient. When a transaction is sent to a contract account, the transaction data payload is used to provide input to the contract function to be executed.

Smart contract 604B is used to store and validate the clinical trial reports. Smart contract 604B includes state variables (e.g., "struct Study", "struct Trial", "Trial[ ] public trials") that can store and identify different versions of a reporting file. In addition, smart contract 604B also includes state variables (e.g., "struct Assessor", "struct Study") that can store and identify data origin validation of given version by one or more validators.

Smart contract 604B also includes functions (e.g., "createTrialReport") that can be used by client devices 122 and interface server(s) 102 to send clinical trial reports to the smart contract 604B and in turn to the blockchain network 106. In implementations, a single function can be used to send clinical trial reports for the entire study recording file or separate functions can be used for individual reporting instances of the study recording file. Similarly, smart contract 604B includes functions (e.g., "getTrialReports") that can be used by client devices 122 and interface server(s) 102 to get the clinical trial reports stored on the blockchain network 106. Smart contract 604A also includes functions (e.g., "wasReportValidatedBy") that allow client devices 122 and interface server(s) 102 to validate a report stored on the blockchain network 106. Smart contract 604A also includes functions (e.g., "Validator") that allow client devices 122 and interface server(s) 102 to identify themselves by sending their account addresses to the smart contract 604B.

As time-stamped immutable data structures, blockchains have found utility in cryptocurrency. Unlike a relational database, blockchain network 106 enables implementations to protect data from tampering by a single actor, and/or to provide data confidentiality with encryption at the block level. For additional information on the user of blockchains, reference may be had to U.S. application Ser. No. 15/345,031, entitled Extended Blockchains for Event Tracking and Management, filed Nov. 7, 2016, and U.S. application Ser. No. 15/454,492, entitled Extended Blockchains for Event Tracking and Management, filed Aug. 29, 2016, which applications are incorporated herein in their entirety by reference for all purposes.

Having described smart contract-based implementation of the technology disclosed, the discussion now turns to the interface server(s).

Interface Servers

In one implementation, the interface server(s) 102 are provisioned as clients to the blockchain system 106, provisioned as production server(s) 304, enabling their function to be safe from prying eyes. The challenge for permissioned blockchains within regulated communities is to create a robust community that meets regulatory obligations in near-real-time without simultaneously creating a single point of failure or back-door. Once a single point of failure is created, the blockchain for all intents and purposes becomes a centralized database, whether the architecture is decentralized. Implementation specifics differ; depending on the nature of a particular installation's user and regulatory requirements, the interface server(s) 102 can be configured in different configurations, outlined below.

In an implementation, configurations are based on the relationships between users (e.g. omniscient regulator, board of governors, or root of trust) and the degree of access required for the interface server(s) 102 to be effective (omniscient agent, constrained community-wide agent, or constrained and transparent task-specific agent). The interface server(s) 102 are restricted to only log into the block chain system as a user. Privacy can be enhanced by restricting the interface server(s) database access on the level of a traditional database administrator. As an automaton user, the interface server(s) require no human-readable interface (UX/UI); rather can create notifications to relevant client devices 122 and conducts block-level transactions with blockchain network 106.

In one alternative example, if an interface server implementation only requires publicly accessible data to perform a function (as in the case of Form 3911 outlined below), the core of the interface server(s) logic can be implemented as smart contracts within the blockchain system 106. Such smart contracts, by definition, are auditable by every community member, and provide fine-grained control over what data is ultimately shared with what parties. This control can be ensured through leveraging a combination of data privacy features unique to permissioned blockchains. For instance, building on Hyperledger Fabric, the interface server logic would be implemented as separate chain code, responsible for flagging anomalous transactions or alerting on suspicious correlations. It would be straightforward for an interested party to verify that this chain code cannot be used by any party to query data at-will, and that the notifications are output only to relevant community members. Further control can be exercised by deploying the chain code on separate channels, which allows restricting information sharing between subsets of system participants.

In another alternative example, if an interface server implementation additionally procures private data that does not exist on the blockchain (e.g. from a particular organizations' private storage server(s) 156, then the private source being accessed by the interface server(s) 102 would need to be trusted by all other participants on the blockchain. Though interface server(s) 102 wouldn't necessarily have access to all of an organization's private data, it would be granted access to the requisite set of data needed to function. This could take the form of viewing private collection files to which a given organization granted it access (given rules such as "send interface server all user-submitted images of suspected faulty pill bottles"), or by having more global access to private collections.

As mentioned previously, the first approach would be suitable in the case of the FDA DSCSA. Form FDA 3911 submissions are used by the system users to generate exception reports for suspicious drugs. Each of the fields from the 3911 could be held on the blockchain as a separate variable. Interface server(s) flag any identical entries in any fields (e.g. two matches may be adequate for a notification involving a controlled substance, perhaps three for a less dangerous medicine) for further escalation in a smart manner. For example, if a Walgreens dispenser in Chicago says that Oxycontin lot #5667777 looks wrong and CVS in Woonsocket reports a problem with the same lot, the escalation by the interface server(s) 102 might trigger them sending a fresh notification to the manufacturer and FDA, indicating that this lot has multiple reporters reporting a problem. Under the current Form 3911 system, the manufacturer and FDA would receive two different notifications from two different reporters and have to collate them manually off-line.

In an implementation, the interface server(s) 102 accesses smart contracts that can invoke follow-up notifications to the reporting entity or entities. The submitting or reporting entity might be asked to take a picture of the goods in question, or confirm their whereabouts, or ask to describe symptoms. They might also be asked to quarantine suspicious materials, or mail them to the CDC, or hold for pickup by the DEA.

With a notification from participating interface server(s), the FDA can then post a Medwatch notification or call the manufacturer and ask for clarification. Alternatively, a manufacturer might proactively ask for quarantine. For especially sensitive products such as fentanyl, the system could quarantine all transactions for that lot for 24 hours while humans at the manufacturer and FDA discuss their options.

This implementation is part of a broader initiative to develop a system of blockchain-validated reporting, resolution and root cause analysis. The implementations illustrated by FIGS. 7A, 7B implement tracking and responding in near-real-time to out-of-spec asset reports in critically important supply scenarios and managing access to clinical trial information, respectively.

Having described smart contract-based implementation of the technology disclosed, the discussion now turns to some example use cases.

Example Use Case

Figure 7A:
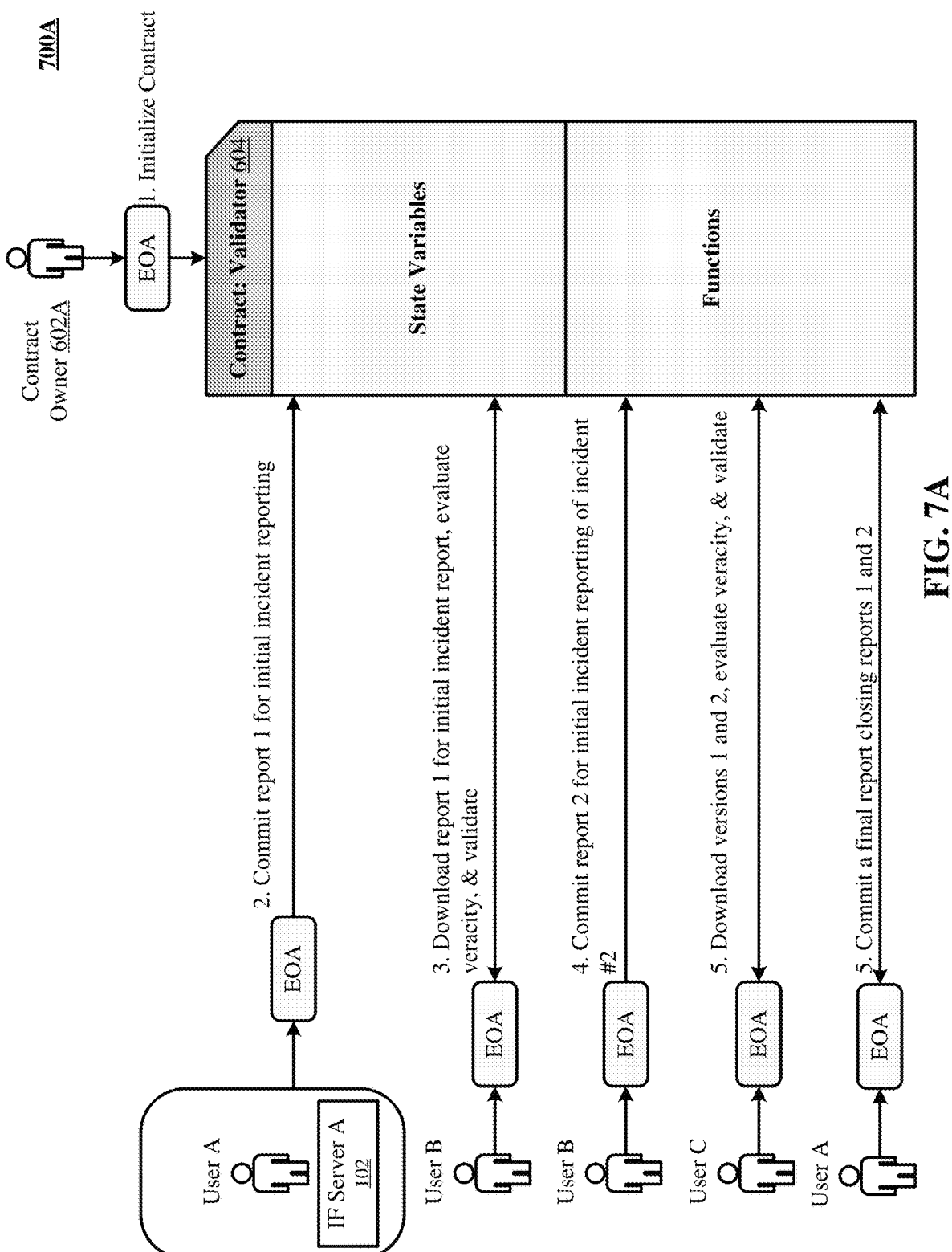
FIGS. 7A, 7B depict example use cases 700A, 700B.

FIG. 7A depicts an example use case 700A in which the smart contract 604A of FIG. 6A is used to securely authenticate an incident reporting file from initial collection through resolution. The technology disclosed provides a way to securely authenticate an incident reporting file from initial collection through post-resolution. Consider that a first actor affiliated with a regulatory enforcement agency for example, uses a client device 122 to create a smart contract 604A on the blockchain network 106 with a policy goal of ensuring data integrity and creating a provenance trail of evidentiary data collection of an incident event. If a seal is broken on a pill bottle, for example, a dispenser (pharmacy) is required to categorize and report the problem via an FDA form 3911 within 24 hours. The initial incident report can be prepared and submitted by one of client devices 122, authorized to submit such reports on behalf of the dispenser (or warehouse encountering a damaged shipment, etc.) using a digital device or address under their control to invoke the interface server 102. In the case of the FDA DSCSA, FDA form 3911 submissions are used by the system users to generate exception reports for suspicious drugs. Each of the fields from the 3911 can be held on the blockchain as a separate variable. Interface server 102 flags any identical entries in any fields (e.g. two matches may be adequate for a notification involving a controlled substance, perhaps three for a less dangerous medicine) for further escalation.

To persist and authenticate the origin of the report, a first custodian (e.g., user A) using the guided screens driven by deep neural network(s) 1334 can collect and input information into the application required to prepare FDA form 3911 and upload the report to smart contract 604A. These inputs can be stored on the blockchain network 106 as a report of the incident along with the credentials of user A.

Accordingly, when another user B, such as a pharmacy in a neighboring county, receives a local copy of the report from the regulatory enforcement agency, to ensure that the original information has not been tampered with, user B can generate for the local copy of the report and compare it with those stored on the blockchain network 106 as report 1. This may require the regulatory enforcement agency giving user B access to smart contract, in addition to the report (which can be provided separately). For example, if a Walgreens dispenser in Chicago reports that Oxycontin lot #5667777 looks wrong, a CVS in Woonsocket (user B) compares their local copy and the blockchain version. User B can determine the veracity of the local copy. If local copy is unaltered, user B can validate report 1 and store the validation on the blockchain network 106 appended to report 1 so that other users can see that report 1 has been validated by another user.

It is often the case that exceptions affecting one shipment will also affect other shipments in the lot. User B examines their stock for similar discrepancies. User B upon investigation discovers a problem with the same lot, user B can generate a report for any exceptions that they find in their stock and commit the report to the blockchain network 106 as a second report. Detecting identical problems causes interface server 102 of user B to escalate the problem, triggering a notification to the manufacturer and FDA, indicating that this lot has multiple reporters reporting a problem.

This may motivate another user C, such as a manufacturer, to compare the report 1 and report 2, verify the chain of custody all the way back to the point of origin, and validate that report 2 is related to the same problem as report 1. In implementations, prior versions of a current version can be stored. This way, a provenance trail of the chain of custody can be stored and presented using smart contract 604A.

Figure 7B:
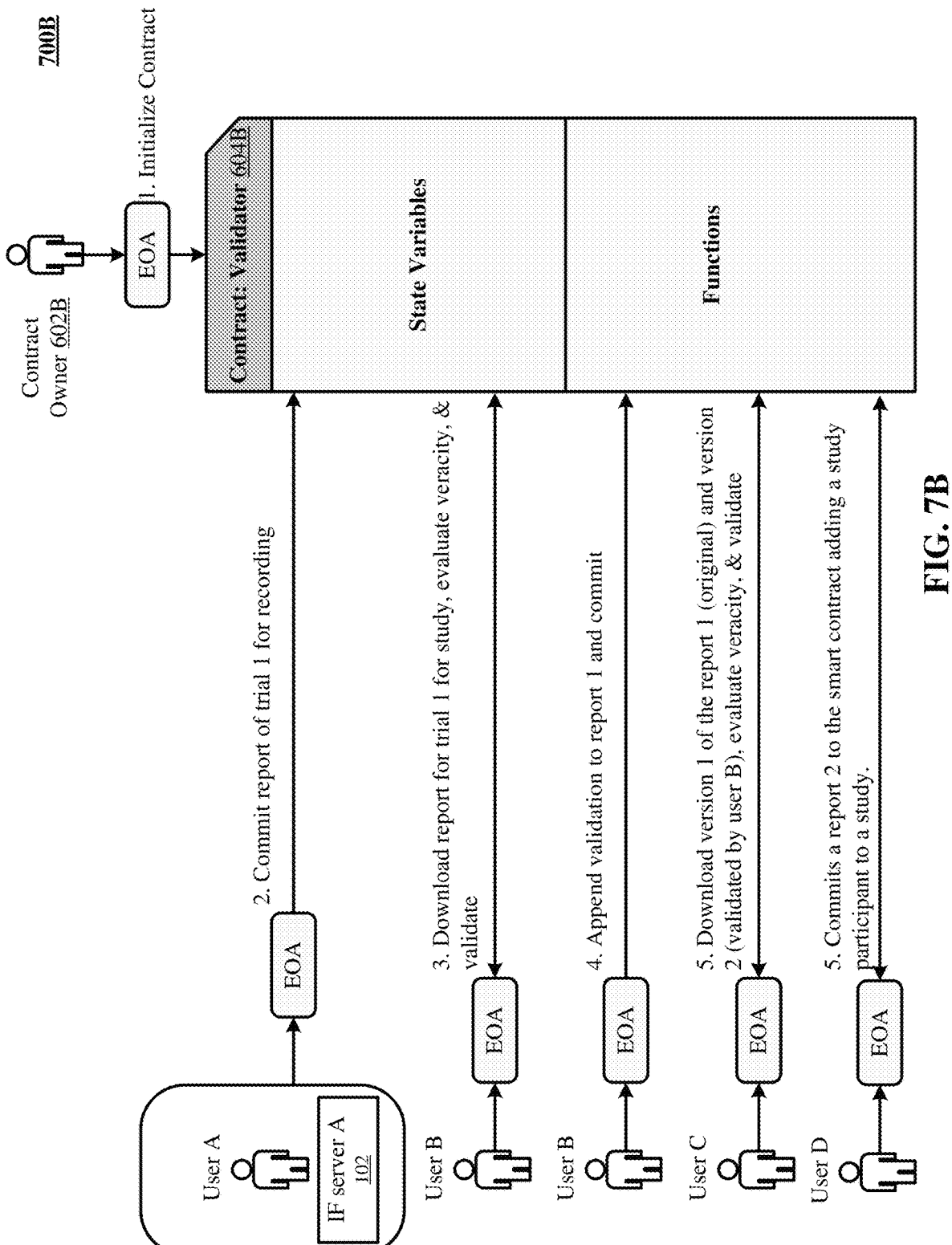

FIG. 7B depicts an example use case 700B in which the smart contract 604B of FIG. 6B is used to securely authenticate a clinical study recording file from initiating the study to collection of trial data throughout the study to completion. The technology disclosed provides a way to securely authenticate a clinical study recording file from initiation through post-completion. Consider that a first actor, contract owner 602B uses a client device 122 to create smart contract 604B on the blockchain network 106. The first actor can be affiliated with a clinical lab, hospital, research institution, or governmental or non-governmental agency with a policy goal of ensuring data integrity and creating a provenance trail of evidentiary data collection of trials conducted in furtherance of the clinical study. Subsequently, an initial trial report can be prepared and submitted using one of client devices 122, that has been authorized to submit such reports on behalf of the clinic (or research lab, hospital, etc.) using a digital device or address under their control to invoke an instance of interface server 102. Trial report submissions are used by the system users A, B, C, etc. to generate records for trials being conducted in furtherance of the study. Each of the fields from the study record can be held on the blockchain as a separate variable. Interface server(s) 102 flags any identical entries in any fields (e.g. two matches may be adequate for trial IDs in recordings of trials, perhaps three for variables in which some duplicity is expected).

To persist and authenticate the origin of the record, a first custodian (e.g., user A) using the guided screens driven by learning model(s) 134 can collect and input information into the application required to prepare and upload the record of a particular trial to smart contract 604B corresponding to a particular study. These inputs can be stored on the blockchain network 106 as a report of the trial along with the credentials of user A.

When another user B, such as a scientist conducting a clinical trial, receives a local copy of the report from user A of trial 1, to ensure that the original information has not been tampered with, user B can generate an encrypted version for the local copy of the report and compare it with those stored on the blockchain network 106 as report of trial 1. An interface server(s) 102 invokes contract validator 604B to determine whether user B has been granted permission to view the report 1 including patient related data portions. Permission may have been given by the research lab, governmental agency or non-governmental agency that acts as contract owner 602B of the study. This can require the contract owner 602B giving user B access to smart contract 604B, in addition to the report (which can be provided separately). For example, if report 1 includes patient related data, the interface server(s) 102 compares the role of user B with the access permissions required to view the report 1, by determining whether the request is made by a participant in a clinical trial or a scientist conducting a clinical trial. Interface server(s) 102 then permits access to the participant of a subset of the clinical trial information suitable for the participant, otherwise permitting access to the scientist of a different subset of the clinical trial information suitable for the scientist. User B, being a scientist in this case, encrypts their local copy and compares it to the blockchain version, enabling user B can determine the veracity of the local copy. If local copy is unaltered, user B can validate report 1 and store the validation on the blockchain network 106 appended to report 1 so that other users can see that report 1 has been validated by another user. On the other hand, if user B were a study participant, rather than a scientist, interface server(s) 102 would permit user B access only to portions of the block-level data in the report 1 suitable to a participant in the trial.

Another user C, such as a scientist in a different facility that is also conducting trials, might download report 1 and compare the original version of report 1 with the version of report 1 with validation appended to it by user B, verifying the chain of custody all the way back to the point of origin, and validating that report 1 version 2 is related to the same trial as report 1, original version. In implementations, prior versions of a current version can be stored. This way, a provenance trail of the chain of custody can be stored and presented using smart contract 604B.

Another scientist, user D, requests to add a patient to a trial in the study using their client device 122 locates a block on the chain in which some patient data of the request relates. The interface server(s) 102 using smart contract 604B determines whether the request is authorized under a smart contract governing the use of the clinical trial blockchain; and adds the patient to the clinical trial whenever the request is authorized.

Figure 8B:
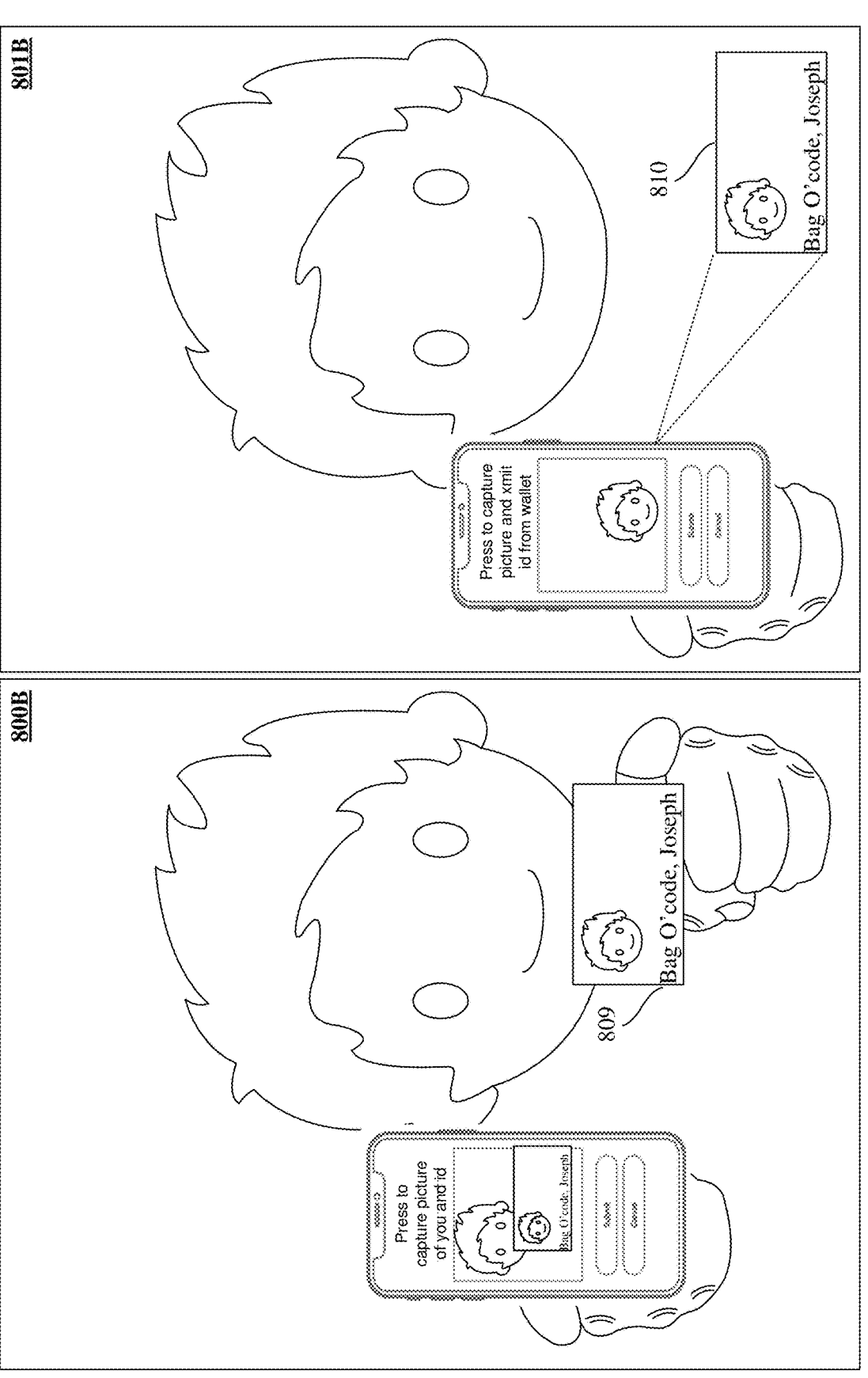

One implementation includes a mobile application that executes as a client on one or more client device(s) 122, displaying panels as triggered by the interface server(s) 102 when backed by a blockchain network 106, captures barcodes on questionable package and video, audio or other sensed information. A representative usage scenario of a mobile application to authenticate user's to access the blockchain is next described with reference to FIGS. 8A-8E.
Documentation Collection FIGS. 8A-8E depict examples of authentication documentation submissions 800. In FIG. 8A, examples 800A, 801A depict a series of prompts displayed by application 160 to a user in a representative usage scenario for submitting supporting documentation. In both of the cases 800A, 801A shown in FIG. 8A, the user is a licensed pharmacist in the United States. In case 800A, the user will authenticate themselves with the system by capturing a picture of themselves holding a traditional government issued id (e.g., drivers license, passport, etc.). In case 801A, the user will authenticate themselves with the system by capturing a picture of themselves and providing contemporaneously, a link to a government issued id from the user's digital wallet (e.g., Apple wallet™, Google wallet™, or the like). Additional (or different) supporting information may be required depending on the nature of the credential and the requirements of the trust framework. In some embodiments, the documentation supporting authentication is archived electronically. Privacy data store 195 can provide storage off-chain for private documentation, i.e., containing personally identifiable information, in which each member's supporting documentation is stored in an auditable format. Such documentation can be made available by authentication server 190 specifically to an auditor, e.g., an enterprise-level accreditor or a third-party accreditor, via validator server 180. This accreditor performs checking of credentials and documents, to support/verify the individual's claim that they are indeed the person they claim to be. In some implementations a neural network is trained to perform the accreditation functionality. Training sets to train the neural network can include both correct conclusions as well as false conclusions.

In FIG. 8B, an example image capture 800B of a user seeking to authenticate with the system using the mobile application 160 on their client device 122 as shown responsive to the prompts in screen 800A of FIG. 8A. In the example implementation illustrated, the applicant is prompted to take a photo of themselves using their device 122 with their driver's license 809 in the self-same photo upon request to be ingested directly into the application 160 for remote storage by authentication server 190. Supplemental asks in some embodiments can include to invert or flip the license, or to wink or to hold the license with only the thumb showing 809. In addition, some implementations call for the mobile application 160 to pose questions to the applicant through a secure channel and collect responses. Other forms of biometric markers can also be captured by the application 160 as part of the documentation, such as for example, user fingerprint(s) or other body images, voice or whistling samples or records, retinal scans/prints, iris scans/prints, palm features, typing dynamics (//en.wikipedia.org/wiki/Keystroke_dynamics) and the like. With continuing reference to FIG. 8B, an alternative example of image capture 801B by a user seeking to authenticate with the system using the mobile application 160 on their client device 122 responsive to the prompts in screen 801A of FIG. 8A is shown. In the example implementation 801B illustrated, the applicant is prompted to take a photo of themselves using their device 122 and to provide a link to a government issued id 810 from the user's digital wallet (e.g., Apple wallet™, Google wallet™, or the like). The documentation captured by either process 800B, 801B, which includes personal information, may be archived under control of the authentication server 190 as indicated by the trust framework governing the implementation; however, the personal data can also be expunged without a trace upon the request of the individual upon their withdrawal from the community to satisfy legal requirements in certain jurisdictions (e.g., GDPR, etc.). The mobile application 160 will receive this information and sends this information from the client device 122 to the authentication server 190 via the network(s) 101. In one implementation, the application information and supporting documentation is then sent to the accreditor for review via email.

In FIG. 8C, screen 800C illustrates an example of an email sent from the mobile application 160 of client device 122 to the authentication server 190 with the original applicant's photos as captured. Some configurations implement a third-party accreditation to enhance security as opposed to relying only on a member enterprise to issue its own credentials. The email contains core documentation, including an embedded image and link to the photo of the applicant with their driver's license. In some implementations, the image's source link is pre-configured to expire so it is no longer accessible to the third-party accreditor. Now with reference to FIG. 8D, screen 800D illustrates the example email of FIG. 8C in which the links to the photos have expired or been redacted by the registry server 190 in furtherance of protecting privacy. In one implementation, links expire in seven (7) days, however, other implementations the expiration time can be in a range of from one day to several months. One implementation includes expiration dates of from one (1) day to one (1) month, another implementation includes expiration dates of from one (1) month to four months. Other non-public attributes can be converted into externally hosted images, with access rescinded after a set period of time to protect personally identifiable information of the requestor. In some implementations, the photographs may be redacted after expiry of a period of time after the documentation is sent to the accreditor. In one implementation, photos are shown to the accreditor through a link that is subsequently severed. When email is implemented as the communications vehicle with the accreditor, the email does not have a photograph attached; rather a link to a photograph that expires is included. Accordingly, the accreditor has only temporary access to the documentation and no permanent storage of PII is needed nor implemented. Further, some implementations will include other additional prompts facilitating different actions.

One example of one type of follow up prompting triggered by interface server(s) 102, in some embodiments, is the authenticating registry server 190 many trigger questions to be asked of the requestor/applicant through a secure channel. The documentation collected, which includes personal information, may be archived in privacy data store 195 as required by the trust framework; but in implementations of our disclosed technology, the personal data can also be expunged from privacy data store 195 without a trace upon the request of the individual upon their withdrawal from the community.

Figure 8E:
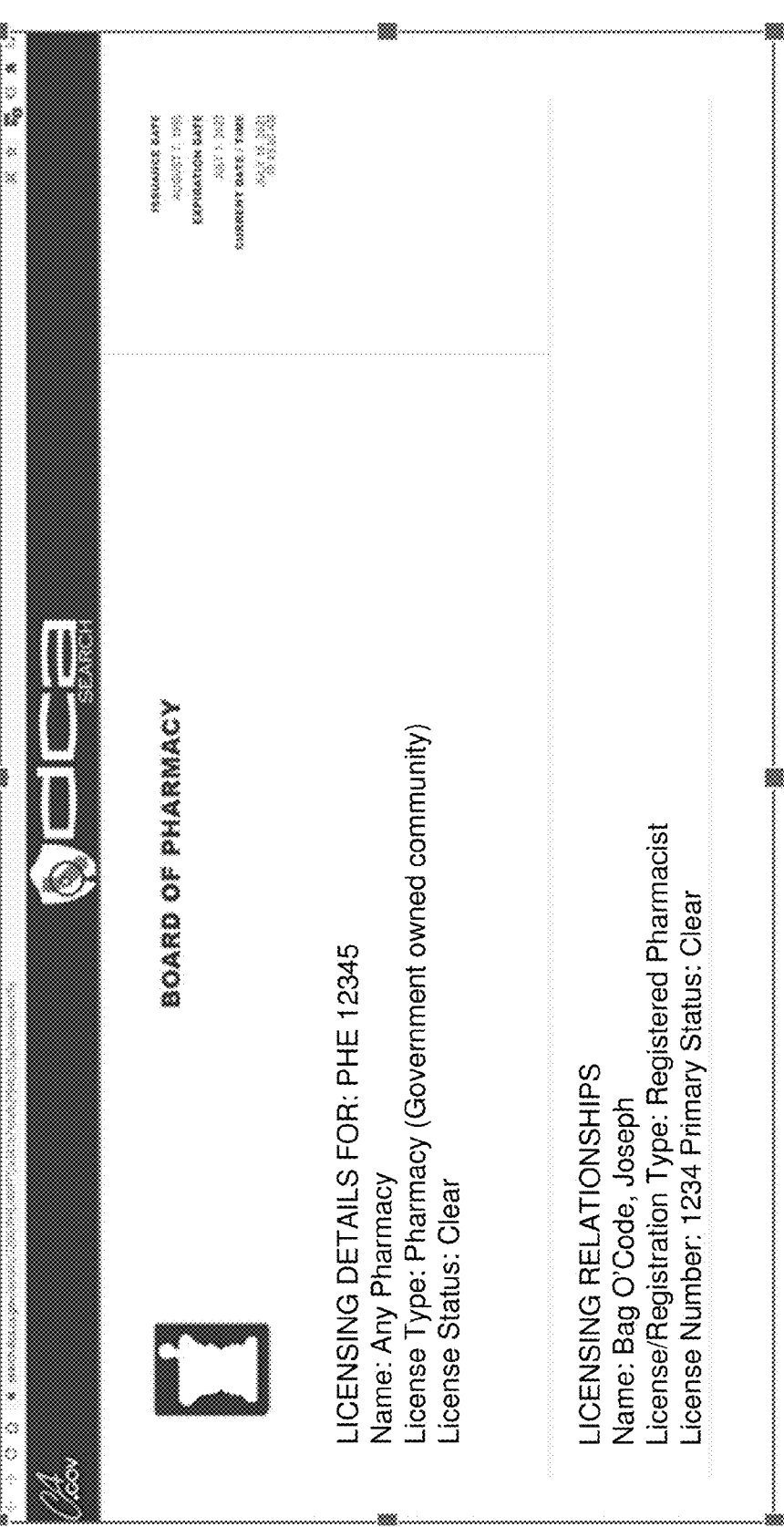

FIG. 8E, depicting a screen 800E shows one such means of submitting supporting documentation from an accreditation authority 185 of FIG. 1A; in this case, for a licensed pharmacist in the United States. Additional (or different) supporting information may be required depending on the nature of the credential and the requirements of the trust framework. In this way, the individual is tied to a member organization within the enterprise or community. The private messages and data, but not the PII, may be shared with fellow members of that organization. In addition, the private data may survive the disconnection of the member ("right to be forgotten") if the organization survives the member. For example, if UCLA Health, implementing our disclosed technology, employs a pharmacist and sponsors their membership, and that pharmacist subsequently retires, their prescriptions can survive that retirement event, even though their personally identifiable information is removed.

Computer System

FIG. 9 illustrates one implementation of a computer system 900 that can be used to implement the technology disclosed. Computer system 900 includes at least one central processing unit (CPU) 972 that communicates with a number of peripheral devices via bus subsystem 955. These peripheral devices can include a storage subsystem 910 including, for example, memory devices and a file storage subsystem 936, user interface input devices 938, user interface output devices 976, and a network interface subsystem 974. The input and output devices allow user interaction with computer system 900. Network interface subsystem 974 provides an interface to outside networks, including an interface to corresponding interface devices in other computer systems. The analyzer and deep learning system can be communicably linked to the storage subsystem 910 and the user interface input devices 938.

User interface input devices 938 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 900.

User interface output devices 976 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 900 to the user or to another machine or computer system.

Storage subsystem 910 stores programming and data constructs that provide the functionality of some or all of the modules and methods described herein. These software modules are generally executed by deep learning processors 978.

Deep learning processors 978 can be graphics processing units (GPUs) or field-programmable gate arrays (FPGAs). Deep learning processors 978 can be hosted by a deep learning cloud platform such as Google Cloud Platform™, Xilinx™, and Cirrascale™. Examples of deep learning processors 978 include Google's Tensor Processing Unit (TPU)™, rackmount solutions like GX4 Rackmount Series™, GX2 Rackmount Series™, NVIDIA DGX-1™ Microsoft™ Stratix V FPGA™, Graphcore's Intelligent Processor Unit (IPU)™, Qualcomm's Zeroth Platform™ with Snapdragon processors™, NVIDIA's Volta™, NVIDIA's DRIVE PX™ NVIDIA's JETSON TX1/TX2 MODULE™, Intel's Nirvana™, Movidius VPU™, Fujitsu DPI™, ARM's DynamicIQ™, IBM TrueNorth™, and others.

Memory subsystem 922 used in the storage subsystem 910 can include a number of memories including a main random access memory (RAM) 932 for storage of instructions and data during program execution and a read only memory (ROM) 934 in which fixed instructions are stored. A file storage subsystem 936 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 936 in the storage subsystem 910, or in other machines accessible by the processor.

Bus subsystem 955 provides a mechanism for letting the various components and subsystems of computer system 900 communicate with each other as intended. Although bus subsystem 955 is shown schematically as a single bus, alternative implementations of the bus subsystem can use multiple busses.

Computer system 900 itself can be of varying types including a personal computer, a portable computer, a work-station, a computer terminal, a network computer, a televi-sion, a mainframe, a server farm, a widely-distributed set of loosely networked computers, or any other data processing system or user device. Due to the ever-changing nature of computers and networks, the description of computer system 900 depicted in FIG. 9 is intended only as a specific example for purposes of illustrating the preferred embodiments of the present invention. Many other configurations of computer system 900 are possible having more or less components than the computer system depicted in FIG. 9.

Convolutional Neural Networks

A convolutional neural network is a special type of neural network. The fundamental difference between a densely connected layer and a convolution layer is this: Dense layers learn global patterns in their input feature space, whereas convolution layers learn local patters: in the case of images, patterns found in small 2D windows of the inputs. This key characteristic gives convolutional neural networks two inter-esting properties: (1) the patterns they learn are translation invariant and (2) they can learn spatial hierarchies of pat-terns.

Regarding the first, after learning a certain pattern in the lower-right corner of a picture, a convolution layer can recognize it anywhere: for example, in the upper-left corner. A densely connected network would learn the pattern anew if it appeared at a new location. This makes convolutional neural networks data efficient because they need fewer training samples to learn representations they have gener-alization power.

Regarding the second, a first convolution layer can learn small local patterns such as edges, a second convolution layer will learn larger patterns made of the features of the first layers, and so on. This allows convolutional neural networks to efficiently learn increasingly complex and abstract visual concepts.

A convolutional neural network learns highly non-linear mappings by interconnecting layers of artificial neurons arranged in many different layers with activation functions that make the layers dependent. It includes one or more convolutional layers, interspersed with one or more sub-sampling layers and non-linear layers, which are typically followed by one or more fully connected layers. Each element of the convolutional neural network receives inputs from a set of features in the previous layer. The convolu-tional neural network learns concurrently because the neu-rons in the same feature map have identical weights. These local shared weights reduce the complexity of the network such that when multi-dimensional input data enters the network, the convolutional neural network avoids the com-plexity of data reconstruction in feature extraction and regression or classification process.

Convolutions operate over 3D tensors, called feature maps, with two spatial axes (height and width) as well as a depth axis (also called the channels axis). For an RGB image, the dimension of the depth axis is 3, because the image has three color channels; red, green, and blue. For a black-and-white picture, the depth is 1 (levels of gray). The convolution operation extracts patches from its input feature map and applies the same transformation to all of these patches, producing an output feature map. This output feature map is still a 3D tensor: it has a width and a height. Its depth can be arbitrary, because the output depth is a parameter of the layer, and the different channels in that depth axis no longer stand for specific colors as in RGB input; rather, they stand for filters. Filters encode specific aspects of the input data: at a height level, a single filter could encode the concept "presence of a face in the input," for instance.

For example, the first convolution layer takes a feature map of size (28, 28, 1) and outputs a feature map of size (26, 26, 32): it computes 32 filters over its input. Each of these 32 output channels contains a 26×26 grid of values, which is a response map of the filter over the input, indicating the response of that filter pattern at different locations in the input. That is what the term feature map means: every dimension in the depth axis is a feature (or filter), and the 2D tensor output [:, :, n] is the 2D spatial map of the response of this filter over the input.

Convolutions are defined by two key parameters: (1) size of the patches extracted from the inputs—these are typically 1×1, 3×3 or 5×5 and (2) depth of the output feature map— the number of filters computed by the convolution. Often these start with a depth of 32, continue to a depth of 64, and terminate with a depth of 128 or 256.

Figure 10:
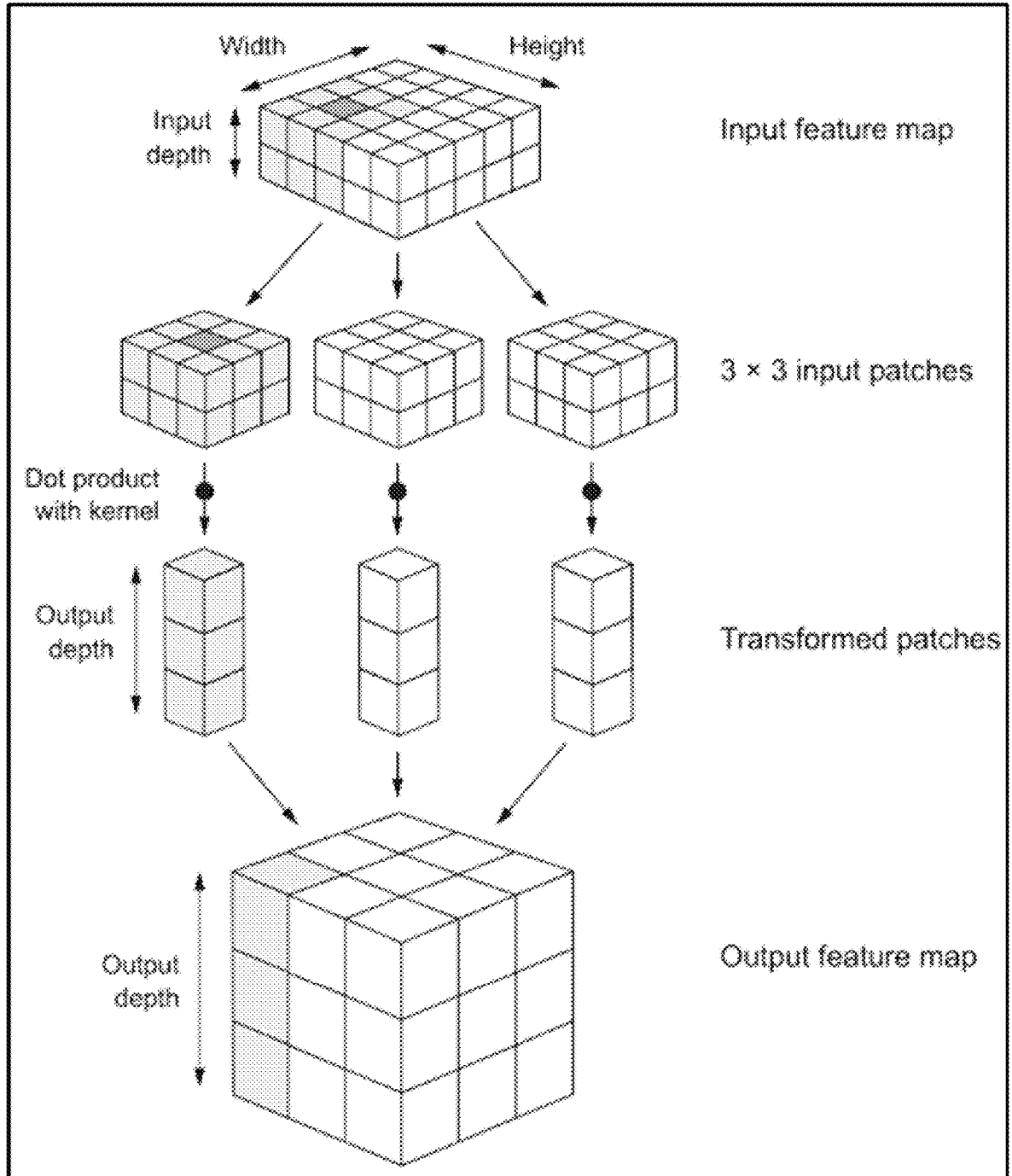
FIG. 10 illustrates an implementation of a convolutional neural network suitable for implementing the disclosed technology.

A convolution works by sliding these windows of size 3×3 or 5×5 over the 3D input feature map, stopping at every location, and extracting the 3D patch of surrounding features (shape(window_height, window_width, input_depth)). Each such 3D patch is ten transformed (via a tensor product with the same learned weight matrix, called the convolution kernel) into a 1D vector of shape (output_depth). All of these vectors are then spatially reassembled into a 3D output map of shape (height, width, output_depth). Every spatial loca-tion in the output feature map corresponds to the same location in the input feature map (for example, the lower-right corner of the output contains information about the lower-right corner of the input). For instance, with 3×3 windows, the vector output [i, j, :] comes from the 3D patch input [i−1: i+1, j−1:J+1, :]. The full process is detailed in FIG. 10, illustrating an implementation of a convolutional neural network suitable for implementing the disclosed technology.

The convolutional neural network comprises convolution layers which perform the convolution operation between the input values and convolution filters (matrix of weights) that are learned over many gradient update iterations during the training. Let (m, n) be the filter size and W be the matrix of weights, then a convolution layer performs a convolution of the W with the input X by calculating the dot product W·x+b, where x is an instance of X and b is the bias. The step size by which the convolution filters slide across the input is called the stride, and the filter area (m×n) is called the receptive field. A same convolution filter is applied across different positions of the input, which reduces the number of weights learned. It also allows location invariant learning, i.e., if an important pattern exists in the input, the convolution filters learn it no matter where it is in the sequence.

Training a Convolutional Neural Network

FIG. 11 depicts a block diagram of training a convolu-tional neural network in accordance with one implementa-tion of the technology disclosed. The convolutional neural network is adjusted or trained so that the input data leads to a specific output estimate. The convolutional neural network is adjusted using back propagation based on a comparison of the output estimate and the ground truth until the output estimate progressively matches or approaches the ground truth.

The convolutional neural network is trained by adjusting the weights between the neurons based on the difference between the ground truth and the actual output. This is mathematically described as:

$$\Delta w_i = x_i \delta$$

where $\delta$ = (ground truth)−(actual output)

In one implementation, the training rule is defined as:

$$w_{nm} \leftarrow w_{nm} + \alpha(t_m - \varphi_m)a_n$$

In the equation above: the arrow indicates an update of the value; $t_m$ is the target value of neuron m; $\varphi_m$ is the computed current output of neuron m; $a_n$ is input n; and $\alpha$ is the learning rate.

The intermediary step in the training includes generating a feature vector from the input data using the convolution layers. The gradient with respect to the weights in each layer, starting at the output, is calculated. This is referred to as the backward pass, or going backwards. The weights in the network are updated using a combination of the negative gradient and previous weights.

In one implementation, the convolutional neural network uses a stochastic gradient update algorithm (such as ADAM) that performs backward propagation of errors by means of gradient descent. One example of a sigmoid function based back propagation algorithm is described below:

$$\varphi = f(h) = \frac{1}{1 + e^{-h}}$$

In the sigmoid function above, h is the weighted sum computed by a neuron. The sigmoid function has the following derivative:

$$\frac{\partial \varphi}{\partial h} = \varphi(1 - \varphi)$$

The algorithm includes computing the activation of all neurons in the network, yielding an output for the forward pass. The activation of neuron m in the hidden layers is described as:

$$\varphi_m = \frac{1}{1 + e^{-hm}}$$

$$h_m = \sum_{n=1}^{N} a_n w_{nm}$$

This is done for all the hidden layers to get the activation described as:

$$\varphi_k = \frac{1}{1 + e^{hk}}$$

-continued $$h_k = \sum_{m=1}^{M} \varphi_m v_{mk}$$

Then, the error and the correct weights are calculated per layer. The error at the output is computed as:

$$\delta_{ok} = (t_k - \varphi_k)\varphi_k(1 - \varphi_k)$$

The error in the hidden layers is calculated as:

$$\delta_{hm} = \varphi_m(1 - \varphi_m)\sum_{k=1}^{K} v_{mk}\delta_{ok}$$

The weights of the output layer are updated as:

$$vmk \leftarrow \nabla vmk + \alpha \delta ok \varphi m$$

The weights of the hidden layers are updated using the learning rate $\alpha$ as:

$$vnm \leftarrow wnm + \alpha \delta hman$$

In one implementation, the convolutional neural network uses a gradient descent optimization to compute the error across all the layers. In such an optimization, for an input feature vector x and the predicted output $\hat{y}$, the loss function is defined as l for the cost of predicting $\hat{y}$ when the target is y, i.e. $l(\hat{y}, y)$. The predicted output $\hat{y}$ is transformed from the input feature vector x using function $f$. Function $f$ is parameterized by the weights of convolutional neural network, i.e. $\hat{y} = f_w(x)$. The loss function is described as $l(\hat{y}, y) = l(f_w(x), y)$, or $Q(z, w) = l(f_w(x), y)$ where z is an input and output data pair (x, y). The gradient descent optimization is performed by updating the weights according to:

$$V_{t+1} = \mu V_t - \alpha \frac{1}{n}\sum_{i=1}^{N} \nabla w_t Q(z_t, w_t)$$

$$W_{t+1} = W_t + V_{t+1}$$

In the equations above, $\alpha$ is the learning rate. Also, the loss is computed as the average over a set of n data pairs. The computation is terminated when the learning rate $\alpha$ is small enough upon linear convergence. In other implementations, the gradient is calculated using only selected data pairs fed to a Nesterov's accelerated gradient and an adaptive gradient to inject computation efficiency.

In one implementation, the convolutional neural network uses a stochastic gradient descent (SGD) to calculate the cost function. A SGD approximates the gradient with respect to the weights in the loss function by computing it from only one, randomized, data pair, $z_t$, described as:

$$v_{t+1} = \mu V - \alpha \nabla wQ(z_t, w_t)$$

$$W_{t+1} = W_t + V_{t+1}$$

In the equations above: $\alpha$ is the learning rate; $\mu$ is the momentum; and t is the current weight state before updating. The convergence speed of SGD is approximately O(1/t) when the learning rate $\alpha$ are reduced both fast and slow enough. In other implementations, the convolutional neural network uses different loss functions such as Euclidean loss and softmax loss. In a further implementation, an Adam stochastic optimizer is used by the convolutional neural network.

Convolution Layers

The convolution layers of the convolutional neural network serve as feature extractors. Convolution layers act as adaptive feature extractors capable of learning and decomposing the input data into hierarchical features. In one implementation, the convolution layers take two images as input and produce a third image as output. In such an implementation, convolution operates on two images in two-dimension (2D), with one image being the input image and the other image, called the "kernel", applied as a filter on the input image, producing an output image. Thus, for an input vector $f$ of length n and a kernel g of length m, the convolution $f*g$ off and g is defined as:

$$(f*g)(i) = \sum_{j=1}^{m} g(j) \cdot f(i - j + m/2)$$

The convolution operation includes sliding the kernel over the input image. For each position of the kernel, the overlapping values of the kernel and the input image are multiplied and the results are added. The sum of products is the value of the output image at the point in the input image where the kernel is centered. The resulting different outputs from many kernels are called feature maps.

Once the convolutional layers are trained, they are applied to perform recognition tasks on new inference data. Since the convolutional layers learn from the training data, they avoid explicit feature extraction and implicitly learn from the training data. Convolution layers use convolution filter kernel weights, which are determined and updated as part of the training process. The convolution layers extract different features of the input, which are combined at higher layers. The convolutional neural network uses a various number of convolution layers, each with different convolving parameters such as kernel size, strides, padding, number of feature maps and weights.

Learning Models

Implementation specifics will differ widely by application, however anomaly recognition and remediation generally include embodiments in which interface server(s) 102 implement via learning model(s) 134 a statistical learning based process (e.g., an "AI agent") that performs tracking a global state of events in an accessed block chain, identifying anomalies, and deciding to trigger gathering additional information and/or filing a report to another entity. Data points in the events of the accessed block chain are represented by a vector (more generally a tensor) for each data point. Data points in the events can include structured or unstructured data; each can be manipulated using different methods. Programming a mapping to map "structured data" to a vector representation will capture the relevant data of an object, e.g., what's gleaned from scanning a bar code can be mapped to fields in the vector. A pre-trained model can be applied to map unstructured data to a vector (or tensor) representation.

Implementations at the start of their deployment, experience a dearth of labeled data from which to make decisions. Over time, however, as the implementation processes data and takes actions, e.g., detecting events, classifying events as anomalies, and triggering reporting of the anomalies, the results of these actions will produce labelled data. The dynamics of this process mean that implementations starting with an unsupervised learning processes and transition to a semi-supervised learning processes over time with usage. Unsupervised learning processes take similar pieces of data and map them to mathematical objects that are just as similar. Semi-supervised learning processes are applied to instances where some labels are applied to the data, but there are far more unlabeled data than labelled ones.

FIG. 12A is a flowchart illustrating a method for establishing a blockchain network implementing event detection, tracking and management for rule-based compliance, according to various embodiments. Accordingly, in the flowchart 1200A, at block 1201, a blockchain ledger 106 of FIG. 1B, FIG. 1C is provided to a plurality of blockchain nodes (e.g., 102, 136 of FIG. 1B, FIG. 1C).

In block 1202, public and private key pairs are provided to at least one of the blockchain nodes 102 of FIG. 1B, FIG. 1C for authentication of blockchain communications. In various embodiments, private keys are for storage in, or in a manner accessible to, a communication device associated with an entity 102 of FIG. 1B, FIG. 1C.

In block 1203, the blockchain network in conjunction with a set of distributed machine implemented applications (DApps) (e.g., 112 of FIG. 1B, 114 of FIG. 1B, 115 of FIG. 1B) communicating with the blockchain nodes, implements event detection, tracking and management.

In block 1204, the event hub 115 of FIG. 1B detects at least one of a set of block-level events recorded in the blockchain ledger provided to the blockchain nodes. A block in the blockchain ledger corresponds to one of the set of block-level events includes at least an event type data and a set of event data related to the event type data. The at least one of a set of block-level events is received from a blockchain server (e.g., 102, 136 of FIG. 1B, FIG. 1C) of the blockchain network 106 of FIG. 1B, FIG. 1C.

In block 1205, at least one of the set of distributed machine implemented applications (DApps) (e.g., 112 of FIG. 1B, 114 of FIG. 1B, 115 of FIG. 1B) communicating with the blockchain nodes classifies the at least one of a set of block-level events by applying at least the event type data as an input to determine an output of a situation state.

In block 206, triggering an application resident on a server external to the blockchain network to perform one or more actions in dependence upon the situation state as output by the classifier (e.g., 112 of FIG. 1B, 114 of FIG. 1B, 115 of FIG. 1B).

FIG. 12B is a flowchart illustrating a method for establishing a trained machine learning classifier using a blockchain network, according to various embodiments. Accordingly, in the flowchart 1200B, at block 1211, a blockchain ledger storing at least pointers to a plurality of documents 106 of FIG. 1B, FIG. 1C is provided to a plurality of blockchain nodes (e.g., 102, 136 of FIG. 1B, FIG. 1C).

In block 1212, public and private key pairs are provided to at least one of the blockchain nodes 102 of FIG. 1B, FIG. 1C for authentication of blockchain communications. In various embodiments, private keys are for storage in, or in a manner accessible to, a communication device associated with an entity 102 of FIG. 1B, FIG. 1C.

In block 1213, the blockchain network in conjunction with a set of distributed machine implemented applications (DApps) (e.g., 112 of FIG. 1B, 114 of FIG. 1B, 115 of FIG. 1B) communicating with the blockchain nodes, implements establishing a trained machine learning classifier.

In block 1214, the event hub 115 of FIG. 1B detects data from investigative situations including sensed or measured conditions in a physical object or a physical process, and conclusions, outcomes or actions in documents stored by at least one of a set of block-level events recorded in the blockchain ledger provided to the blockchain nodes. The data can include captured evidence of the sensed or measured conditions. The at least one of a set of block-level events is received from a blockchain server (e.g., 102, 136 of FIG. 1B, FIG. 1C) of the blockchain network 106 of FIG. 1B, FIG. 1C.

In block 1215, at least one of the set of distributed machine implemented applications (DApps) (e.g., 112 of FIG. 1, 114 of FIG. 1, 115 of FIG. 1B) communicating with the blockchain nodes labels the data from investigative situations by applying labels selected from a ground truth dataset.

In block 1216, a classifier including a neural network is trained with at least some datapoints of the data from investigative situations and corresponding labels (e.g., 112 of FIG. 1B, 114 of FIG. 1B, 115 of FIG. 1B).

FIG. 12C is a flowchart illustrating a method for establishing a trained machine learning classifier using unsupervised machine learning in a blockchain network. The blockchain network can implement event detection, tracking and management for situation analysis. According to various embodiments, data from clinical trials can be developed into classifiers suited for semi-supervised and supervised machine learning applications by application of unsupervised machine learning techniques.

Accordingly, in the flowchart 1200C, at block 1221, a blockchain ledger 106 of FIG. 1B, FIG. 1C is provided to a plurality of blockchain nodes (e.g., 102, 136 of FIG. 1B, FIG. 1C). The blockchain ledger is preferably storing at least addressing information or pointers to a plurality of documents. Documents can include documents such as clinical trial documents, reports made by governmental agencies, papers published by universities, and so forth.

In block 1222, an unsupervised machine statistical learning model suite (e.g., 134 of FIG. 1B, FIG. 1C) is applied to the documents stored in the blockchain ledger to develop patterns of data recognized from in the documents. Data points in the documents can include structured or unstructured data; each can be manipulated using different methods.

In block 1223a, fields of structured data type data points are mapped into fields of a first tensor representation. Programming a mapping to map "structured data" to a vector representation will capture the relevant data of an object, e.g., what's gleaned from scanning a bar code can be mapped to fields in the vector.

In block 1223b, encoding unstructured data type data points into fields of a second tensor representation. A pre-trained model can be applied to map unstructured data to a vector (or tensor) representation. For example, for textual data, an 'encoder' model takes as input text and maps it to a relatively small vector. A 'decoder' model takes as input that vector and maps it back to text. By training both networks (e.g., encoder, decoder) to minimize the difference between the reconstructed text and the input text, results in an encoder that learns how to represent such text as a tiny vector. This resulting tiny vector can be appended to any other vector. This technique also is effective for images and other unstructured data. The general concept of taking data, mapping it to a small vector(s), and back to itself in order to learn how to represent it as vectors is called autoencoding.

In block 1224, patterns indicating clusters of data are identified in the data points associated with the first tensor representation and the second tensor representation, and a label is applied to each cluster. Numerous possible factors and patterns identified using a statistical model, such as a neural network, kernel method, or a Principal Component Analysis (PCA) to map block level data into a latent vector space. Patterns identified can be investigated by reading/writing from other nodes in the blockchain ledger of blockchain network (106 of FIG. 1B, FIG. 1C) to find like data and reveal previous labelling, and/or treatments of such like data. Meaning can be assigned to the patterns identified, based on the results of such investigations. Such conclusions can be written to a datastore that interface server(s) 102 has access.

In block 1225a, at least one selected from k-means clustering, and a gaussian mixture model, is used to identify at least one semantically meaningful pattern indicating an event in the data as represented by the first tensor and the second tensor.

In block 1225b, natural language data is regularized using labels assigned to clusters of semantically similar data.

In block 1225c, an autoencoder network is used to identify data points of a certain Mahalanobis distance from data clusters labelled as desirable. Autoencoders can be implemented by neural networks that take as input the data, map it to small vectors and back to itself in order to learn how to represent it as vectors. In one implementation and by way of example, in an autoencoder is trained to represent a clinical study summary as a small vector, the text encoder (e.g. implemented using an RNN or Transformer) creates a 50-dimensional vector representing the text of the study, and appends to it a one dimensional vector that represents the outcome score. The 51-dimensional vector that results, termed a latent vector, captures both components of information of the study, and can serve as input to another model. An autoencoder implementation is described in further detail herein with reference to FIG. 12D.

In block 1226, a classifier is developed by continuously training a classifier including a neural network with at least some of the clusters and the labels. A classifier can now be trained (or retrained) on the labelled patterns identified, by accessing a privileged datastore. Training a classifier is described in further detail hereinbelow with reference to FIG. 13C.

In block 1227, the developed classifiers are applied to data points in additional documents to determine events of interest and triggering an application resident on a server external to the blockchain network to perform one or more actions in dependence upon the output by the classifier. For example, interface server(s) 102 can proactively act on identified events of interest discovered by reading/writing from the blockchain 106.

Cluster Identification.

Figure 13A:
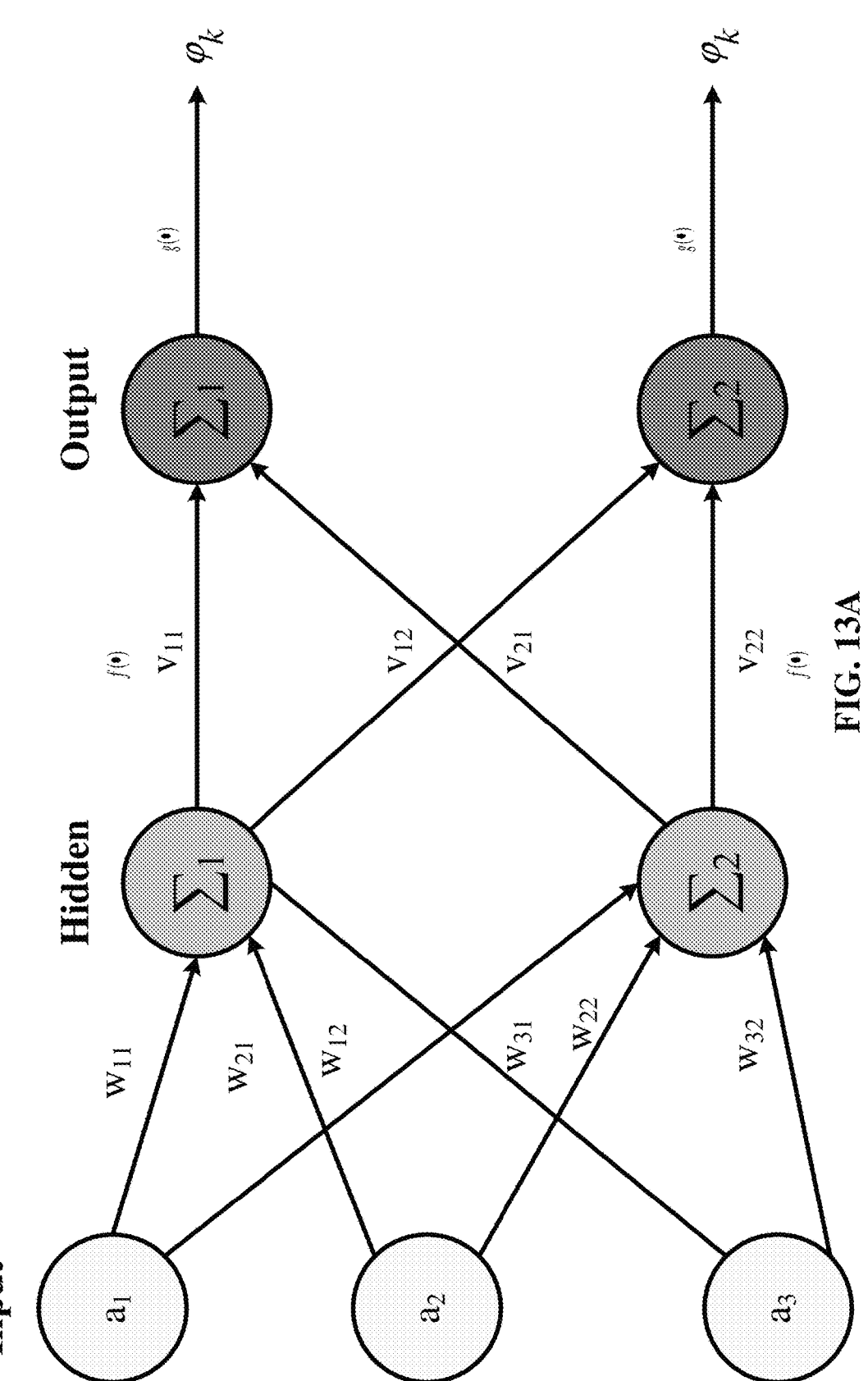
FIG. 13A illustrates a representative neural network suitable for implementing the disclosed technology.

In an implementation, block level events are detected in the blockchain ledger by clustering the blocks according to numerous possible factors and patterns identified using a statistical model, such as a neural network, kernel method, or a Principal Component Analysis (PCA) to map block level data into a latent vector space:

FIG. 13A illustrates a representative neural network suitable for implementing the disclosed technology. Neural network 1300A is a fully connected neural network with multiple layers. A neural network is a system of interconnected artificial neurons (e.g., $a_1$, $a_2$, $a_3$) that exchange messages between each other. Neural network 1300A has three inputs, two neurons in the hidden layer and two neurons in the output layer. The hidden layer has an activation function $f(\cdot)$ and the output layer has an activation function $g(\cdot)$. The connections have numeric weights (e.g., $w_{11}, w_{21}, w_{12}, w_{31}, w_{22}, w_{32}, v_{11}, v_{12}, v_{21}, v_{22}$) that are tuned during the training process, so that a properly trained network responds correctly when fed an image to recognize.

The input layer processes the raw input, the hidden layer processes the output from the input layer based on the weights of the connections between the input layer and the hidden layer. The output layer takes the output from the hidden layer and processes it based on the weights of the connections between the hidden layer and the output layer. The network includes multiple layers of feature-detecting neurons. Each layer has many neurons that respond to different combinations of inputs from the previous layers. These layers are constructed so that the first layer detects a set of primitive patterns in the input image data, the second layer detects patterns of patterns and the third layer detects patterns of those patterns.

Kernel methods include the classifier begins with the i-th training example, $(x_i, y_i)$ learns for it a corresponding weight $w_i$. Prediction for unlabeled inputs, i.e., those not in the training set, is treated by the application of a similarity function k, called a kernel, between the unlabeled input x' and each of the training inputs $x_i$ An example kernel binary classifier computes a weighted sum of similarities:

$$\hat{y} = \text{sgn} \sum_{i=1}^{n} w_i y_i k(X_i X')$$

where: $\hat{y} \in \{-1,+1\}$ is the kernelized binary classifiers predicted label for the unlabeled input x', k: X x X→R is the kernel function that measures similarity between any pair of inputs x, $x' \in X_i$; the sum ranges over the n labeled examples $$\{(x_i, y_i)\}_{i=1}^{n}$$

in the classifier's training set, with $y_i \in \{-1, +1\}$; the $w_i \in R$ are the weights for the training examples, as determined by the learning algorithm; the sign function sgn determines whether the predicted classification $\hat{y}$ comes out positive or negative. Reference may be had by persons skilled in the art to Wikipedia, en.wikipedia.org/wiki/Kernel_method, for further information concerning kernel method.

Principal Component Analysis (PCA) is mathematically defined as an orthogonal linear transformation that transforms the data to a new coordinate system such that the greatest variance by some scalar projection of the data comes to lie on the first coordinate (called the first principal component), the second greatest variance on the second coordinate, and so on. In one implementation, a p-dimensional ellipsoid is fit to the data, where each axis of the ellipsoid represents a principal component. If some axis of the ellipsoid is small, then the variance along that axis is also small, and by omitting that axis and its corresponding principal component from our representation of the dataset, we lose only an equally small amount of information. Reference may be had by persons skilled in the art to Wikipedia, en.wikipedia.org/wiki/Principal_component_analysis for further information concerning principle component analysis.

At this point, an unsupervised learning algorithm such as k-means clustering, or a gaussian mixture model is used to identify in the data semantically meaningful patterns indicating an event. For example, similarities identified in clusters indicate an event, e.g. a headache after taking pills could be clustered to a lot (i.e., bad production event), to a time (swapped pills event), or to a location (damaged while shipping event). Each field in the FDA 3911 report would be tagged in a block level data structure that can be shared on the blockchain. Implementations can enable easier sorting of events and issuing notifications. For example, a rash of seemingly unrelated events in the opiate category might point back to a specific problematic manufacturing lot, while other correspondences between reports could reveal fraudulent activity.

Regularizing Free-Form Typical Input Learning.

People have many different ways of describing the same thing, which can confound traditional reporting systems. The system could regularize input by suggesting typical responses and verifying hypothesized clusters by suggesting responses. One implementation can regularize data by mapping it into a semantically meaningful vector space, learned from a large corpus of data. In the case of "regularizing" natural language input, this may be a space learned from training a sequence to sequence model statistical model/ neural network to encode text to a vector and that vector back to the original text. The resultant vectors encode the 'meaning' of the input text. As such, similar text inputs can be easily grouped together. If those groups are labelled, the labels can be easily suggested. (For instance, a user may write "pills look weird," the system might suggest "damaged pills" or "pills look different than normal" as options. Using natural-language generation, the AI would then ask several follow-up questions to look for a match that builds out a cluster and provides context for its image-recognition efforts.)

Autoencoder Network for Bad Actor Identification

FIG. 12D is a flowchart illustrating a method for establishing a trained machine learning classifier using unsupervised machine learning for classifying nodes in a blockchain network in a healthy blockchain network state(s) or an unhealthy blockchain network state. The blockchain network can implement event detection, tracking and management for situation analysis or other purposes. According to various embodiments, data from compliance reporting, data from clinical trials, and/or data from manufacturing and distribution processes can be developed into classifiers suited for semi-supervised and supervised machine learning applications by application of unsupervised machine learning techniques.

Accordingly, in the flowchart 1200D, at block 1231, a blockchain ledger 106 of FIG. 1B, FIG. 1C is provided to a plurality of blockchain nodes (e.g., 102, 136 of FIG. 1B, FIG. 1C). The blockchain ledger is preferably storing at least addressing information or pointers to a plurality of documents. Documents can include documents such as clinical trial documents, reports made by governmental agencies, papers published by universities, reports created or managed by participants in the course of manufacturing and distribution processes, and so forth.

Figure 13B:
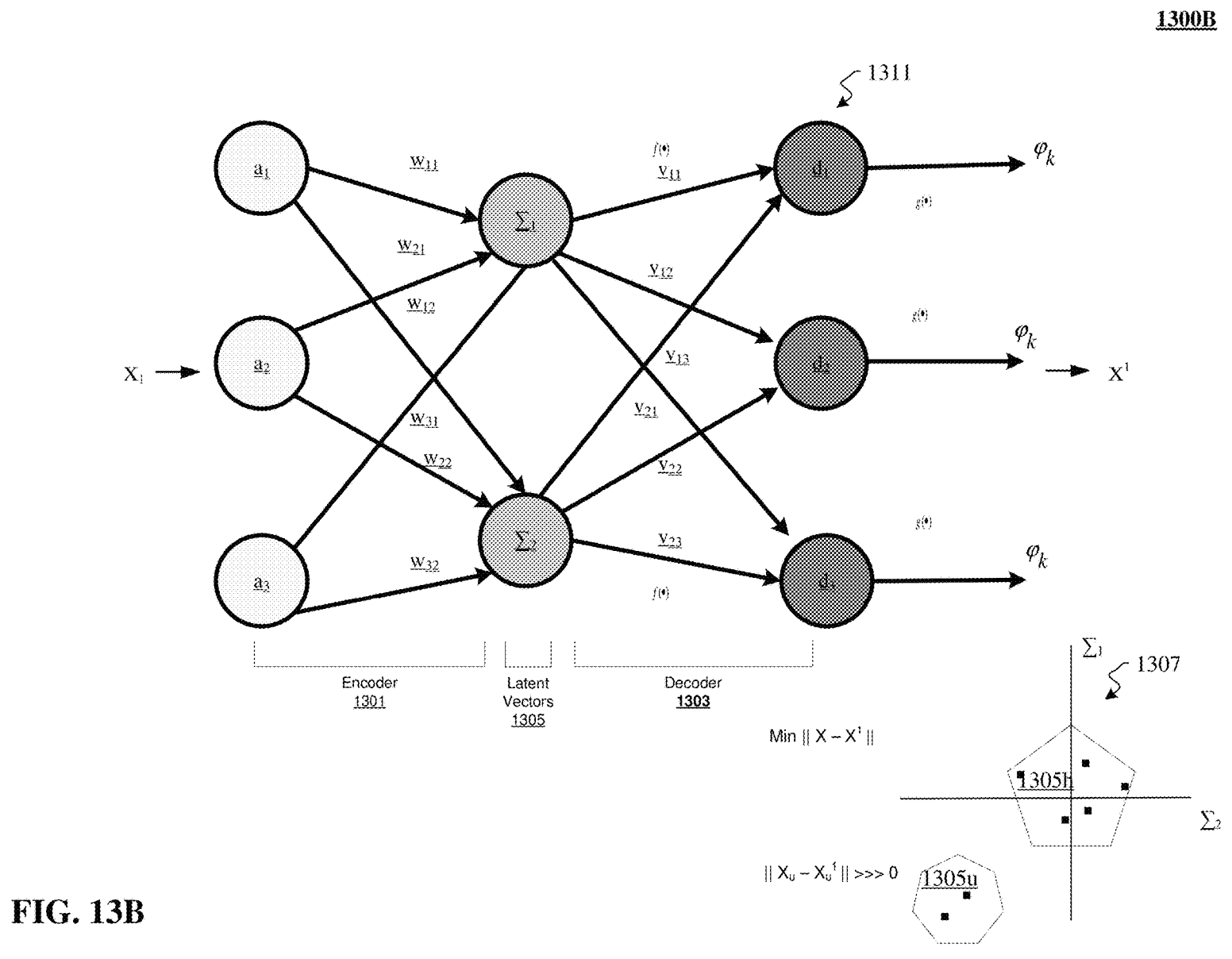

In block 1232, an autoencoder semi-supervised statistical machine learner is applied to the documents stored in the blockchain ledger (e.g., pointed upon or stored in accordance with) to develop patterns of data recognized from in the documents. The autoencoder can be stand alone or a component of an unsupervised machine statistical learning model suite (e.g., 134 of FIG. 1B, FIG. 1C). One implementation of an autoencoder semi-supervised statistical machine learner is representative neural network 1311 illustrated by FIG. 13B, in which a neural network 1311 is used for implementing autoencoding to detect anomalous data, such as a spam, corrupt data, or data indicative of an anomaly in compliance reporting, data from clinical trials, and/or data from manufacturing and distribution processes or other bad data in the block chain.

In block 1233*a*, autoencoder neural network 1311 (e.g., based on an RNN or transformer) is trained on 'healthy' blockchain data $x_h$. Healthy blockchain data $x_h$, while application dependent, can include specific params such as transactions against the blockchain ledger per second, percentage of transactions recorded in the blockchain ledger that include transactions between pharmaceutical suppliers and wholesalers, percentage of transactions recorded in the blockchain ledger that include transactions between wholesaler and pharmacy, percentage of transactions recorded in the blockchain ledger that include transactions between pharmaceutical manufacturer and wholesalers. Number of transactions recorded in the blockchain ledger that include transactions occurring between industry participants and others. While neural network autoencoder 1311 is illustrated generally with 3 input nodes, 2 internal or hidden nodes and 3 output nodes, implementations will include different and varying configurations. For example, one implementation might receive data x comprising 1024-dimensional data, compress the data to latent vectors 1305, which may be as small as single dimensional data, and then re-inflate the data to output data $x^1$ of 1024 dimensions.

In block 1234*a* a 'reconstruction loss'

$$\left\| x_h - x_h^1 \right\|$$

of the autoencoder is measured on the healthy data $x_h$. The classifier, having been trained on 'healthy data'—e.g., data for a blockchain in normal state—only, will not reconstruct input for unhealthy data as well as healthy data at run time. In a block 1235*a*, when the autoencoder is deployed a blockchain in a normal or healthy blockchain state will exhibit a minimal reconstruction loss, i.e., $$\min \left\| x_h - x_h^1 \right\|.$$

If the 'reconstruction loss' is substantially higher on data during deployment, e.g., against a threshold, and/or the blockchain is in an unhealthy blockchain state; in such case, the blockchain system is deemed to be 'unhealthy' or 'under attack'.

In block 1233*b*, alternatively when a set of historical training data is available, the encoder section 1301 of the autoencoder network 1311 is used to encode all data (e.g., healthy $x_h$ and unhealthy $x_u$) to a set of latent vectors 1305. A classifier is trained on the latent vectors, labelled with whether they represent a 'normal' or 'abnormal' blockchain state. In a block 1234*b*, the trained classifier can deployed to classify input data as either normal or abnormal.

In a block 1233*c*, alternatively the encoder 1301 is used to encode all data (e.g., healthy $x_h$ and unhealthy $x_u$) at deploy time to a latent space 1307. In latent space 1307, latent vectors 1305*h* will cluster about one another. In block 1234*c*, data points of a certain Mahalanobis (or other metric) distance from data clusters labelled as desirable are identified. Latent vectors 1305*u* that are, according to some distance metric (e.g. L2 or Mahalanobis distance) far from 'healthy' data points are deemed to be 'unhealthy' or as 'resulting from an attack'.

In block 1236, a classifier is developed by continuously training a classifier including a neural network with at least some of the clusters and the labels. A classifier can now be trained (or retrained) on the labelled patterns identified, by accessing a privileged datastore. Training a classifier is described in further detail hereinbelow with reference to FIG. 13C.

In block 1237, the developed classifiers are applied to data points in additional documents to determine events of interest and triggering an application resident on a server external to the blockchain network to perform one or more actions in dependence upon the output by the classifier. For example, interface server(s) 102 can proactively act on identified events of interest discovered by reading/writing from the blockchain 106.

Accordingly, implementations employing the foregoing disclosed technology can identify spam transactions on the blockchain ledger, employ learned data stored with user identity to verify claimed identity, compute confidence scores to score transactions, and automatically trigger mitigating actions to be taken by downstream applications (e.g. forced slowing of transaction rate or flagging a suspicious user for review). Atypical transactions can be flagged for possible review to catch malicious activity. In other usage scenarios, one implementation of an encoder neural network enabled interface server(s) 102 can identify improper behavior such as forced shortages and front-running.

Convolutional Neural Network (CNN)

One implementation of a neural network enabled interface server triggers prompts asking for the submitting parties to take photos and use image recognition to identify classes of problems and highly probable matches. A convolutional neural network is trained on a curated database of pill photos, labelled with defects. If defects are rare, examples of defective pills may be oversampled to provide the network with adequate inputs during training. The neural network may be given unsupervised pre-training on a dataset of unlabeled photos in order to learn latent representations of different kinds of pills and their defects, hence reducing the amount of labelled data needed to learn. One range of solutions involves comparing an image of a suspicious pill to visual databases of pills and identifying potential substitutions that may have occurred in the supply chain. Another range would include assessments of the state of the medication (e.g. color and cloudiness of a liquid medication). As a deep learning methodology designed for two-dimensional image data and requires little initial pre-processing, CNN is well-suited for this purpose.

Classifier Inputs and Outputs

An exemplary deep neural network implementation selects an appropriate classification of the illegitimate product or product with a high risk of illegitimacy using a set of inputs to the neural network. Inputs whether structured or unstructured data type data points, can be encoded into fields of a vector (or tensor) representation. Implementations will employ various levels of abstraction in configuring, classification and anomaly detection tasks, e.g., in a pharmaceutical application, data can be selected to describe pharmaceutical manufacturing lots, shipment lots, nodes in a distribution network, entities, geographies and so forth. In one example, a neural network ensemble can implement a classifiers that are trained to classify situation states according to input data useful in regulatory compliance reporting, such as without limitation: A type of report (e.g., initial notification, follow-up notification, or request for termination), an incident number (provided by FDA) for follow-up and request for termination, a date of initial notification to FDA (MM/DD/YYYY), a date company determined product was illegitimate (MM/DD/YYYY), a name of product as it appears on the label, primary ingredients, drug use (human, other), a drug description (e.g., finished prescription drug, vaccine, plasma derivative (e.g., coagulation factors, immunoglobulins, albumin), allergenic (e.g., standardized and non-standardized), or multiple), a strength of drug (e.g., 500 mg. 1 g/10 mL), a dosage form (e.g., tablet, capsule, aerosol, oral liquid, sublingual, injectable, topical, supposi- tory, other, or multiple), a quantity of drug (Number and Unit), an NDC (Nat'l Drug Code) number, a serial number, lot number(s), expiration date(s), (for notification) a descrip- tion of event/issue, (for request for termination of notifica- tion) description of why notification is no longer necessary, other reports submitted to the FDA (e.g., FAR—Field Alert Report, BPDR—Biological Product Deviation Report, Med- watch 3500, Medwatch 3500A, none, other), company name and address, company category, manufacturer, wholesale distributer, dispenser (Pharmacy), repackager, Unique Facil- ity Number (D-U-N-S), and contact information.

The classifier(s) once trained on a training dataset can determine a Classification of Notification (Counterfeit, Diverted, Stolen, Intentional adulteration, Unfit for distri- bution, Fraudulent transaction) for a particular situation state. The exemplary deep neural network implementation selects an appropriate classification of the illegitimate prod- uct or product with a high risk of illegitimacy from a set of outputs.

process the input anomaly information through at least one of the deep neural network 1334, the first anomaly subnet- work, and the second solution accessibility subnetwork to produce outputs that are transmitted to the client devices 122.

Training servers 1302 conduct training using models and comprise a situation dataset generator 1322 includes a deep convolutional neural network based variant anomaly classi- fier, running on numerous processors coupled to memory that prepares training sets comprising data chosen from large scale training dataset 1312 to reflect one or more scenarios being trained, a variant anomaly classifier 1332 includes a deep convolutional neural network based variant anomaly classifier, running on numerous processors coupled to memory that is trained to recognize anomalous situations from sensed data using the scenarios prepared, an optional secondary classifier 1342 includes a deep convolutional neural network based secondary anomaly classifier, running on numerous processors coupled to memory that is trained to recognize special situation anomalies (e.g., radioactive spill, biohazard, etc.), a solution accessibility classifier 1352 includes a deep convolutional neural network based second- ary anomaly classifier, running on numerous processors coupled to memory that is trained to recognize anomalies

| Output | Determined Conditions |
|---|---|
| Counterfeit | A product is determined to be counterfeit, or has a high risk of being counterfeit. |
| Diverted | A product is determined to be a diverted product, or has a high risk of being a diverted product. |
| Stolen | A product is determined to be a stolen product, or has a high risk of being a stolen product. |
| Intentional adulteration | A product is determined to be intentionally adulterated such that use of the product would result in serious adverse health consequences or death to humans, or has a high risk of it. |
| Unfit for distribution | A product appears otherwise unfit for distribution such that use of the product would be reasonably likely to result in serious adverse health consequences or death to humans, or has a high risk of it. |
| Fraudulent transaction | A product in your possession or control is determined to be the subject of a fraudulent transaction, or has a high risk of it. |

In one exemplary implementation, some neural networks implementing learning model(s) 134 are implemented as an ensemble of subnetworks trained using datasets widely chosen from approved transactions and flagged transactions, with outputs including classifications of anomalies based upon the input sensed data, and/or remedial actions to be triggered by invoking downstream applications such as preparing and submitting reports to blockchain implemented regulatory compliance information, as well as the capability to both cluster information and to escalate problems. Having described neural network implementations, the discussion now turns to deep learning approaches.

Figure 13C:
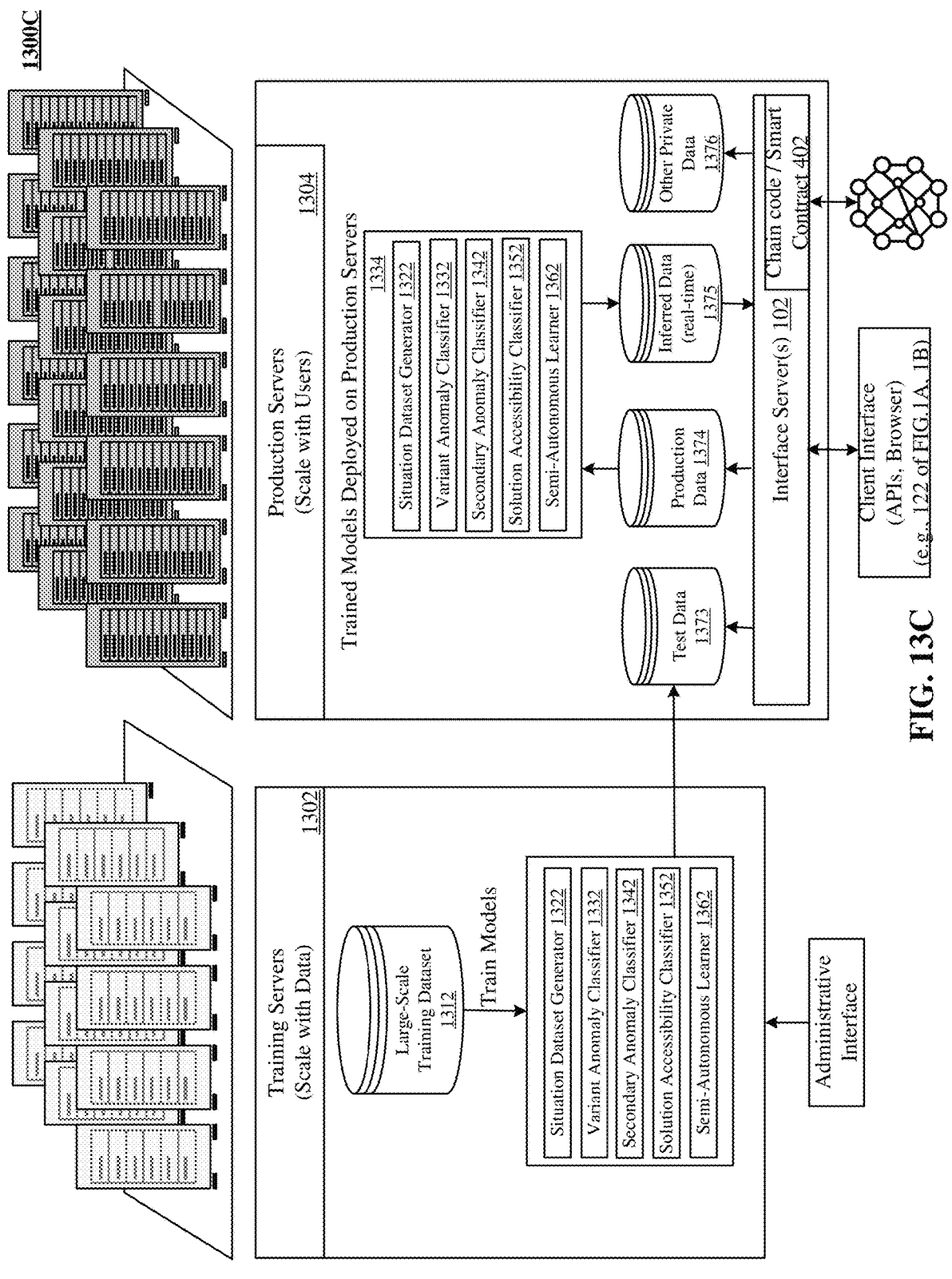
FIG. 13C illustrates a deep learning system in a supervised or semi-supervised implementation.

FIG. 13C illustrates a deep learning system in a super- vised or semi-supervised implementation. As shown, deep learning system 1300C includes training servers 1302 and production servers 1304. Large scale training dataset 1312 is accessible to training servers 1302 for training the deep convolutional neural network 1334. In an implementation, deep neural network 1334 includes a first anomaly subnet- work, and a second solution accessibility subnetwork that are trained on one or more training servers 1302. The trained deep neural network ensemble including the first trained anomaly subnetwork, and the trained second solution acces- sibility subnetwork are deployed on one or more production servers 1304 that receive input anomaly information from requesting client devices 122. The production servers 1304 and output identifiers identifying remedial applications that are invoked to trigger remedial actions. A semi-autonomous learner 1362 includes a deep convolutional neural network based variant anomaly classifier, running on numerous pro- cessors coupled to memory that progressively augments a set size of the anomaly training set based on the trained ensemble's evaluation of a synthetic set or in implementa- tions, input of live data from a real world scenario.

In one implementation, the neural networks such as situation dataset generator, variant anomaly classifier, sec- ondary anomaly classifier, solution accessibility classifier, and semi-autonomous learner are communicably linked to the storage subsystem comprised of test data database 1373, production data database 1374, inferred data database 1375 and other private data database 1376 and user interface input devices.

In one implementation, data used in one or more of large scale training dataset 1312, test data database 1373, produc- tion data database 1374, inferred data database 1375 and other private data database 1376 is selectively obtained from multiple sources of data: (i) various drug databases (e.g., the FDA Product-Specific Guidance database, which enables searching and clustering by active ingredient(s)) and com- munications including machine reading of emails on recalls minimizes the need to change notification protocols that can be related to machine-readable data and image recognition (e.g. images of pills) and (ii) user responses to deep learning driven follow-up questions selected by the solution accessibility classifier 1352 and semi-autonomous learner 1362 (allowing for live training and refinement).

Figure 14A:
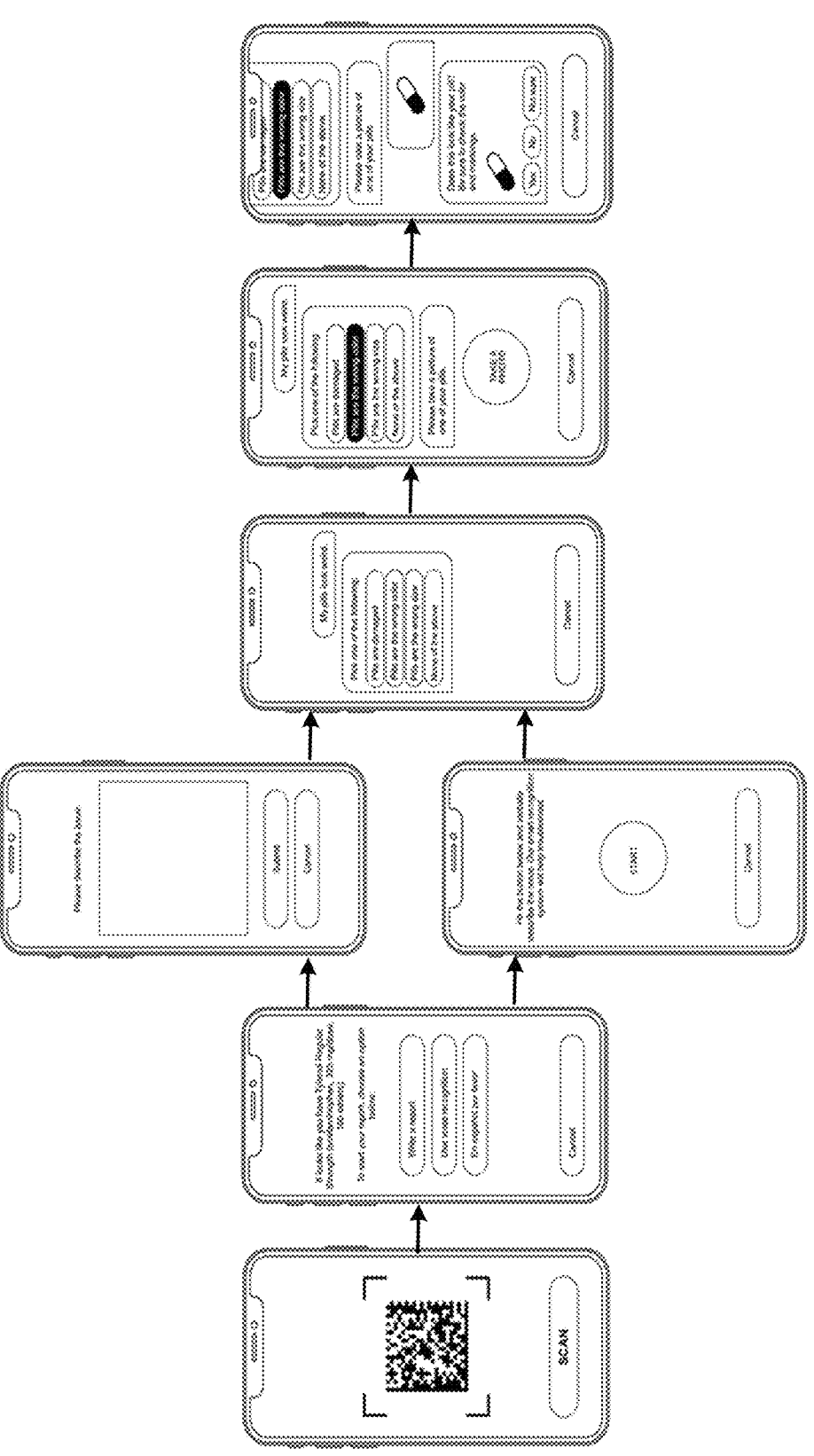
FIGS. 14A, 14B, 14C, 14D, 14E, 14F, 14G, 14H and 14I depict screenshots displayed by a typical client device in conjunction with an example use case 1400.
Figure 14B:
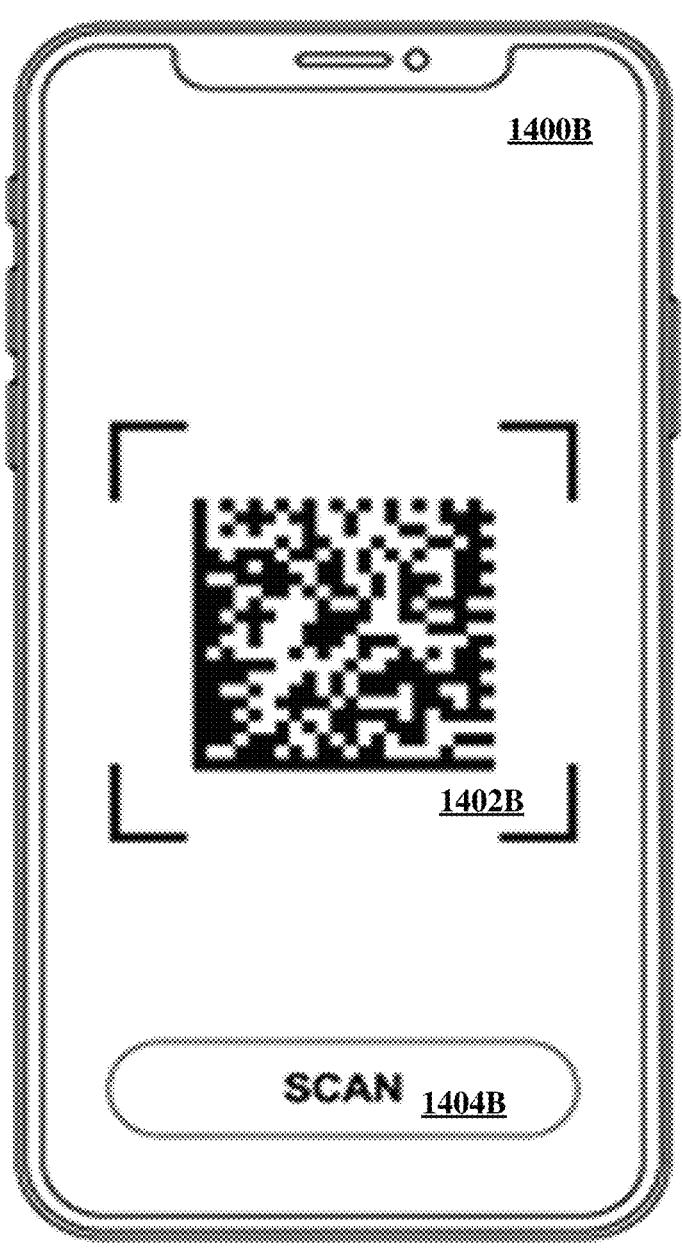

FIGS. 14A-14H depict an example use case 1400. In FIG. 14A, an example 1400A depicts a series of prompts displayed to a user in a representative usage scenario. In FIG. 14B, an example screen 1400B is shown. Screen 1400B displays a QR code 1402B that the client device 122 has displayed along with a scan prompt 1404B, enabling the user to capture the QR code by depressing the prompt 1404B. Client device 122 captures the QR Code and sends the QR code to the interface server(s) 102 via network(s) 101. The interface server(s) 102 will retrieve information from private storage server(s) 156 and sends this information to the client device 122 via the network(s) 101.

Figure 14C:
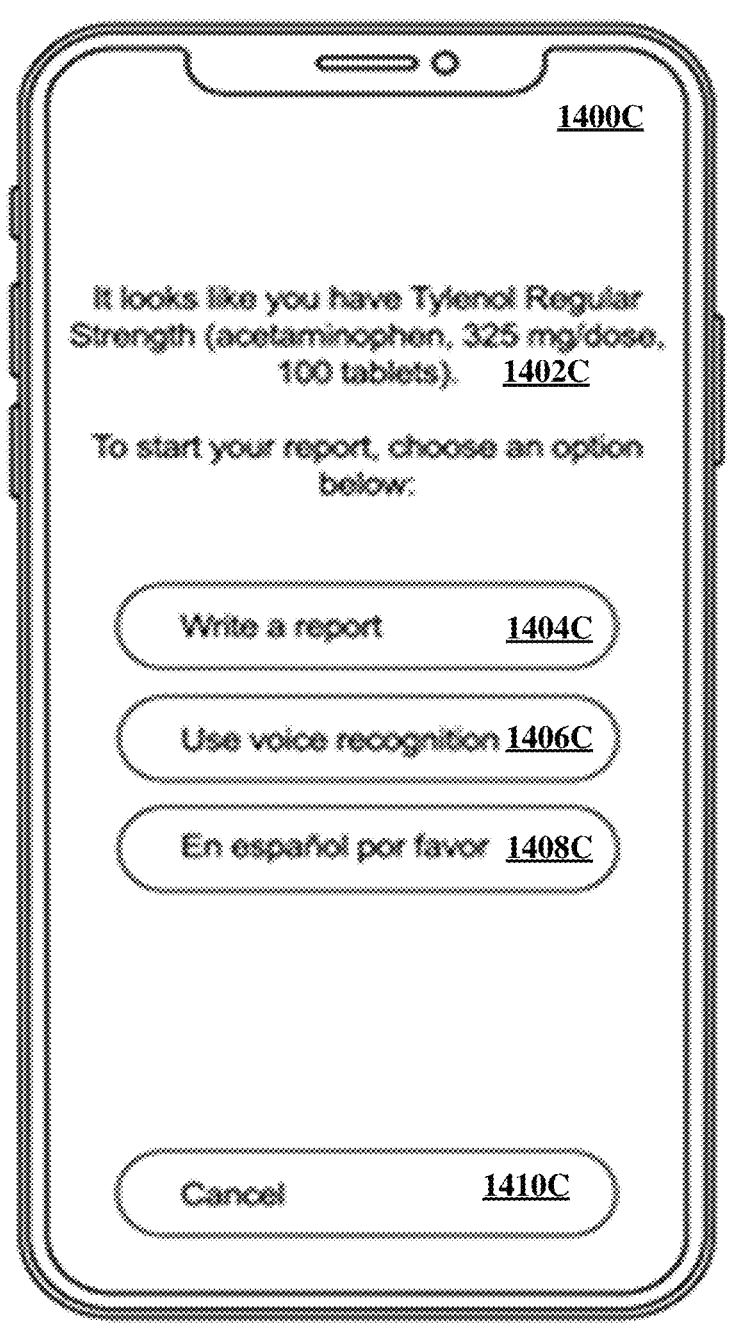

In FIG. 14C, screen 1400C displays the information 1402C sent to client devices 122. Screen 1400C also displays a plurality of prompts to solicit from the user an input triggering a course of action, including a write report prompt 1404C, a use voice recognition prompt 1406C, a prompt 1408C to change user languages and a cancel prompt 1410C. Not all prompts will be displayed in every implementation. Further, some implementations will include other additional prompts facilitating different actions.

Figure 14D:
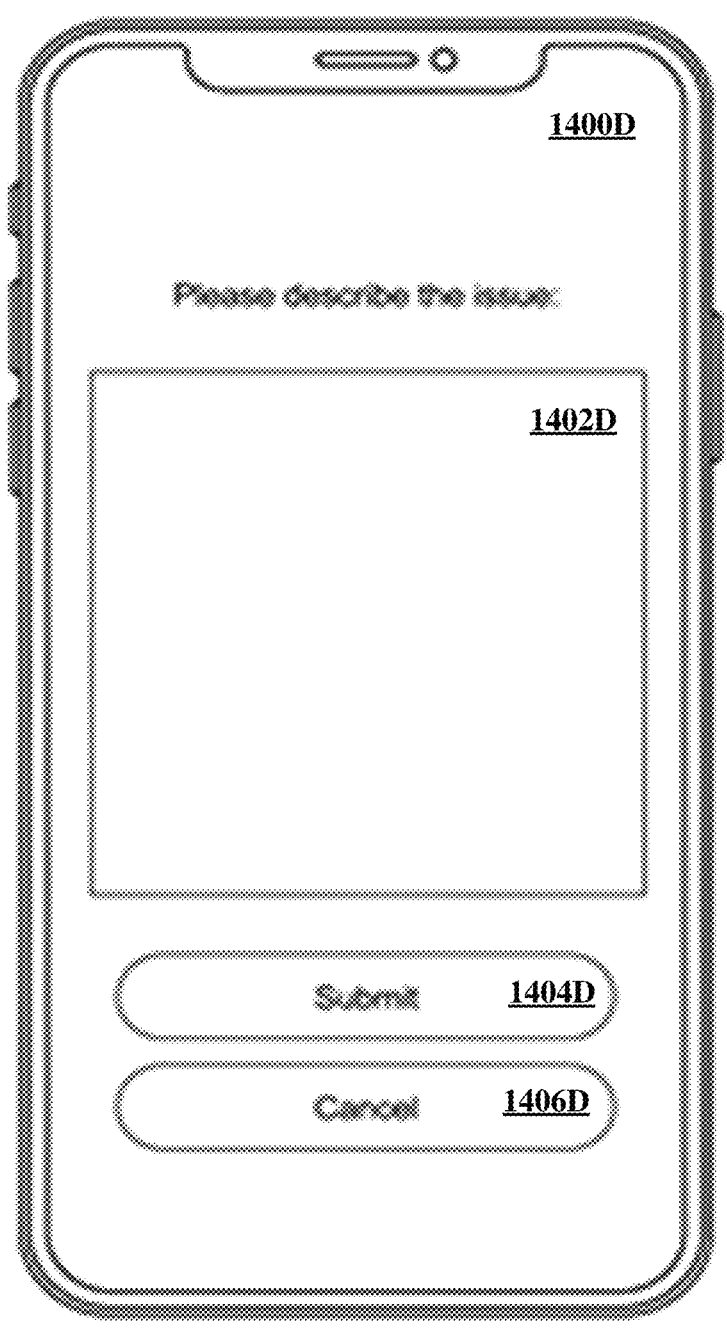
Figure 14E:
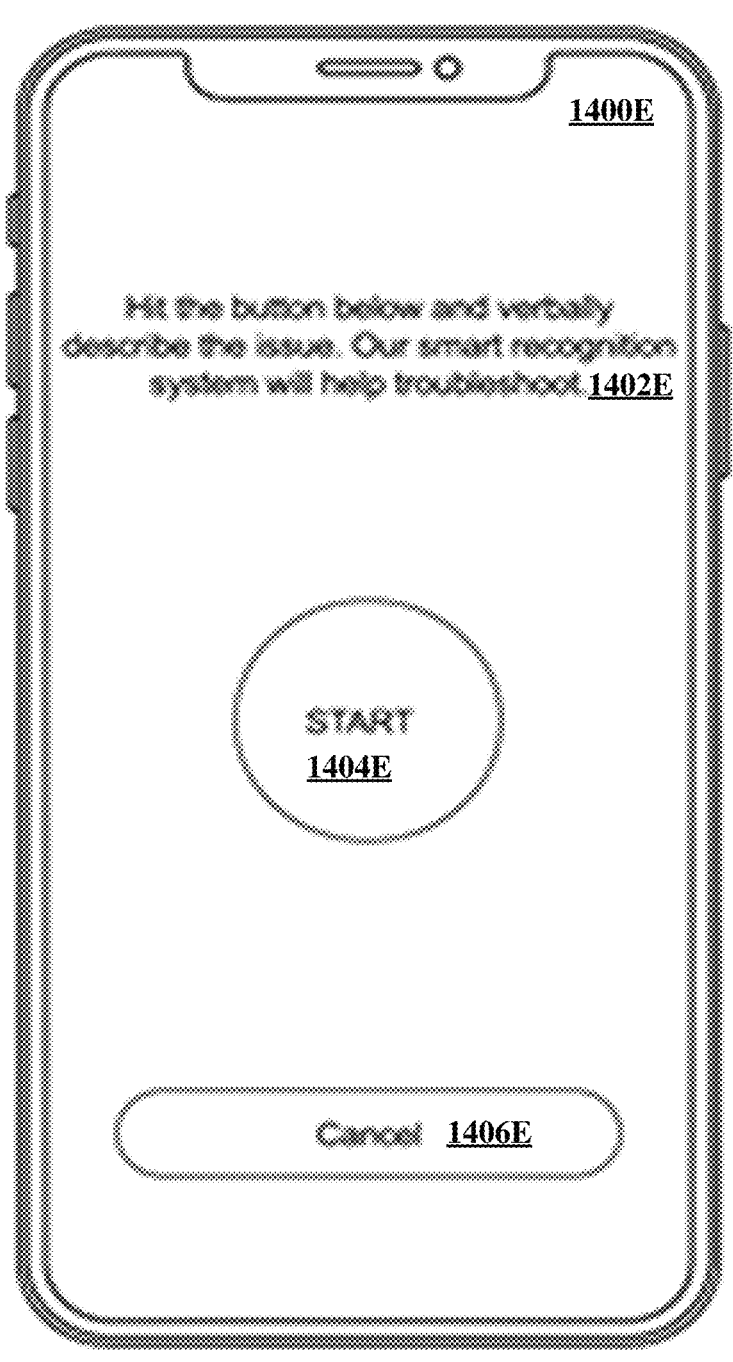

Now with reference to FIG. 14D, screen 1400D is displayed by client device 122. Interface server(s) 102 has triggered client device 122 to display an input area 1402D prompting the user to enter a description of an issue or problem. Screen 1400D further includes a submit prompt 1404D and a cancel prompt 1406D. When a user enters their problem description into the input area 1402D and selects the submit prompt 1404D, client device 122 sends the information to the interface server(s) 102. The interface server(s) 102 analyzes the input text into vector representations and inputs these into one or more of the learning models (s) 134. Learning model(s) 134, such as a deep neural network(s) 1334 provide an output result based upon statistically learned results. The interface server(s) 102 using the result triggers an application to implement a course of action selected by the learning model(s) 134 as having a greater than threshold probability to remediate the problem encountered. The course of action can include one or more of prompting the client device 122 for additional details, or inputs such as capturing a photograph, voice input, etc., directions to the user such as how to dispose of or return a bad lot, and/or formulate a report to a regulatory agency. One example of one type of follow up prompting triggered by interface server(s) 102 is illustrated by FIG. 14E, depicting a screen 1400E including a voice input prompt 1402E that prompts the user to press a prompt 1404E and describe the issue. A cancel prompt 1406E is also provided.

Figure 14F:
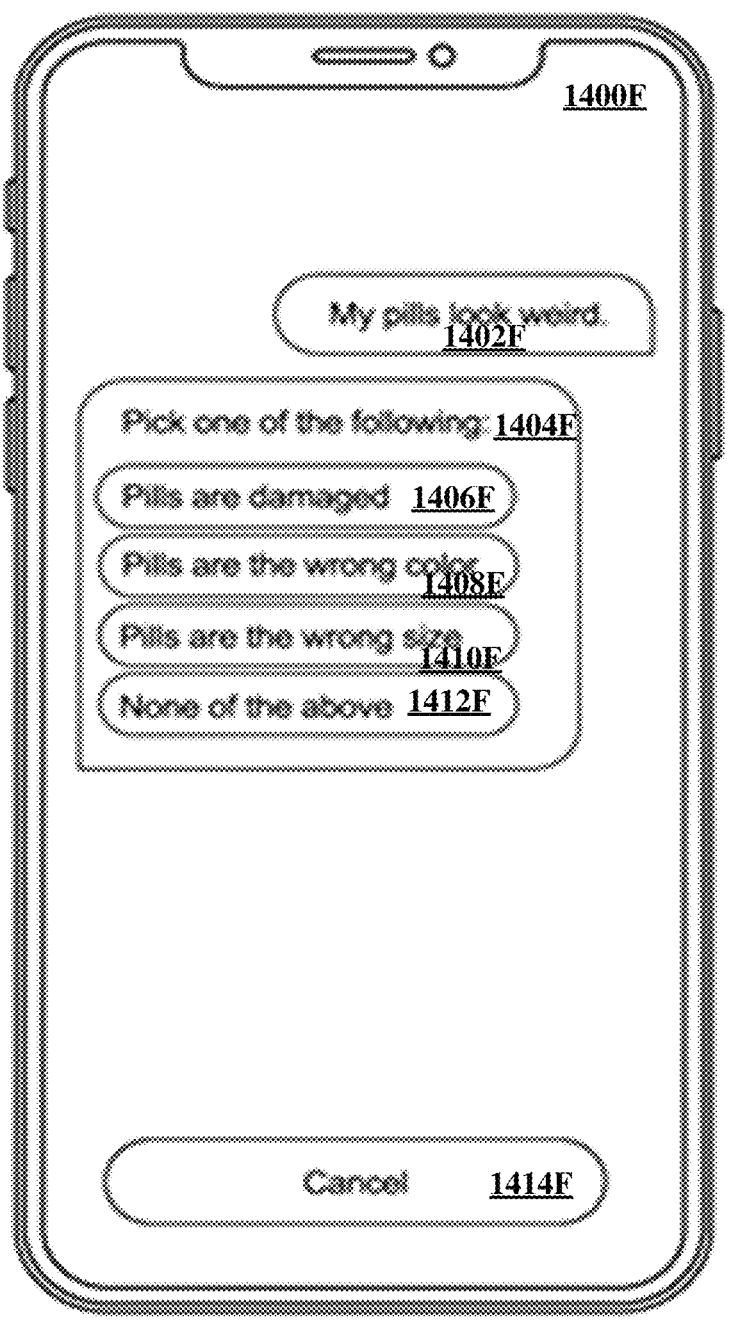

FIG. 14F depicts screen 1400F illustrating an example of another type of follow-up prompting triggered based upon output of learning model(s) 134. In the scenario illustrated by FIG. 14F, the user has entered a nebulous input "my pills look weird" in input box 1402F. Client device 122 passed this nebulous input to the interface server(s) 102, which analyzed the nebulous input and submitted it as input to one or more of the learning model(s) 134. Learning model(s) 134, such as a deep neural network(s) 1334 provide an output result based upon statistically learned results provided as output a set 1404F of follow-up prompts. Follow up prompt 1404F prompts the user to "pick one of the following" from a set of potential inputs. The set of potential inputs selected by the learning model(s) 134 as having a greater than threshold probability to remediate the problem encountered include "pills are damaged" 1406F, "pills are the wrong color" 1408F, "pills are the wrong size" 1410F and "none of the above" 1412F. Also displayed is an option for the user to cancel 1414F.

Figure 14G:
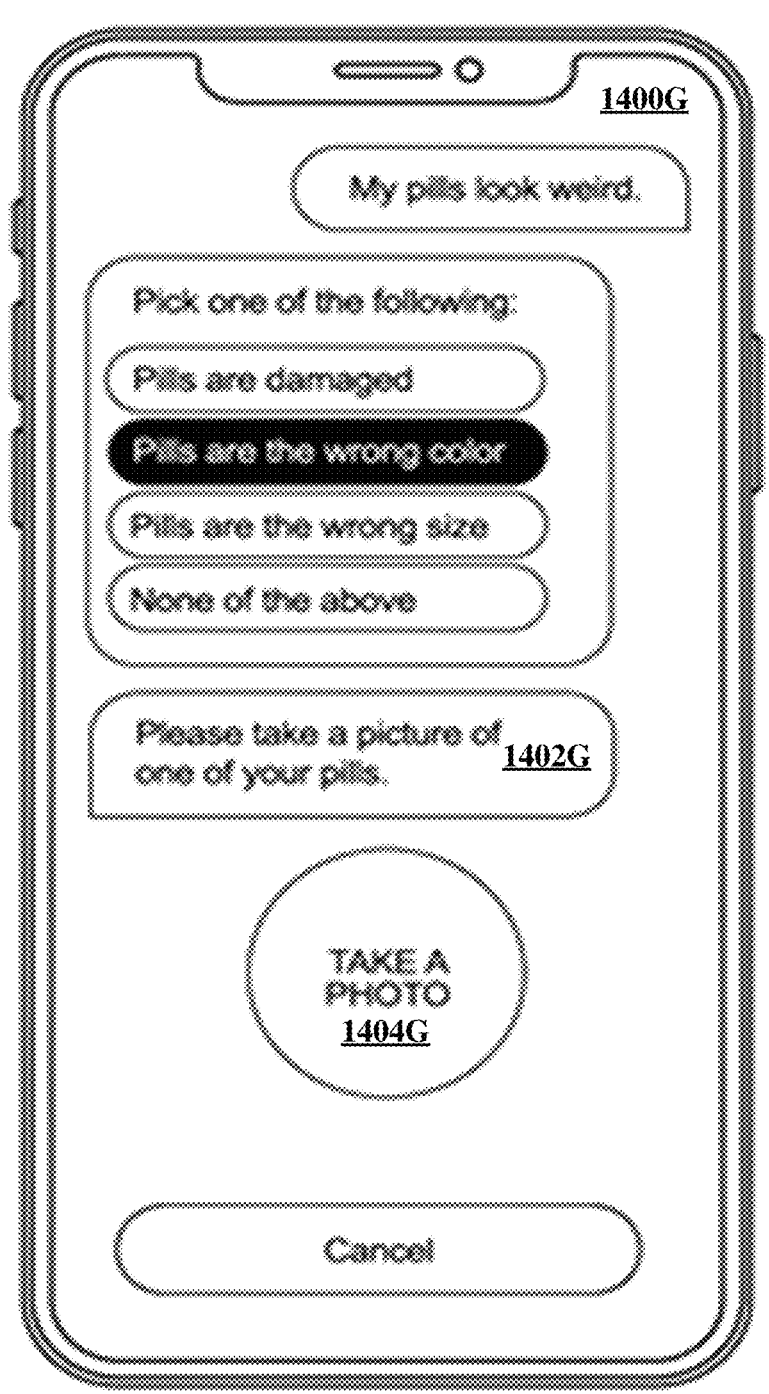
Figure 14H:
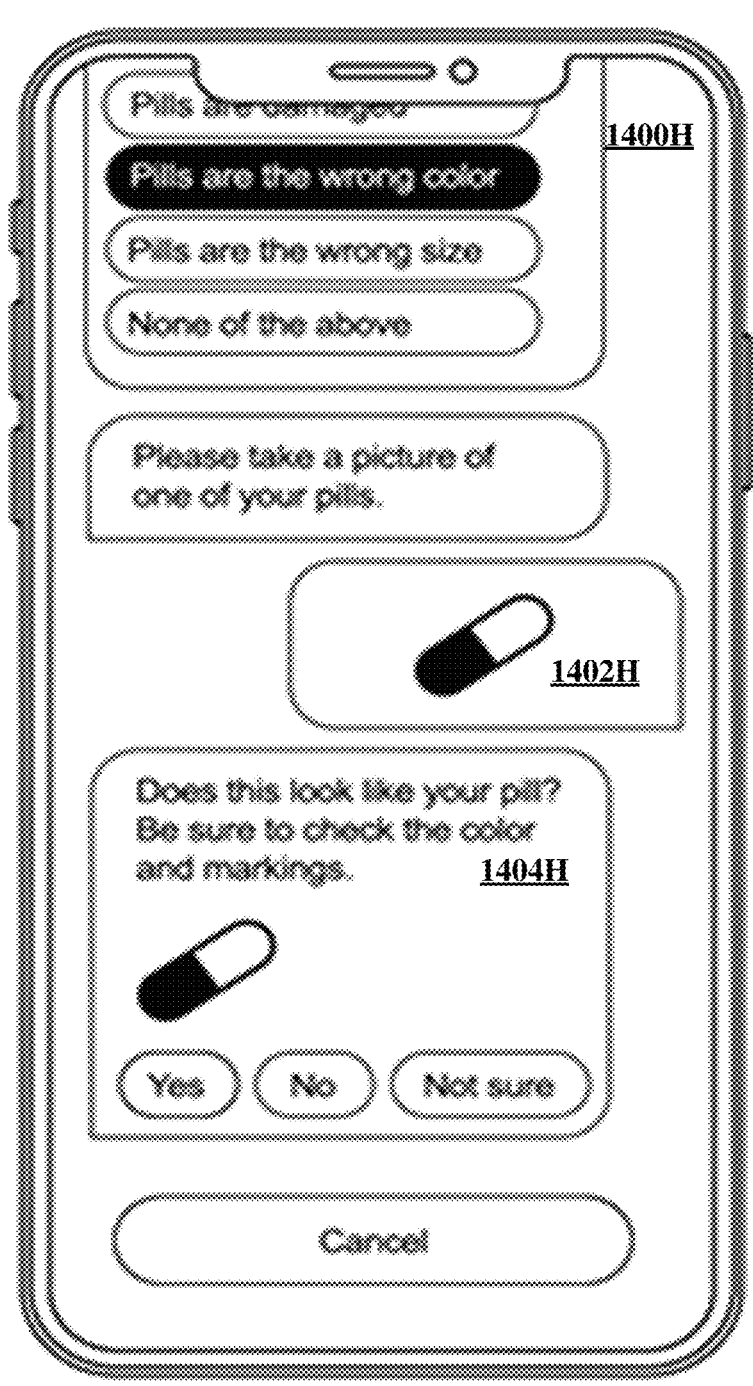

Now with reference to FIG. 14G, continuing with the scenario described with reference to FIG. 14F, the user has selected option "pills are the wrong color" 1408F. The interface server(s) 102 respond with a further follow-up prompt 1402G that urges the user to use the camera of client device 122 to take a picture of one of your pills and provides a camera trigger prompt 1404G. Alternatively, or in addition, follow up screen 1400H of FIG. 14H can be triggered. Screen 1400H includes a picture 1402H of the product corresponding to the QR code input in screen 1400B, which the interface server(s) 102 have retrieved from private storage server(s) 156. Screen 1400H further includes a follow up prompt 1404H that asks the user specifically about the picture 1402H and the product that the user of client device 122 is working with. The user's response will be sent to the interface server(s) 102 and again submitted to the learning model(s) 134 to trigger a remedial action if appropriate.

Figure 14I:
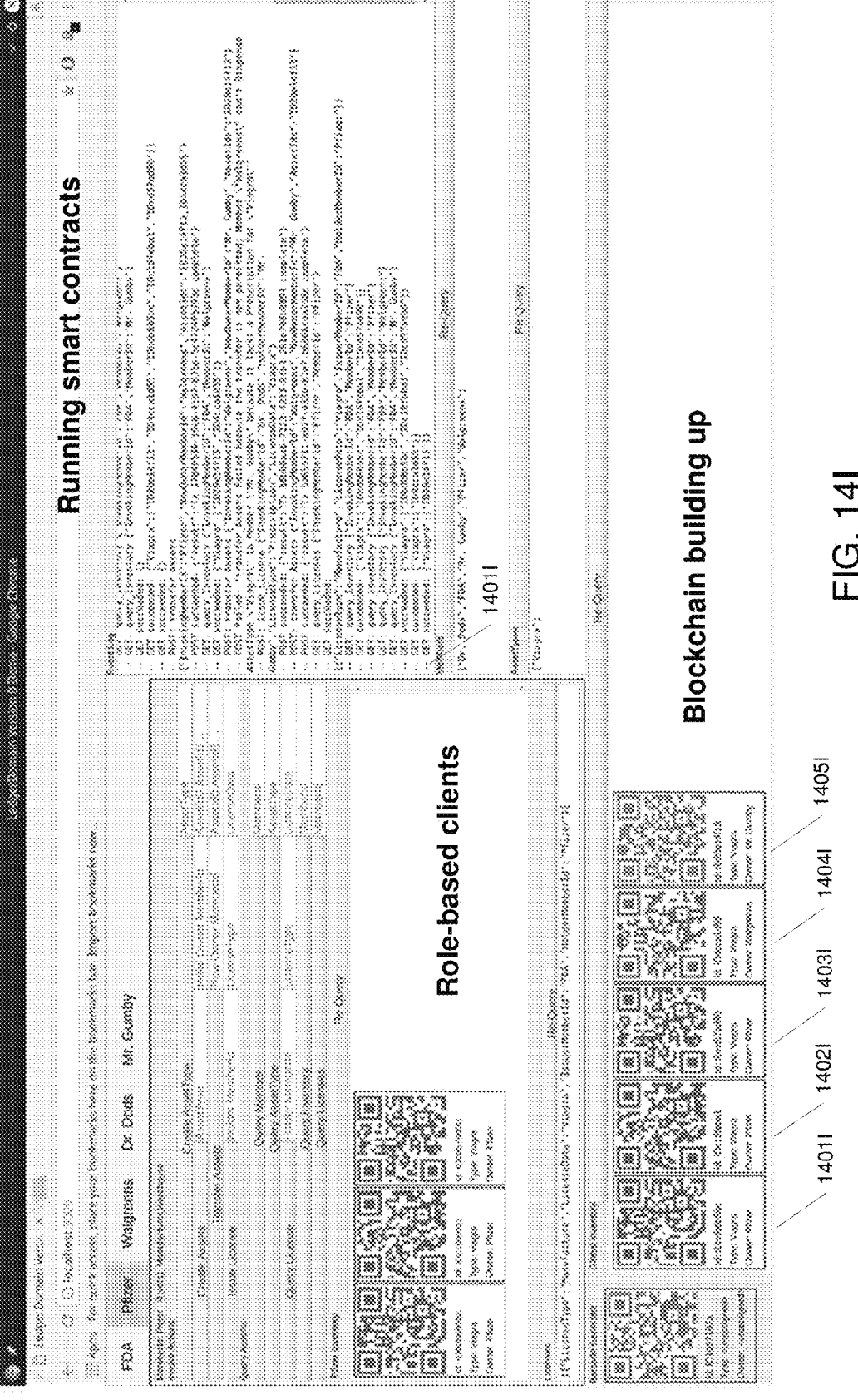

FIG. 14I illustrates a system console screen 1400I in an implementation. Screen 1400I depicts a plurality of chain code known to the blockchain network 106. Processes executing with administrative privileges can install and/or instantiate these chain codes in various peer server(s) 136 using the process flows described herein above with reference to FIG. 4A. Screen 1400I further depicts, inter alia, the claimed blockchain with different blocks or nodes of the blockchain represented by color QR codes in the user interface. The QR codes encode requested information, e.g. parameter values, etc., about a reported event as received and incorporated into the nodes of the blockchain, and are colored to encode the nodes according to the trusted server responsible for the nodes. For example, as depicted by Screen 1400I, the first three nodes 1401I, 1402I, 1403I of the blockchain are QR codes representing event data from owner "Pfizer" in a first color. A subsequent node 1404I of the blockchain represents event data from owner "Walgreens" in a second color. A final node 1405I in the depicted blockchain represents event data from owner "Dr. Gumby" in a third color. A visual depiction using color is used in one implementation to represent how the various nodes are coded into groupings based upon an owner, e.g., a trusted sever owner or member of the blockchain, and to contrast various nodes groups from one another.

Definitions

As used herein, the term "module" refers to a processor that receives information characterizing input data and generates an alternative representation and/or characterization of the input data. A neural network is an example of a module. Other examples of a module include a multilayer perceptron (MLP), a feed-forward neural network, a recursive neural network, a recurrent neural network, a deep neural network, a shallow neural network, a fully-connected neural network, a sparsely-connected neural network, a convolutional neural network that comprises a fully-connected neural network, a fully convolutional network without a fully-connected neural network, a deep stacking neural network, a deep belief network, a residual network, echo state network, liquid state machine, highway network, maxout network, long short-term memory (LSTM) network, recursive neural network grammar (RNNG), gated recurrent unit (GRU), pre-trained and frozen neural networks, and so on. Yet other examples of a module include individual components of a convolutional neural network, such as a one-dimensional (1D) convolution module, a two-dimensional (2D) convolution module, a three-dimensional (3D) convolution module, a feature extraction module, a dimensionality reduction module, a pooling module, a subsampling module, a batch normalization module, a concatenation module, a classification module, a regularization module, and so on. In implementations, a module comprises learnable submodules, parameters, and hyperparameters that can be trained by back-propagating the errors using an optimization algorithm. The optimization algorithm can be based on stochastic gradient descent (or other variations of gradient descent like batch gradient descent and mini-batch gradient descent). Some examples of optimization algorithms used by the technology disclosed include Momentum, Nesterov accelerated gradient, Adagrad, Adadelta, RMSprop, and Adam. In implementations, a module is an activation module that applies a non-linearity function. Some examples of non-linearity functions used by the technology disclosed include a sigmoid function, rectified linear units (ReLUs), hyperbolic tangent function, absolute of hyperbolic tangent function, leaky ReLUs (LReLUs), and parametrized ReLUs (PReLUs). In implementations, a module is a classification module. Some examples of classifiers used by the technology disclosed include a multi-class support vector machine (SVM), a Softmax classifier, and a multinomial logistic regressor. Other examples of classifiers used by the technology disclosed include a rule-based classifier. In implementations, a module is a pre-processing module, such as an input module, a normalization module, a patch-extraction module, and a noise-addition module. In implementations, a module is a post-processing module, such as an output module, an estimation module, and a modelling module. Two modules differ in "type" if they differ in at least one submodule, parameter, or hyperparameter. In some implementations, certain modules are fixed topology modules in which a certain set of submodules are not evolved/modified and/or only evolved/modified in certain generations, and only the interconnections and interconnection weights between the submodules are evolved.

Any other conventional or future-developed neural networks or components thereof or used therein, are considered to be modules. Such implementations will be readily apparent to those skilled in the art without departing from the spirit and scope of the technology disclosed.

As used herein, the term "submodule" refers to a processing element of a module. For example, in the case of a fully-connected neural network, a submodule is a neuron of the neural network. In another example, a layer of neurons, i.e., a neuron layer, is considered a submodule of the fully-connected neural network module. In other examples, in the case of a convolutional neural network, a kernel, a filter, a feature extractor, an activation function, a pooling operation, a subsampling operation, and a regularization operation, are each considered submodules of the convolutional neural network module. In some implementations, the submodules are considered as modules, and vice-versa. As used herein, "photo" can include an electronically formatted digitized image or sequence of images of a user captured by electronic means and stored in any of a variety of formats, such as without limitation jpg, tif, gif, png, raw, mpeg (video) and others.

A reporting application includes executable machine instructions that when executed by a processor perform at least initiating one or more reporting action(s). Some types of reporting actions are a regulatory reporting process, filling out part of a regulatory report, concluding at least instructing closing an existing regulatory reporting process, modifying a parameter of metadata stored in association with a regulatory reporting process, submitting a full regulatory report, reporting notice of an anomaly to a market actor, other reporting, and combinations thereof.

A remedial application includes executable machine instructions that when executed by a processor perform at least initiating one or more remedial action(s). Some types of remedial actions are changing the regulatory status of a pharmacy, initiating a freeze on a lot or production run of medications in the event of consistent and verifiable adverse reports, notifying an interested third party, and order more substance, signal that a set of transactions is no longer permitted, change regulatory status of a pharmacy, blocking or disallowing transacting on the blockchain of either potentially counterfeit lot(s), other remedial actions, and combinations thereof.

An input data collecting application includes executable machine instructions that when executed by a processor perform at least initiating one or more data collection. Some types of data collection actions are displaying a prompt to a client to scan a barcode with the camera of a device, other types of sensed data collection, and combinations thereof.

An event type data is at least one selected from a set of a missing pill bottle(s), a mis-delivery of a therapeutic(s) stored on a blockchain, a mis-delivery of a medical service(s) delivered, a mis-coding of a therapeutic(s) or a service(s) properly delivered, an adulterated substance(s), a delivery(ies) not made, and a patient(s) sick or dead, or an adverse event(s) or product problem(s), other types of events identifiable from data, and combinations thereof.

Sensed information about a situation at a site includes detecting a presence of an adulterating substance, such as metallic or glass filings, medication color, a marking on a pill, foul or repugnant odors, an empty vial, a discolored contents, a cracked vial, a damaged packaging, a precipitated medicine inside, a mislabeled vial, other types of sensed information, and combinations thereof.

A system implementation of the technology disclosed includes one or more processors coupled to the memory. The memory is loaded with computer instructions which, when executed on the processors, cause evolution of a deep neural network structure.

The deep neural network structure disclosed herein includes a plurality of modules and interconnections among the modules. Examples of deep neural network structures include without limitation AlexNet, ResNet, Inception, WaveNet, PixelCNN, GoogLeNet, ENet, U-Net, BN-NIN, VGG, LeNet, DeepSEA, DeepChem, DeepBind, DeepMotif, FIDDLE, DeepLNC, DeepCpG, DeepCyTOF, and SPINDLE.

Particular Implementations

In one implementation, we disclose a method of authenticating requestors and granting access to a permissioned blockchain network shared among enterprise entities, that includes: receiving from a requestor's user application, by a registry server, a first request by a requestor to access the permissioned blockchain; authenticating the requestor based at least in part upon submissions of evidence by the requestor; and granting a distributed digital credential to the requestor to access the permissioned blockchain network.

Some implementations of the method further include receiving by the registry server, a second request by the requestor to withdraw from accessing the permissioned blockchain; rescinding the distributed digital credential issued to the requestor; and removing personally identifiable information of the requestor.

In one implementation, rescinding the distributed digital credential issued to the requestor can further include: responsive to receiving a request from a requesting user application to be forgotten, revoking the distributed digital credential and deleting a trusted triple data structure corresponding to the user application, the trusted triple data structure comprised of: (a) a public key, (b) a link to an enterprise application on a server for which the requestor is being authenticated, and (c) one or more third-party accreditations in the claim as validated; thereby enabling the requesting user to manually withdraw their credential; and deleting from private storage any identity documentation corresponding to the requestor.

In one implementation, transactions from a requesting user that has withdrawn their credential remain in the blockchain and tied to an organization to which the requesting user was assigned with name, license and personally identifiable information of the requesting user removed.

In one implementation, the first request includes: (i) identity documentation identifying the requestor and captured by the user application at a time of making the request and (ii) claims made by an entity administrator supporting a role, as determined by rules of a trust framework adopted by network members.

In one implementation, authenticating the requestor can further include: storing in a private storage by the registry server, the (i) identity documentation and (ii) claims.

In one implementation, authenticating the requestor can further include: redacting pictures captured of the requestor from the (i) identity documentation and (ii) claims; and sending the identity documentation and claims without pictures via an external validator interface to a validator server.

In one implementation, the method further includes validating by the validator server, claims made by an entity administrator, as determined by rules of a trust framework by: checking by the validator server, a state board of pharmacy database to verify that a pharmacist applying for an ID is really the pharmacist in charge of the pharmacy they claim to manage.

In one implementation, the method further includes the validator server issuing one or more challenges to the requesting user; and using responses from the requesting user in validating the (i) the identity documentation and (ii) the claims made by an entity administrator.

In one implementation, the challenges are selected from a set comprising of questions asked through a secure channel, requests to take a photo of themselves holding an identification, invert or flip the identification in a subsequent photo.

In one implementation, granting a distributed digital credential further includes: generating by the registry server and sending to the user application a one-time token for creating a public-private key pair.

In one implementation, the registry server further obtains a digital ID comprising a pseudonymized user ID of the requesting user authenticated from a public key and digital signature.

In one implementation, granting a distributed digital credential further includes: storing by the registry server a credential in a public key registry as a trusted triple data structure comprised of (a) the public key, (b) a link to an enterprise application on a server for which the requestor is being authenticated, and (c) one or more third-party accreditations in the claim as validated.

In one implementation, no registry node contains credentials for all users permitted access to the permissioned blockchain.

In one implementation, the method further includes revoking the credential in the blockchain network responsive to receiving notification from the validator server that an event affecting the claims has been detected or input of a manual review has been received.

In one implementation, an event affecting the claims includes, checking by external validator, a state board of pharmacy database on an expiry of a 24-hour timer for any changes in listed pharmacists in charge for each pharmacy and notifying the registry server to make any necessary revocations.

In one implementation, the method further includes providing at least some of the identity documentation in a private storage of the registry server to an external server for audit.

In one implementation, a machine intelligence process is used to authenticate the requestor using a trained neural network classifier trained using a training set of example submissions of evidence and ground truth outcomes.

In one implementation, the method further includes identifying patterns in data points indicating clusters of data, and applying a label to each cluster; and continuously training a classifier including a neural network with at least some of the clusters and labels.

In one implementation, values for one or more labels associated with the training set are determined from a set including at least a plurality of counterfeit, expired, hacked, intentional adulteration, unfit for authentication, and fraudulent activity.

In another implementation, we disclose a method of granting and sharing credentials in a shared private permissioned blockchain shared among network members of a blockchain network. The method can include implementing, by a registry server of a distributed network of security registry nodes that manage access to a shared private permissioned blockchain data structure maintained by the network members, a claims verification process. The claims verification process can include: receiving, by the registry server and from a requesting user application, a request to authenticate identity claims of a requesting user to permit access to data stored in blocks in the shared private permissioned blockchain shared among network members. The request can include: (i) identity documentation identifying the user and captured by the user application at a time of making the request and (ii) claims made by an entity administrator supporting a role, as determined by rules of a trust framework adopted by the network members. The verification process further includes storing in a private storage by the registry server, the (i) identity documentation and (ii) claims; sending the identity documentation and claims via an external validator interface to a validator server. Upon obtaining, by the registry server via the external validator interface and from the validator server, an approval validating: (i) the identity documentation and (ii) the claims made by an entity administrator, generating and sending to the user application a one-time token for creating a public-private key pair. Upon receipt from the user application, of a public key of a public-private key pair generated by the user application using the one-time token, granting, by the registry server, a credential in the blockchain network based upon the validation of (i) the identity documentation and (ii) the claims, the credential being stored in a public key registry at the registry server as a trusted triple data structure comprised of (a) the public key, (b) a link to an enterprise application on a server corresponding to the registry server, and (c) one or more third-party accreditations in the claim as validated. Responsive to a receiving, by the registry server and from a blockchain network member, a verification request to verify the credential submitted by the requesting user in an electronic communication with the blockchain network member, providing, by the registry server, the trusted triple data structure as verification of the credential to the blockchain network member as requested; to enable the blockchain network member to provide data from blocks stored in the shared private permissioned blockchain data structure to only credentialed users; wherein no registry node contains credentials for all users permitted access to the shared private permissioned blockchain data structure.

In one implementation, we disclose a system for cross-authenticating non-credentialed devices and trusted blockchain enabled applications and gathering information for a blockchain network. The system comprises an interface to a trusted source system for publishing to a server of the trusted source system a mobile application being provided to the non-credentialed devices and a trusted server of a plurality of blockchain nodes having access to a blockchain ledger storing at least pointers to a plurality of documents. The trusted server includes a processor and software that implement generating a request for information uniquely identified by a first randomized token and a link to the mobile application published to the trusted source system authenticating the trusted server as trusted and sending using a first communications modality to at least one recipient non-credentialed device. The processor and software also implement requesting secondary verification information of the non-credentialed device via a copy of the mobile application retrieved by the non-credentialed device from the trusted source system and authenticating the non-credentialed device as an authenticated recipient. An indication of receipt of the request for information from the mobile application as installed by the non-credentialed device as an authenticated recipient is received. The processor and software also implement generating a web page for receiving the information as requested, the web page uniquely identified by a second randomized token mapped to the first randomized token and receiving from the non-credentialed device as an authenticated recipient the information as requested via the web page.

In one implementation, the system further includes sharing public keys by the trusted server with the non-credentialed device as an authenticated recipient. In one implementation, the first communication modality comprising email. In one implementation, the first communication modality comprising a push notification. In one implementation, the system further includes the trusted server storing in a persistent storage a mapping of the first randomized token to the second randomized token. In one implementation, the system further includes the trusted server resending the request for information to the non-credentialed device as an authorized recipient upon expiry of a time limit to respond. In one implementation, the system further includes terminating by the trusted server, authentication of the non-credentialed device as an authorized recipient upon expiry of a time limit to respond. In one implementation, the system further includes terminating by the trusted server, authentication of the non-credentialed device as an authorized recipient upon receiving the requested information. In one implementation, the secondary verification information further includes the trusted server receiving at least one of a one-time code sent to an email address, a one-time code sent to a phone number via push notification, a one-time code sent encrypted to an email address, and a time-based code with shared secret.

In one implementation, we disclose a computer-implemented method of efficiently implementing a blockchain pharmaceutical regulatory compliance system using a trained exception handling classifier on a data processor with a target architecture. The method includes detecting block-level events stored on a block chain, the events selected from a set of a missing pill bottle, an adulterated substance, a delivery not made, and a patient sick or dead. The method also includes triggering an application to perform one or more actions selected using an ensemble of neural network classifier(s) from a set of submit a regulatory report, notify an interested third party, and order more substance.

In one implementation, the method further includes selecting the action using an exception handling classifier trained using a training data set comprising a plurality of ground truth correspondences of drug identifications, exception events, and remedial actions.

In one alternative implementation, a first neural subnetwork is trained to classify input from a client sensed information into a block level exception event and a second neural subnetwork is trained to provide a remedial action.

In one implementation, the classifier is trained with a ground truth dataset comprising pairings of drug identifications with exception events including sensed discrepancies in the drug or its packaging, and remedial actions including prompts and instructions. In this implementation, the method further includes using the classifier, identifying a drug as an injectable drug in a vial, and triggering an action including prompting the user to specify sensed discrepancies selected for the drug identified. In one implementation, the sensed discrepancies include one or more selected from an empty vial, a discolored contents, a cracked vial, a damaged packaging, a precipitated medicine inside, and a mislabeled vial.

In one implementation, the classifier is trained with a ground truth dataset comprising pairings of investigative situations with exception events including sensed discrepancies in the drug or its packaging, and remedial actions including capturing evidence of the discrepancies in the drug or its packaging. In this implementation, the method further includes using the classifier, identifying a drug or its packaging as exhibiting a discrepancy, and triggering an action including prompting the user to capture an image, record a sound or scan a bar code.

In one implementation, the classifier is trained with a ground truth dataset comprising pairings of drug identifications with exception events including sensed discrepancies in the drug or its packaging, and remedial actions include prompts and instructions; the method further comprising: using the classifier, identifying a drug as a radioactive drug in "wet packaging", and triggering an action including prompting a user to step away from the drug and to notify a safety officer. In one implementation, the method further includes the classifier identifying a different drug as a non-radioactive injectable drug, and triggering an action including prompting to use caution to avoid getting cut by glass, but if possible, remove vial from outer carton.

In one implementation, the classifier is trained with a ground truth dataset comprising pairings of investigative situations with exception events including sensed discrepancies in the drug or its packaging, and remedial actions include capturing evidence of the discrepancies in the drug or its packaging. In this implementation, the method further comprises using the classifier, identifying two or more discrepancies of a drug shipped to different pharmacies by different wholesalers and each exhibiting evidence of a same discrepancy, and triggering an action including generating reporting escalating the discrepancy to the manufacturer as a cluster.

In one implementation, the method further includes the classifier identifying a common lot or other manufacturing characteristic in problematic vials, and triggering an action including generating a warning to the manufacturer that the common lot potentially has more problems.

In one implementation, the method further includes the classifier assigning weights and likelihoods to a recall and generating a report including the weights and likelihoods to the manufacturer.

In one implementation, the method further includes the classifier sharing the report including the weights and likelihoods to a regulatory authority; thereby enabling the regulatory authority lacking visibility into a supply chain to identify potential recalls.

In one implementation, the classifier is trained with a ground truth dataset comprising pairings of investigative situations with exception events including sensed discrepancies in the drug or its packaging, and remedial actions including capturing evidence of the discrepancies in the drug or its packaging. In this implementation, the method further comprises using the classifier, identifying a duplicate 2D barcode identifier in a first city identical to one in a second city as indicating a potentially counterfeit lot(s), and triggering an action of blocking or disallowing transacting on the blockchain of either potentially counterfeit lot(s).

In one implementation, the method further includes the classifier detecting whether barcode scans were separated by a specific period of time or threshold, and assigning a higher weight to a first temporally occurring scan as original and probably safe to administer, otherwise, the classifier assigning a like weight to the first and second temporally occurring scans; thereby indicating that each is counterfeit.

In one implementation, the classifier is trained with a ground truth dataset comprising pairings of investigative situations with exception events including sensed discrepancies in the drug or its packaging, and remedial actions including capturing evidence of the discrepancies in the drug or its packaging. In this implementation, the method using the classifier, identifying an aggregate number of orders added to the blockchain over a unit time period indicating a shortage, and triggering an action of generating a report to suppliers indicating the shortage; thereby enabling suppliers to pull forward the scheduled manufacturing runs.

In one implementation, the method further includes retrieving data from block-level events storing data from (i) exception reports made to a regulatory body from a blockchain; or (ii) databases in a supply chain.

In another implementation, we disclose a computer-implemented method of preparing a plurality of neural network systems to recognize exception events and drug identifications and to trigger applications that take remedial actions on a data processor with a target architecture. The method includes generating at a time to, a training data set comprising 50,000 to 1 billion exception events, each exception event labelled with sensed discrepancy information and with drug identifications, and corresponding ground truth remedial actions. The method also includes subdividing the drug identifications into one or more overlapping drug categories. Training a first set of drug classifier neural networks with the drug identifications and the drug categories is also part of the method. The method also includes training a first set of exception classifier neural networks with the sensed information, drug identification information, drug category information, and the corresponding ground truth remedial actions. The method further includes saving parameters from training the recurrent neural networks in tangible machine readable memory for use in reporting or responding to exceptions in pharmaceuticals handling.

In one implementation, the method further includes generating a second training data set at a time t1, later in time than to, including additional exception events reported after time t0; and using the second training data set, performing the subdividing, training and saving steps to retrain the classifier neural networks and the training recurrent neural networks, thereby enabling the classifiers to learn from subsequent remedial actions.

In one implementation, the generating further includes retrieving (i) the exception events and sensed discrepancy information from block-events stored in a pharmaceutical blockchain; and/or (ii) the drug identifications from a commercial supplier database.

In one implementation, the sensed discrepancies include one or more selected from an empty vial, a discolored contents, a cracked vial, a damaged packaging, a precipitated medicine inside, and a mislabeled vial. In one implementation, the exception events are selected from a set of missing pill bottle, an adulterated substance, allergic reaction, a delivery not made, and a patient sick or dead. In one implementation, the remedial actions are selected from a set of instruct user to capture an image, record a sound or scan a bar code, prompt user with instructions, submit a regulatory report, notify an interested third party, and order more substance. In one implementation, the drug categories are selected from a set of opioids, injectable, OTC, prescription, antibiotic, steroid, antihistamine, capsule, tablet, vaccine, and nuclear.

In one implementation, the drug classifier neural networks and the exception classifier neural networks are recursive neural networks (RNN) based on long short term memory (LSTM).

In one implementation, the drug classifier neural networks and the exception classifier neural networks are trained using a combination of current exception events and additional noise data.

In one implementation, the method also includes generating in the training data set, images of the drugs in unadulterated and adulterated form; applying a multilayer convolution and pooling processor and producing reduced dimensionality images from the images of the drugs; training a first set of convolutional neural networks using the reduced dimensionality images and ground truth data indicating whether the images correspond to adulterated drugs or unadulterated drugs.

In another alternative implementation, we disclose a method of recognizing discrepancies in drug images in adulterated and unadulterated states and to trigger applications that take remedial actions on a data processor with a target architecture. The method includes applying a multilayer convolution to a plurality of images of drugs and pooling processor and producing reduced dimensionality images, including first and second reduced dimensionality images, from the plurality of drug images including a drug image of the drug in an adulterated state and a drug image of the drug in an unadulterated state. The method can also include processing a pair of first and second reduced dimensionality images using a first neural network to produce estimated classification parameters, using pairs of first and second reduced dimensionality images, estimated classification parameters for the first and second reduced dimensionality images, image data for presentation, and labeled ground truth conclusions indicating whether the classification parameters correspond to a drug in an adulterated state or a drug in an unadulterated state. The method also includes saving the parameters in a tangible machine readable memory for use in drug image recognition.

In one implementation, the parameters are selected from a set of color, shape, size, markings, texture.

In one implementation, the method further includes capturing drug images of drugs in an adulterated state and in an unadulterated state.

In a further alternative implementation, we disclose a method of preparing sample pharmaceutical regulatory compliance for training of neural network systems on a data processor with a target architecture. The method includes accessing in regulatory agency reporting system a plurality of reports with parameters that specify: type of report; incident number provided by a regulatory authority; date of initial notification to the regulatory authority; date company determined product was illegitimate; classification of notification; name of product as it appears on the label; primary ingredients; drug use selected from a set of human, and other; drug description; strength of drug; dosage form; quantity; national drug code number; serial number; lot number; expiration date; for notification, description of event/issue; other reports submitted; company name and address; company category; unique facility number; and contact information. The method can also include generating between 50,000 and 1 billion exception event simulations, each simulation labeled with 5 to 15 selected parameters, including a drug identification. Saving the simulated exception events with labelled ground truth parameters indicating at least remedial events to be triggered for use in training a neural network in a pharmaceutical regulatory compliance system is also part of the method.

In one implementation, the type of report is selected from a set of initial notification, follow-up notification, and request for termination. In one implementation, classification of notification is selected from a set of counterfeit, diverted, stolen, intentional adulteration, unfit for distribution, and fraudulent transaction. In one implementation, the drug description is selected from a set of finished prescription drug, vaccine, plasma derivative, including one of coagulation factors, immunoglobulins, albumin, allergenic, including standardized and non-standardized, and multiple. In one implementation, dosage form is selected from a set of tablet, capsule, aerosol, oral liquid, sublingual, injectable, topical, suppository, other, and multiple. In one implementation, other reports is selected from a set of filed alert report, a biological product deviation report, a medical-watch report, none, and other. In one implementation, category is selected from a set of manufacturer, wholesale distributor, dispenser, and repackager.

In one implementation, the method further includes accessing additional parameters stored in a commercial supplier database; and using the additional parameters to generate the simulations.

In another alternative implementation, we disclose a method of securing clinical trial data on a data processor with a target architecture. The method includes receiving a request to manipulate clinical trial information in block-level clinical trial structures stored to a blockchain. Determining whether the request is made by a participant in a clinical trial or a scientist conducting a clinical trial can also be part of the method. The method also includes permitting access to the participant of a subset of the clinical trial information suitable for the participant, otherwise permitting access to the scientist of a different subset of the clinical trial information suitable for the scientist.

In one implementation, the request is a request to enter patient data. The method also includes locating a block on the chain in which the patient data relates; determining whether the request is authorized under a smart contract governing the use of the clinical trial blockchain; and adding the patient to the clinical trial whenever the request is authorized.

In one implementation, the request is a request to delete patient data. The method also includes locating a block on the chain in which the patient data relates; determining whether the request is authorized under a smart contract governing the use of the clinical trial blockchain; and deleting the patient from the clinical trial whenever the request is authorized.

In one implementation, the request is a request to order a specific substance for a patient in a clinical trial. The method further includes determining which group a patient is in and delivering correct amount of substance.

In implementations, the method also includes one or more of: (i) detecting a set of patient parameters after substance administration and gathering it back on the chain; (ii) mixing artificially generated patient data with real patient data in the block chain; (iii) detecting and adding longitudinal patient outcomes; or (iv) mixing multiple studies on a single block chain to perform meta-analysis.

In yet further alternative implementation, we disclose a method of finding additional instances of like events from a reported first event involving a first physical object. The method includes receiving by a trusted server having access permissions to a permissioned blockchain network, a report by an unverified source, the report identifying the first physical object. Establishing by the trusted server, a trusted interactive conversation with the unverified source, the trusted interactive conversation identified by a unique random token, wherein physical parameters of the first physical object are prompted for, and values for the physical parameters are returned can also be part of the method. The method can also include determining by the trusted server from the values for the physical parameters received, values for one or more associated block chain parameters using a machine intelligence process; and creating by the trusted server, using the values for one or more associated block chain parameters, a new block chain block. Further the method can include sending the new block chain block populated with at least some of the values for one or more associated block chain parameters in connection with the unique random token to be added to the permissioned blockchain network; thereby enabling other trusted servers with access to the permissioned blockchain network to provide indication of additional instances of like events based upon the values for one or more associated block chain parameters.

In one implementation, the machine intelligence process further includes determining associated block chain parameters using a trained neural network classifier trained using a training set of example physical parameter values and example associated block chain parameters.

In one implementation, the machine intelligence process further includes applying a semi-supervised statistical machine learner to documents linked to blocks stored with the permissioned blockchain network to develop patterns of data recognized from in the documents; using the semi-supervised statistical machine learner to encode blockchain data representing healthy states (Xh) and unhealthy states (Xu) to latent vectors representing block level data mapped into a latent vector space; and using the semi-supervised statistical machine learner to identify data points corresponding to blocks of a certain Mahalanobis distance from data clusters labelled as desirable.

In one implementation, the method further includes identifying patterns in the data points indicating clusters of data, and applying a label to each cluster; and continuously training a classifier including a neural network with at least some of the clusters and the labels.

In one implementation, the values for one or more associated block chain parameters are determined by aggregating information obtained from multiple blocks in the blockchain network selected by the machine intelligence process using the physical parameters.

In one implementation, the values for one or more associated block chain parameters are determined from a set including at least a plurality of Counterfeit, Diverted, Stolen, Intentional adulteration, Unfit for distribution, and Fraudulent transaction.

In one implementation, the values for physical parameters are detected from a set including at least a plurality of a presence of an adulterating substance, such as metallic or glass filings, medication color, a marking on a pill, foul or repugnant odors, an empty vial, a discolored contents, a cracked vial, a damaged packaging, a precipitated medicine inside, and a mislabeled vial.

In one implementation, the first event involving a first physical object is selected from a set of a missing pill bottle(s), a mis-delivery of a therapeutic(s) stored on a blockchain, a mis-delivery of a medical service(s) delivered, a mis-coding of a therapeutic(s) or a service(s) properly delivered, an adulterated substance(s), a delivery(ies) not made, and a patient(s) sick or dead in connection with a product, or an adverse reaction event(s) in connection with a product problem(s).

In one implementation, the method further includes the trusted server generating and providing the unique random token to the unverified source, accompanied by a link to a trusted application for making interactive requests for information of the unverified source.

In one implementation, the method further includes the link linking to a copy of the trusted application stored at an application store for download, the trusted application verifying the trusted server to the unverified source.

In one implementation, the method further includes providing by the trusted application an offer to the unverified source to login to the trusted server and receiving from the unverified source a login into the trusted server.

In one implementation, the method further includes completing two-factor identification verifying the unverified source to the trusted server.

In a still yet further alternative implementation, we disclose a method of finding additional instances of problem shipments from a problem report of a first damaged shipment, that includes receiving by a trusted server having access permissions to a permissioned blockchain network, a report by an unverified source, the report indicating one or more problems with the first damaged shipment. Establishing by the trusted server, a trusted interactive conversation having a unique random token, with the unverified source, wherein physical parameters of the first damaged shipment are prompted for, and values for the physical parameters are returned is also part of the method. The method further includes determining by the trusted server from the values for the physical parameters received, values for one or more associated block chain parameters; and creating by the trusted server, using the values for one or more associated block chain parameters, a new block chain block. The method finally includes sending the new block chain block populated with at least some of the values for one or more associated block chain parameters in connection with the unique random token to be added to the permissioned blockchain network.

In one implementation, the method further includes whereby the sending the new block chain block enables other trusted servers with access to the permissioned blockchain network to provide indication of additional instances of problem shipments based upon the values for one or more associated block chain parameters.

In one implementation, the method further includes the trusted server using a machine intelligence process to determine values for one or more associated block chain parameters from the values for the physical parameters received.

In one implementation of the method, the first damage shipment includes damaged packaging to a medication, further including determining using the neural network based trained classifier, other shipments of products of an increased probability of experiencing damage consistent with damage experience by the first damaged shipment.

In one implementation, the method further includes the trusted server using a smart contract implementing a classifier to determine values for one or more associated block chain parameters from the values for the physical parameters received.

In one implementation of the method, values for one or more associated block chain parameters are determined from a set including at least a plurality of Counterfeit, Diverted, Stolen, Intentional adulteration, Unfit for distribution, and Fraudulent transaction.

In one implementation of the method values for physical parameters are detected from a set including at least a plurality of a presence of an adulterating substance, such as metallic or glass filings, medication color, a marking on a pill, foul or repugnant odors, an empty vial, a discolored contents, a cracked vial, a damaged packaging, a precipitated medicine inside, and a mislabeled vial.

In one implementation of the method a problem shipment has experienced an event selected from a set of a missing pill bottle(s), a mis-delivery of a therapeutic(s) stored on a blockchain, a mis-delivery of a medical service(s) delivered, a mis-coding of a therapeutic(s) or a service(s) properly delivered, an adulterated substance(s), a delivery(ies) not made, and a patient(s) sick or dead in connection with a product, or an adverse reaction event(s) in connection with a product problem(s).

In one implementation, the method further includes the trusted server initiating the trusted interactive conversation by generating the unique random token and providing to the unverified source the unique random token accompanied by a link to an application making interactive requests for information of the unverified source.

In one implementation, the method further includes the link linking to a copy of the application stored at an application store for download, the application verifying the trusted server to the unverified source.

In one implementation, the method further includes providing by the application an offer to the unverified source to login to the trusted server and receiving from the unverified source a login into the trusted server.

In one implementation, the method further includes completing two-factor identification verifying the unverified source to the trusted server.

In a still yet further alternative implementation, we disclose a method of initiating commanded actions responsive to reported events in which intervention is desired that includes receiving by a trusted server having access permissions to a permissioned blockchain network, an indication by an unverified source, the indication identifying an occurrence or a probability of occurrence of one or more events in which intervention is desired. The method further includes establishing by the trusted server, a trusted interactive conversation having a unique random token, with the unverified source, wherein physical parameters of the one or more events are prompted for, and values for the physical parameters are returned. Further, the method can include detecting using a machine learning algorithm a first state and a probability of the state based upon the values for the physical parameters; wherein the first state further prompts a first notification to take an action. Also part of the method is capturing by the trusted server an indication that the action prompted has occurred; and creating by the trusted server, using the first state, the first notification to take an action, and the values for the physical parameters, a new block chain block. The method finally includes sending the new block chain block populated with at least some of the values for one or more the first state, the first notification to take an action, and the values for the physical parameters in connection with the unique random token to be added to the permissioned blockchain network; thereby enabling other trusted servers with access to the permissioned blockchain network to provide indication of actions taken in connection with additional instances of like events.

In one implementation, the method further includes detecting a second state indicating an incorrect response to the first state has occurred, and using the machine learning algorithm to select a further action based upon a the detected existence of the second state.

In one implementation, the method further includes the trusted server receiving additional information including values for the physical parameters, using the machine learning algorithm to select a further action based upon a detected existence of a second state; and prompting second notification according to the second state.

In one implementation of the method, the second state corresponds to the first notification is in error, the method further including the second notification (i) cancels the first notification; or (ii) amends the first notification.

In one implementation of the method the trusted server generating the new block further includes the new block indicating a Request generated, indicating that the first notification is created and sent to one or more recipients; Response recorded, indicating that at least one recipient has responded to the first notification; Request expiration approaching, indicating a reminder event; Request expired, indicating the request expired and can no longer be directly responded to without a fresh request being generated; or Request invalidated, indicating that a request that has not been responded to can be invalidated, or that no response to it may be recorded.

Use Case

Under the US statutes associated with Drug Supply Chain Security Act (DSCSA)/Drug Quality and Security Act (DQSA), wholesalers and dispensers of drugs are required to submit Form FDA 3911 to the FDA, as well as separately notify immediate trading partners, when illegitimate products are discovered. Separate channels are specified for reporting by prescribers and patients, such as MedWatch, the FDA's safety information and adverse event reporting program. One implementation of a neural network enabled interface server as a blockchain proxy user facilitates mandated reporting, improving speed, ease of use, reliability, and security. As a broader concept, this is an exception handling and root cause analysis system driven by a neural network enabled interface server and blockchain, with significant implications for federal safety and compliance reporting. For example within the drug and healthcare reporting field, this approach could address reporting among both professionals and consumers: FDA: Field Alert Report (FAR), FDA: Biological Product Deviation Report (BPDR), FDA: Form 3500 (Medwatch, voluntary reporting by healthcare professionals, consumers, and patients), FDA: Form 3500A (Medwatch, mandatory reporting by IND reporters, manufacturers, distributors, importers, and user facilities personnel), FDA: Form 3500B (Medwatch, voluntary reporting by consumers), FDA: Reportable Food Registry, FDA: Vaccine Adverse Event Reporting System (VAERS), FDA: Investigative Drug/Gene Research Study Adverse Event Reports, FDA: Potential Tobacco Product Violations Reporting (Form FDA 3779), USDA APHIS Center for Veterinary Biologics Reports, USDA Animal and Plant Health Inspection Service: Adverse Event Reporting, USDA FSIS Electronic Consumer Complaints, DEA Tips, Animal Drug Safety Reporting, Consumer Product Safety Commission Reports, State/local reports: Health Department, Board of Pharmacy, and others.

Implementations incorporating machine/barcode reading for faster initiation and better data integrity, neural networks implementing categorization and linking to historical challenges, and blockchain including timestamping, tracking, thereby driving a near-real-time resolution system. Certain implementations enable achieving identification of suspect products and, products with a high risk of illegitimacy. Certain implementations enable achieving notification of illegitimate products and products with a high risk of illegitimacy.

Implementations can provide stakeholders the most likely paths to resolve the issue at the micro and macro levels—determining the proper course of action for the specific challenge, while intelligently and selectively broadcasting notifications of events (such as recalls) to relevant subsets of subscribers. Using blockchain, system implementations can generate notifications to parties upstream and downstream via text and/or email and can enable counterparties to both resolve exceptions and link them to related exceptions (thus identifying larger event patterns).

One implementation of a neural network enabled interface server works with a mobile device and eliminates the need to transcribe data from the bottle. A neural network enabled interface server implementation will be trained to readily determine whether or not the medicine in question is in a pill form and suggest responses like "missing pills" or "crushed or broken pills" that are germane to that medicine, whereas a liquid medicine will present different choices.

Trading partners are not given visibility into all relevant transactions; instead, one implementation employs differential privacy to send reports of similar events. Along with fulfilling the minimum information requirements of FDA Form 3911, one implementation enables the functionality for trading partners to ask extemporaneous questions; one deep learning implementation can employ those questions to ask similar questions in similar situations.

One implementation of a neural network enabled interface server is able to gather additional data, flag out-of-spec assets, identify ecosystem-level patterns, and engage in root-cause analysis. Such implementations employ cluster identification, free-form typical input learning, convolutional neural network (CNN), and bad actor identification and others.

One implementation can receive photos of barcodes taken by a third party, optical character recognition of the human-readable label, and XML or other machine files with the same information. One implementation provides pill recognition based on publicly available image recognition frameworks. One implementation provides the reporting party with a series of deep learning driven modal screens, enabling participants to accurately and rapidly regulators and counterparties ("trading partners") of problems.

Other Use Cases

Implementations of a block chain trained classifier include drug manufacturers, drug wholesalers, hospitals, and pharmacies doing business in the United States and other countries. Implementations incorporating cluster analysis, root cause, block chain and convolutional neural network as a trained classifier can provide prompt contemporaneous notification, compliance reporting, epidemiology, surveillance, and exception handling. Additional use cases include implementations used for food safety, medical devices, and vaccines.

The terms and expressions employed herein are used as terms and expressions of description and not of limitation, and there is no intention, in the use of such terms and expressions, of excluding any equivalents of the features shown and described or portions thereof. In addition, having described certain implementations of the technology disclosed, it will be apparent to those of ordinary skill in the art that other implementations incorporating the concepts disclosed herein can be used without departing from the spirit and scope of the technology disclosed. Accordingly, the described implementations are to be considered in all respects as only illustrative and not restrictive.

Legal documents. Lawyers rely heavily on burdensome paper trails and myriad third-party services to track legal filings and handle disclosures. One neural network enabled interface server implementation clusters discrepancies or potential conflicts of interest among various parties, and send notifications to relevant parties. (For example, applying natural language processing [NLP] and clustering analysis to identify business records filed in two separate cases that substantially overlap, or clustering names of interested parties would reveal a scenario where a law firm may be acting for more than one client in separate but related matters. In these cases, the neural network enabled interface server would send notifications to court officials.)

Patent filings and lawsuits. Patent trolling has increasingly been used as a means to stifle rather than encourage innovation; over the last several years, Vermont, Nebraska, Minnesota, Wisconsin, and Idaho have all implemented legislation or taken other steps to punish bad faith assertions of patent infringement. By analyzing all patent filings over time, as well as accepting reports of bad faith infringement threats (either submitted by individuals through a web or mobile client, or via machine-to-machine [M2M] reports from court IT systems), one neural network enabled interface server implementation would notify the U.S. Patent Office and other stakeholders of questionable patent filings by bad actors (identified through clustering reports of frivolous lawsuits and performing NLP to identify overly broad or non-specific filings).

Financial documents and investments. By analyzing the filings sent to one or more regulators such as the SEC, one neural network enabled interface server implementation identifies and sends notifications regarding discrepancies or unusual correlations among filings—not just to the regulator, but also to a submitter of multiple filings where the discrepancy may be unintended.

Anti-money laundering. Under the Bank Secrecy Act of 1970, financial institutions in the United States are obligated to keep records of (and in some cases file reports of) cash purchases of negotiable instruments, as well as report suspicious activity. By performing NLP on Financial Crimes Enforcement Network (FinCEN) submissions and related media, one neural network enabled interface server implementation identifies partial name and account matches, match multi-step transactions, and identifies unusual bursts of activity across a variety of factors, including institution and geography.

Import/export and customs. From perishable goods to electronic components, imported and exported goods are covered by a wide range of regulatory and disclosure requirements, with stakeholders including trading partners, customs officials, shipping companies, and state and federal regulators for specific industries. One neural network enabled interface server implementation generates notifications on potential faulty, illegitimate, or illegal products being moved across borders.

Food safety. In the United States, food safety is covered by a wide range of agencies, including the USDA (meat and poultry products), FDA (all other foods marketed in interstate commerce), EPA (pesticide products), the National Marine Fisheries Service (seafood inspection and grading), and myriad other agencies as well as state and local regulatory systems. Reporting systems include the aforementioned Medwatch, the Reportable Food Registry, and many other ad hoc approaches such as call centers. By funneling these reports (including geographies, food consumed, and medical symptoms) into the blockchain, either directly or through machine-to-machine (M2M) connections, one neural network enabled interface server implementation identifies clusters across various reports arising from potentially related instances, and sends notifications to appropriate authorities. By leveraging user-submitted images (e.g. of food labels and spoilage) and convoluted neural networks, one neural network enabled interface server implementation generates conclusions and deploy notifications to the relevant health authorities.

Diamonds. The prevalence of blood diamonds—diamonds mined in war zones and sold to further illegal activities or atrocities—has resulted in the need for various companies throughout the global diamond supply chain to document the provenance of their gems. By clustering variables such as weight and provenance, one neural network enabled interface server implementation identifies suspicious transactions and notify customs officials and industry groups where blood diamonds might be making their way into the legitimate supply chain.

Radioactive materials. The global tracking of fissile materials poses a unique challenge to world governments. On a blockchain with smart contracts that adhere to national policies as well as the Treaty on the Non-Proliferation of Nuclear Weapons, this inventory could be tracked in a way that would prevent bad actors from altering records after they have been created. A neural network enabled interface server implementation generates notifications related to unusual activity or suspicious clustering to a predefined national or international overseeing body, such as the Nuclear Regulatory Commission or the International Atomic Energy Agency.

Specific ideas of networks and actions further includes: (A) Supply chain management systems, e.g., (i) Transaction of a good from one party to another; (ii) Request for information about a supply chain participant, an item in the supply chain, or a transaction/event in the supply chain, i.e., RFI dispatched to appropriate individual, who adds in the appropriate missing information, and (iii) Exception handling for errors that occur in the supply chain (e.g. a delivery was late, what does the person in charge at the delivering company say caused it); (B) Cyber security systems, e.g., (i) Anomalous event detected in a network, a human enters, (a) Threat assessment of the anomalous event (b) Actions taken to mitigate the threat; (C) 2FA systems, e.g., (i) Log-in to device, dispatch notification to a second semi-trusted channel; (D) System for monitoring "critical infrastructure" (think power plants, networks infrastructure) (a) Anomalous event detected in infrastructure, a human enters (i) Threat assessment of the anomalous event (ii) Actions taken to mitigate the threat; (E) Systems for monitoring or logging patient's health, e.g., Patient's implanted EKG reports the patient's heart has flatlined. System sends notification to patient's phone asking if they are still alive. "No response" transaction is logged after 10 minutes if they don't respond. If they do respond, "false positive" transaction is logged; (F) Banking systems, e.g., (a) Anomalous event detected in account activity, a human enters, (i) Threat assessment of the anomalous event, (ii) Actions taken to mitigate the threat; (b) Unlabeled transaction appears in an account, e.g., (i) Message dispatched to account administrator to capture additional information about the transaction, (G) Insurance systems of record, (a) Blockchain system detects that an event that was covered by insurance has occurred (e.g. hospitalization), (i) Sends an oraculus request to a patient and/or their care team to gather more information about what exactly happened; (H) Social media networks, (I) Approval of actions, e.g., (i) A user in a blockchain network carries out a transaction X, an oraculus request is sent to a party authorized to approve the transaction (e.g. FDA), and they can approve/deny; (J) General abstractions of the info gathering concept, (K) Critical system/asset monitoring (networks, power plants, people), (i) Alert/filter out anomalies, e.g., (a) Gathers training data for machine learning, (L) Exception handling, (i) A transaction is attempted between two parties and fails, additional information is needed for how to proceed following the failed transaction, (ii) Networks, e.g., (a) Supply chain; (M) Approval of transaction, (i) Transaction of material or data is proposed by party A and B, out-of-network party C needs to approve transaction, e.g., (a) Party C can be an AI, (b) Gathers training data for an AI that's a digital regulator; (ii) Networks, e.g., (a) Information systems e.g. social networks, (b) Trade/supply chain, (c) Log in/2FA, (N) Event-driven information gathering, (i) Blockchain system detects that an event has occurred (e.g. hospitalization), (a) Sends an oraculus request to a patient and/or their care team to gather more information about what exactly happened, (ii) Networks, e.g., (a) Banking transactions, (b) Insurance claims, (c) Supply chain, and others.

This system implementation and other systems disclosed optionally include one or more of the foregoing features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

Other implementations may include a non-transitory computer readable storage medium storing instructions executable by a processor to perform actions of the system described above. Each of the features discussed in the particular implementation section for other implementations apply equally to this implementation. As indicated above, all the other features are not repeated here and should be considered repeated by reference.

The preceding description is presented to enable the making and use of the technology disclosed. Various modifications to the disclosed implementations will be apparent, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein. The scope of the technology disclosed is defined by the appended claims.

We claim as follows:

1. A method, including:
receiving from a requestor, a first request by the requestor to access a permissioned blockchain network, wherein the first request includes: (i) identity documentation identifying the requestor, (ii) one or more claims, and (iii) one or more submissions of evidence;
authenticating the requestor based at least in part upon the one or more submissions of evidence, including:
redacting pictures captured of the requestor from at least (i) the identity documentation and (ii) the one or more claims; and
sending the identity documentation and the one or more claims without pictures to a validator server.

2. The method of claim 1, further including:
granting a distributed digital credential to the requestor to access the permissioned blockchain network.

3. The method of claim 2, further including:
receiving from the requestor, a second request by the requestor to withdraw from accessing the permissioned blockchain network;
rescinding the distributed digital credential issued to the requestor; and
removing personally identifiable information of the requestor.

4. The method of claim 3, wherein rescinding the distributed digital credential issued to the requestor further includes:
revoking the distributed digital credential;
deleting a trusted triple data structure, the trusted triple data structure comprised of: (a) a public key, (b) a link to an enterprise application on a server for which the requestor is authenticated, and (c) one or more third-party accreditations in the one or more claims as validated; and
deleting from private storage any identity documentation corresponding to the requestor.

5. The method of claim 4, wherein transactions from a requesting user that has withdrawn their credential remain in one or more nodes of the permissioned blockchain network and tied to an organization to which the requesting user was assigned with name, license and personally identifiable information of the requesting user removed.

6. The method of claim 1, wherein: (i) the identity documentation identifying the requestor is, at least in part, captured by the requestor at a time of making the first request and (ii) the one or more claims are made by an entity administrator supporting a role, as determined by rules of a trust framework adopted by network members.

7. The method of claim 1, wherein authenticating the requestor further includes: storing in a private storage: (i) the identity documentation and (ii) the one or more claims.

8. The method of claim 1, further including validating by the validator server, the one or more claims, as determined by rules of a trust framework by: checking by the validator server, a state board of pharmacy database to verify that a pharmacist applying for an ID is really the pharmacist in charge of the pharmacy they claim to manage.

9. The method of claim 8, further including the validator server issuing one or more challenges to the requestor; and based at least in part upon responses from the requestor, validating: (i) the identity documentation and (ii) the one or more claims.

10. The method of claim 9, wherein challenges are selected from a set comprising of: (i) questions asked through a secure channel, (ii) requests to take a photo of themselves holding an identification, and (iii) invert or flip the identification in a subsequent photo.

11. The method of claim 2, wherein granting a distributed digital credential further includes: generating and sending to the requestor, a token for creating a public-private key pair.

12. The method of claim 11, wherein granting a distributed digital credential further includes: obtaining a digital ID comprising a pseudonymized user ID of the requestor authenticated from a public key and a digital signature.

13. The method of claim 11, wherein granting a distributed digital credential further includes: storing a credential in a public key registry as a trusted triple data structure comprised of: (a) a public key, (b) a link to an enterprise application on a server for which the requestor is being authenticated, and (c) one or more third-party accreditations in the one or more claims as validated.

14. The method of claim 13, wherein no registry node contains credentials for all users permitted access to the permissioned blockchain network.

15. The method of claim 2, further including: receiving notification from the validator server that an event affecting at least one claim of the one or more claims has been detected or input of a manual review has been received; and revoking the distributed digital credential in the permissioned blockchain network.

16. The method of claim 15, wherein an event affecting the at least one claim of the one or more claims includes: an external validator checking a state board of pharmacy database, based, at least in part, upon an expiry of a 24-hour timer, for any changes in listed pharmacists in charge for each pharmacy and notifying to make any necessary revocations.

17. The method of claim 7, further including providing at least some of the identity documentation maintained in a private storage to an external server for audit.

18. The method of claim 1, wherein a machine intelligence process is used to authenticate the requestor using a trained neural network classifier trained using a training set of example submissions of evidence and ground truth outcomes.

19. The method of claim 18, further including identifying patterns in data points indicating clusters of data, and applying a label to each cluster; and training the trained neural network classifier with at least some of the clusters and labels.

20. The method of claim 18, wherein values for one or more labels associated with a training set of example submissions of evidence and ground truth outcomes are determined from a set including at least a plurality of counterfeit, expired, hacked, intentional adulteration, unfit for authentication, and fraudulent activity.

21. A method of granting and sharing credentials in a shared private permissioned blockchain data structure shared among network members of a blockchain network, the method comprising:

receiving, by a registry server and from a requesting application, a request to authenticate one or more identity claims of a requesting user to permit access to data stored in blocks in the shared private permissioned blockchain data structure shared among network members, the request including: (i) identity documentation identifying the requesting user and captured at a time of making the request and (ii) one or more claims made by an entity administrator supporting a role, as determined by rules of a trust framework adopted by the network members;

storing in a private storage by the registry server, the (i) identity documentation and (ii) claims;

redacting pictures captured of the requesting user from (i) the identity documentation and (ii) the one or more claims;

sending the identity documentation and the one or more claims to a validator server;

upon obtaining, by the registry server and from the validator server, an approval validating: (i) the identity documentation and (ii) the one or more claims made by an entity administrator, generating and sending a one-time token for creating a public-private key pair; and granting, by the registry server, a credential in the blockchain network based upon validation of (i) the identity documentation and (ii) the claims, the credential being stored in a public key registry at the registry server as a trusted triple data structure comprised of (a) a public key of the public-private key pair, (b) a link to an enterprise application on a server corresponding to the registry server, and (c) one or more third-party accreditations in the one or more claims as validated; and providing, by the registry server, the trusted triple data structure as verification of the credential to a blockchain network member as requested; thereby enabling the blockchain network member to restrict data from blocks stored in the shared private permissioned blockchain data structure to credentialed users.

22. The method of claim 21, further including displaying a first block of the shared private permissioned blockchain data structure using a first color denoting a first network member as a source of the first block and displaying a second block of the shared private permissioned blockchain data structure using a second color, different from the first color, and denoting a second network member as a source of the second block.

23. A system comprising:

a registry server including a processor and software that when executed implements processing including:

receiving from a requestor, a first request by the requestor to access a permissioned blockchain network, wherein the first request includes: (i) identity documentation identifying the requestor, (ii) one or more claims, and (iii) one or more submissions of evidence;

authenticating the requestor based at least in part upon the one or more submissions of evidence, including:

redacting pictures captured of the requestor from at least (i) the identity documentation and (ii) the one or more claims; and sending the identity documentation and the one or more claims without pictures to a validator server.

24. A non-transitory computer readable medium storing instructions, which instructions when executed by one or more processors perform processing including:

receiving from a requestor, a first request by the requestor to access a permissioned blockchain network, wherein the first request includes: (i) identity documentation identifying the requestor, (ii) one or more claims, and (iii) one or more submissions of evidence;

authenticating the requestor based at least in part upon the one or more submissions of evidence, including:

redacting pictures captured of the requestor from at least (i) the identity documentation and (ii) the one or more claims; and sending the identity documentation and the one or more claims without pictures to a validator server.

\* \* \* \* \*